US005712146A

United States Patent [19]
Khosla et al.

[11] Patent Number: 5,712,146
[45] Date of Patent: Jan. 27, 1998

[54] RECOMBINANT COMBINATORIAL GENETIC LIBRARY FOR THE PRODUCTION OF NOVEL POLYKETIDES

[75] Inventors: Chaitan Khosla, Stanford, Calif.; David A. Hopwood, Norwich, England; Suzanne Ebert-Khosla, Stanford, Calif.; Robert McDaniel, Palo Alto, Calif.; Hong Fu; Camilla Kao, both of Stanford, Calif.

[73] Assignee: The Leland Stanford Junior University, Palo Alto, Calif.

[21] Appl. No.: 486,645

[22] Filed: Jun. 7, 1995

Related U.S. Application Data

[63] Continuation-in-part of Ser. No. 238,811, May 6, 1994, which is a continuation-in-part of Ser. No. 164,301, Dec. 8, 1993, abandoned, which is a continuation-in-part of Ser. No. 123,732, Sep. 20, 1993, abandoned.

[51] Int. Cl.$^6$ ..................................................... C12N 1/20
[52] U.S. Cl. .................. 435/252.35; 435/148; 435/156; 435/320.1; 435/252.3; 435/252.33; 536/23.1; 536/23.2; 536/23.7
[58] Field of Search ........................... 435/252.35, 252.3, 435/76, 148, 172.3, 320.1, 240.2, 254.11; 536/23.1, 23.2, 23.7

[56] References Cited

U.S. PATENT DOCUMENTS 4,935,340  6/1990  Baltz et al. ................................. 435/6

OTHER PUBLICATIONS

Strohl et al. "Significance of anthraquinone formation resulting from the cloning of actinorhodin genes in heterologus streptomycetes" Molecular Microbiology 6(2), 147–152, Jan. 1992.
Rohr, J. "Combinatorial Biosynthesis—An approach in the near future?" Angew. Chem. Int. Ed. Engl. 34 (8), 881–885, May 1995.
Gordon et al., "Strategy and tactics in combinatorial organic synthesis. Application to drug discovery," Acc. Chem. Res. (1996) 29(3):144–154.
Hutchinson, "Drug synthesis by genetically engineered microorganisms," Bio/Technology (1994) 12:375–380.
McAlpine et al., "New antibiotics from genetically engineered actinomycetes. I. 2-Norerythromycines, isolation and structural determinations," The Jrnl. of Antibiotics, (1987) 40(8):1115–1122.
Strohl et al., "Expression of polyketide biosynthesis and regulatory genes in heterologous streptomycetes," J. Ind. Microbiol. (1991) 7:163–174.
Tsoi et al. "Combinatorial biosynthesis of unnatural and natural products: the polykitide example," Chem. Biol. Database Caplus on STN, Chemical Abstract No. 123:169385, (1995) 2(6):355–362.
Bartel et al. (1990) "Biosynthesis of anthraquinones by interspecies cloning of actinorhodin biosynthesis genes in streptomycetes: Clarification of actinorhodin gene functions," J. Bacteriol. 172(9):4816–4826.
Beck et al. (1990) "The multifunctional 6-methylsalicylic acid synthase gene of penicillium patulum. Its gene structure relative to that of other polyketide synthases," Eur. J. Biochem 192:487–498.
Bibb et al. (1989) "Analysis of the nucleotide sequence of the streptomyces glaucescens tcml genes provide key information about the enzymology of Polyketide antibiotic biosynthesis," EMBO J. 8(9):2727–2736.
Caballero et al. (1991) "Organisation and functions of the actVA region of the actinorhodin biosynthetic gene cluster of Streptomyces coelicolor," Mol. Gen. Genet. 230:401–412.
Cortes et al. (1990) "An unusually large multifunctional polypeptide in the erythromycin–produciny polyketide synthase of Saccharopolyspora Erythraea,"Nature (1990) 348:176–178.
Davis et al. (1994) "Functional mapping of a polyketide synthase from aspergillus terreus Involved in lovastatin synthesis," Abst. of the Genetics of Industrial Microorganisms Mtg. P288:192.
Donadio et al. (1991) "Modular organization of genes required for complex polyketide biosynthesis," Science 252:675–679.
Donadio et al. (1992) "Biosynthesis of the erythromycin macrolactone and a rational approach for producing hybrid macrolides," Gene 115:97–103.
Fernandez–Moreno et al. (1991) "The act cluster contains regulatory and antibiotic export genes, direct targets for translational control by the bldA tRNA gene of Streptomyces," Cell 66:769–780.
Fernandez–Moreno et al. (1992) "Nucleotide sequence and deduced functions of a set of cotranscribed genes of streptomyces coelicolor A3(2) including the polyketide synthase for the antibiotic actinorhodin," J. Biol. Chem. 267:19278–19290.
Floss (1991) "Genetic engineering of hybrid antibiotics—a progress report," Tetrahydron 47(31):6045–6058.
Fu (1994) "Engineered biosynthesis of novel polyketides: Stereochemical course of two reactions catalyzed by a polyketide synthase," Biochemistry 33(31):9321–9326.
Hallam (1988) "Nucleotide sequence, transcription and deduced function of a gene involved in polyketide antibiotic synthesis in Streptomyces coelicolor," Gene 74:305–320.
Hershberger et al. (1989) "Genetics and molecular biology of industrial microorganisms," Am. Soc. for Microbiol. (Washington, DC) pp. 68–84.
Hopwood et al. (1985) "Product of 'Hybrid' antibiotics by genetic engineering," Nature 314 (6012):642–644.

(List continued on next page.)

Primary Examiner—Charles L. Patterson, Jr.
Assistant Examiner—Nashaat T. Nashed
Attorney, Agent, or Firm—Kenneth Barovsky; Bozicevic & Reed LLP

[57] ABSTRACT

Novel polyketides and novel methods of efficiently producing both new and known polyketides, using recombinant technology, are disclosed. In particular, a novel host-vector system is described which is used to produce polyketide synthases which in turn catalyze the production of a variety of polyketides.

5 Claims, 26 Drawing Sheets

OTHER PUBLICATIONS

Katz et al. (1993) "Polyketide synthesis: Prospects for hybrid antibiotics," *Ann. Review Microbiol.* 47:875–912.

Khosla et al. (1993) "Genetic construction and functional analysis of hybrid polyketide synthases containing heterologous acyl carrier proteins," *J. Bacteriol.* 175:2197–2204.

Khosla et al. (1992) "Targeted gene replacements in a Streptomyces polyketide synthase gene cluster: role for the acyl carrier protein," *Molec. Microbiol.* 6(21):3237–3249.

MacNeil et al. (1992) "Complex organization of the *Streptomyces avermitilis* Genes encoding the avermectin polyketide synthase," *Gene* 115:119–125).

Malpartida et al. (1984) "Molecular cloning of the whole biosynthetic pathway of a streptomyces antibiotic and its expression in a heterologous host," *Nature* 309:462–464.

Malpartida et al. (1986) "Physical and Genetic characterisation of the gene cluster for the antibiotic actinorhodin in *Streptomyces coelicolor* A3(2)," *Mol. Gen. Genet.* 205:66–73.

Malpartida et al. (1987) "Homology between streptomyces genes coding for synthesis of different polyketides used to clone antibiotic biosynthetic genes," *Nature* 325(6107):818–821.

McDaniel et al. (1993) "Engineered biosynthesis of novel polyketides," *Science* 262:1546–1550.

Sherman et al. (1992) "Functional replacement of genes for individual polyketide synthase components in *Streptomyces coelicolor* A3(2) by hetergenous genes from a different polyketide pathway," *J. Bacteriol.* 174:6184–6190.

Sherman et al. (1989) "Structure and deduced function of the granaticin–producing polyketide synthase gene cluster of *streptomyces violaceoruber* Tü22," *EMBO J.* 8:2717–2725.

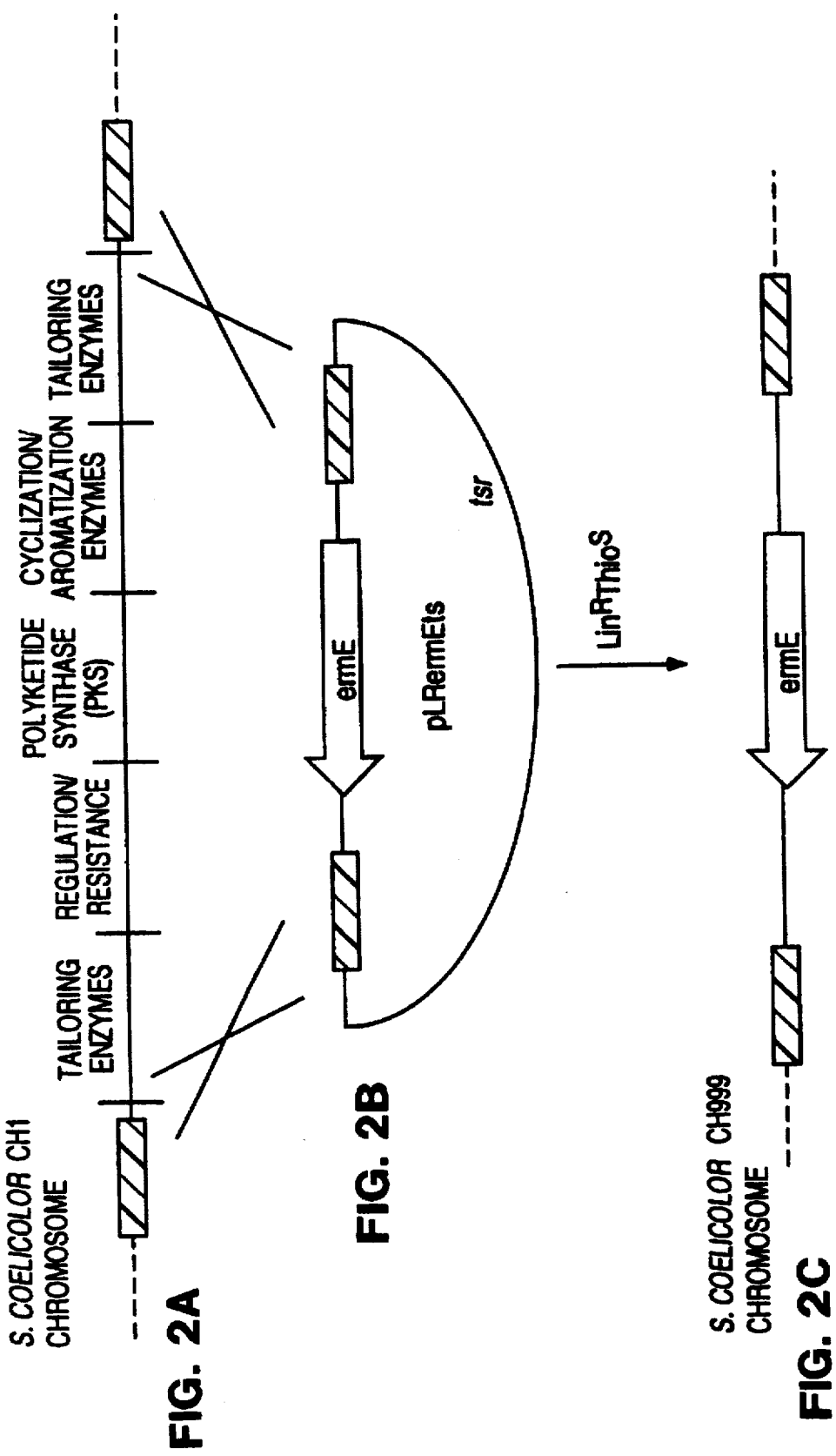

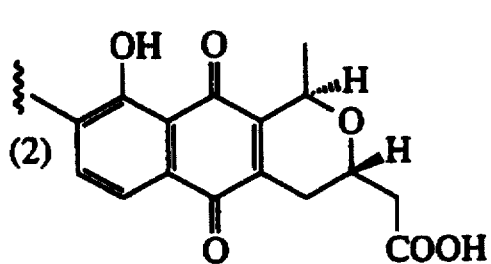
ACTINORHODIN (3)
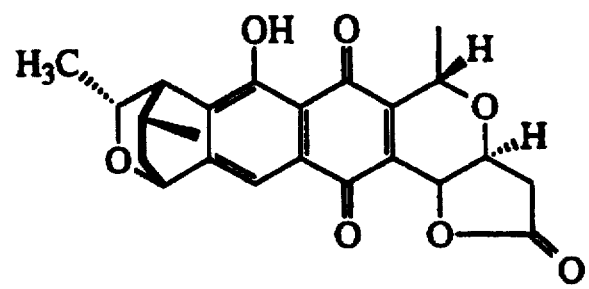
GRANATICIN (4)
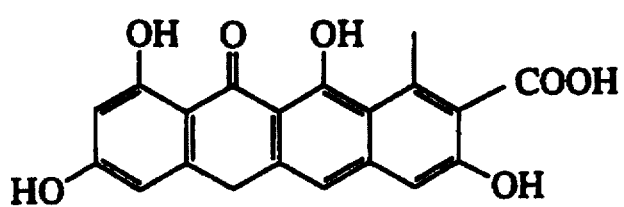
TETRACENOMYCIN F1 (5)
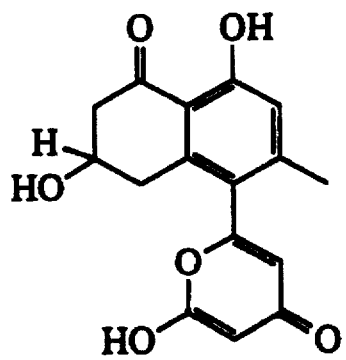
MUTACTIN (6)
FIG. 5

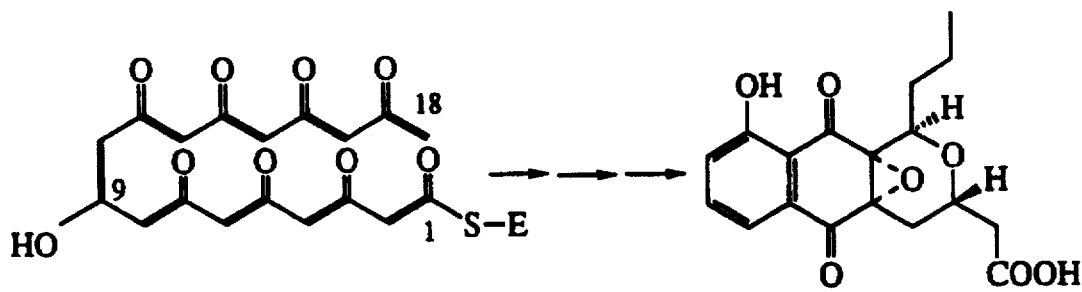
FRENOLICIN B (7)
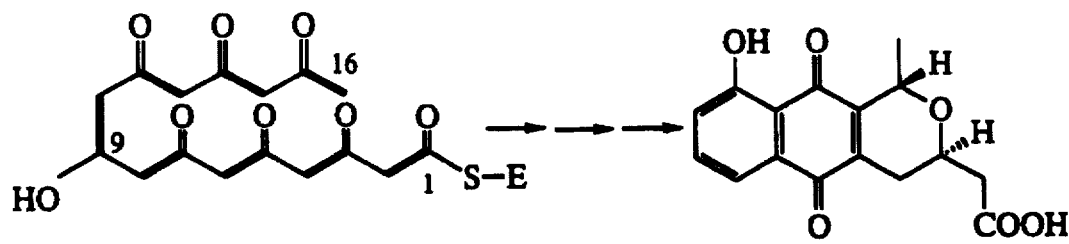
NANAOMYCIN A (8)
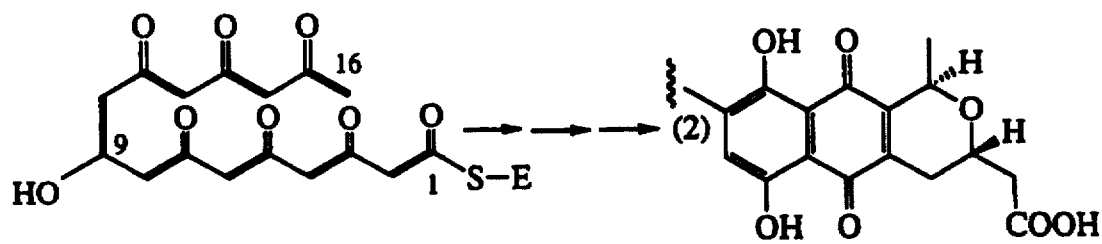
ACTINORHODIN (3)
FIG. 7

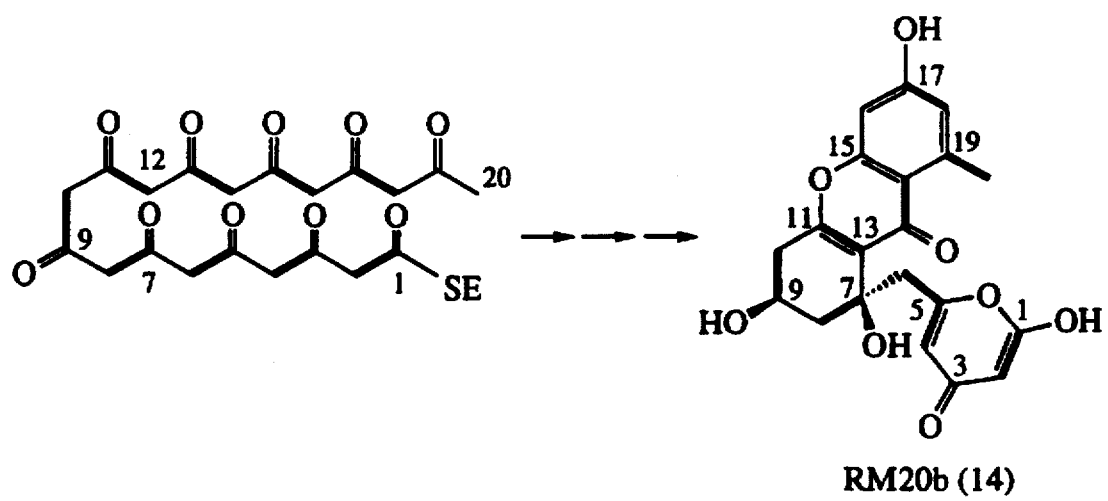
RM20b (14)
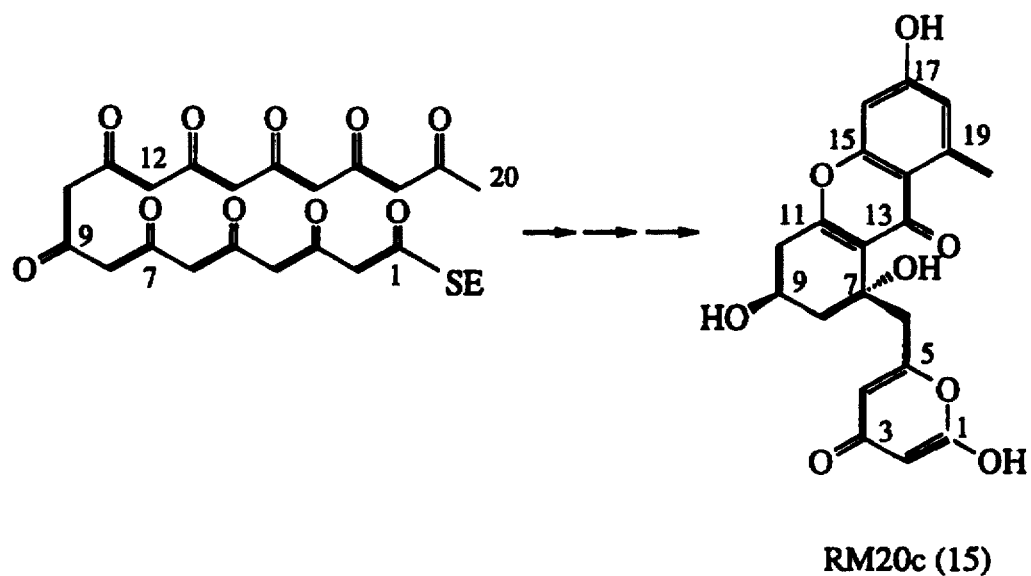
RM20c (15)
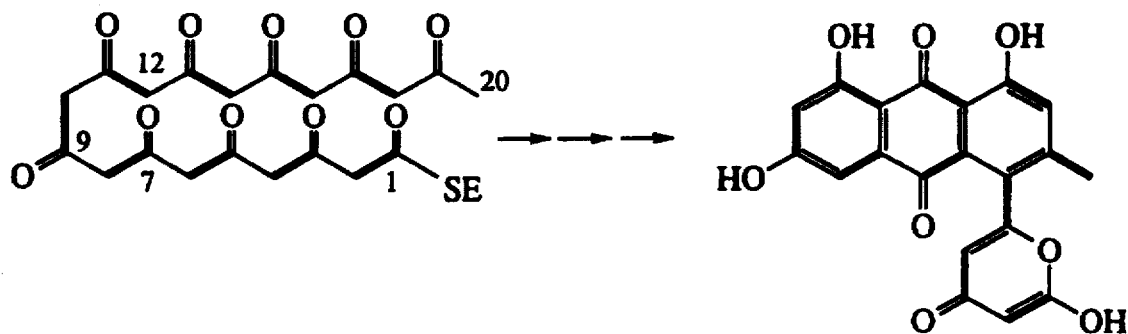
SEK15b (16)
FIG. 8C

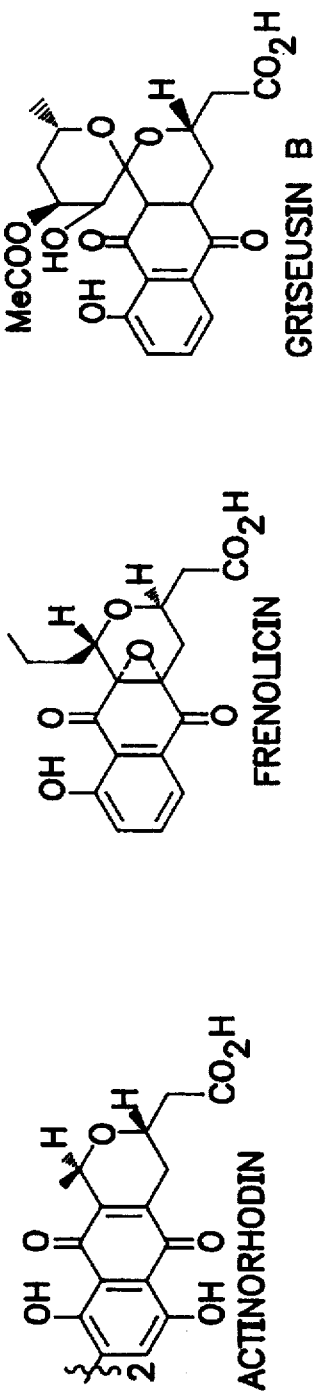
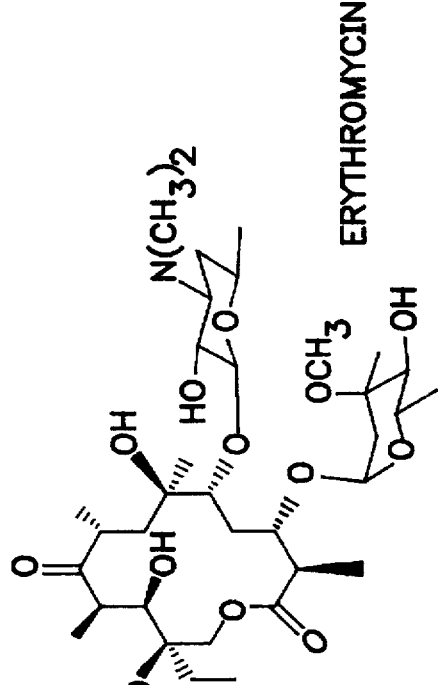
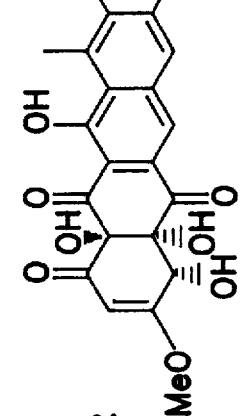
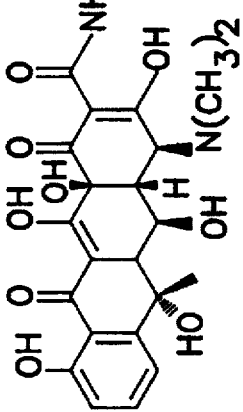
FIG. 11A

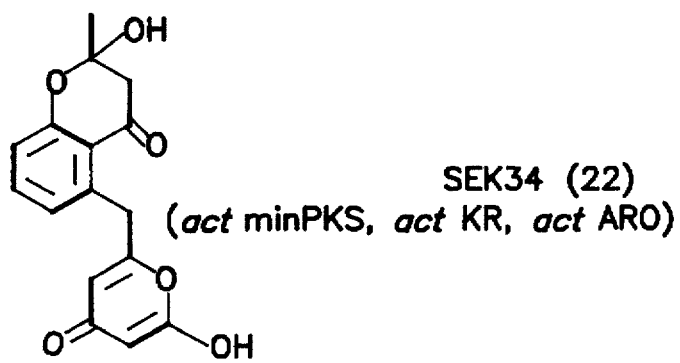
SEK34 (22)
(*act* minPKS, *act* KR, *act* ARO)
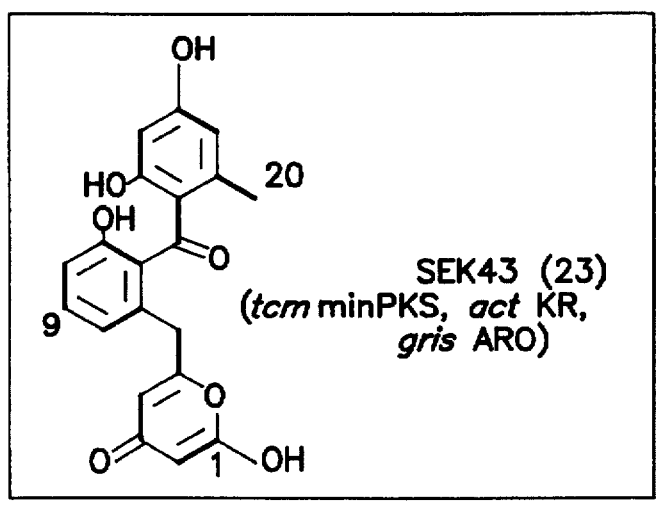
SEK43 (23)
(*tcm* minPKS, *act* KR, *gris* ARO)
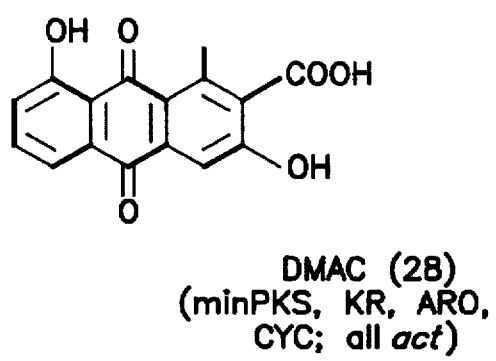
DMAC (28)
(minPKS, KR, ARO, CYC; all *act*)
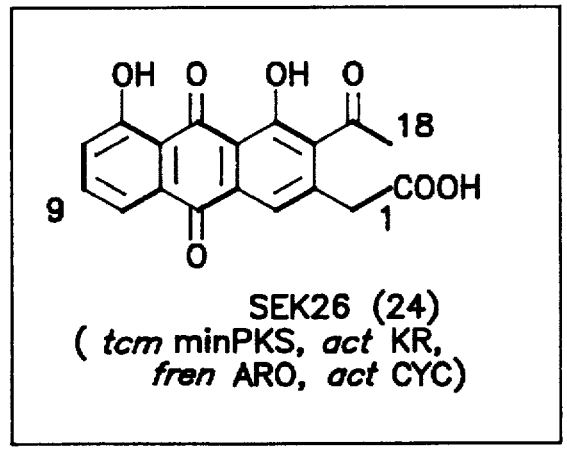
SEK26 (24)
(*tcm* minPKS, *act* KR, *fren* ARO, *act* CYC)
FIG. 16

SEK43 (23)

SEK26 (24)

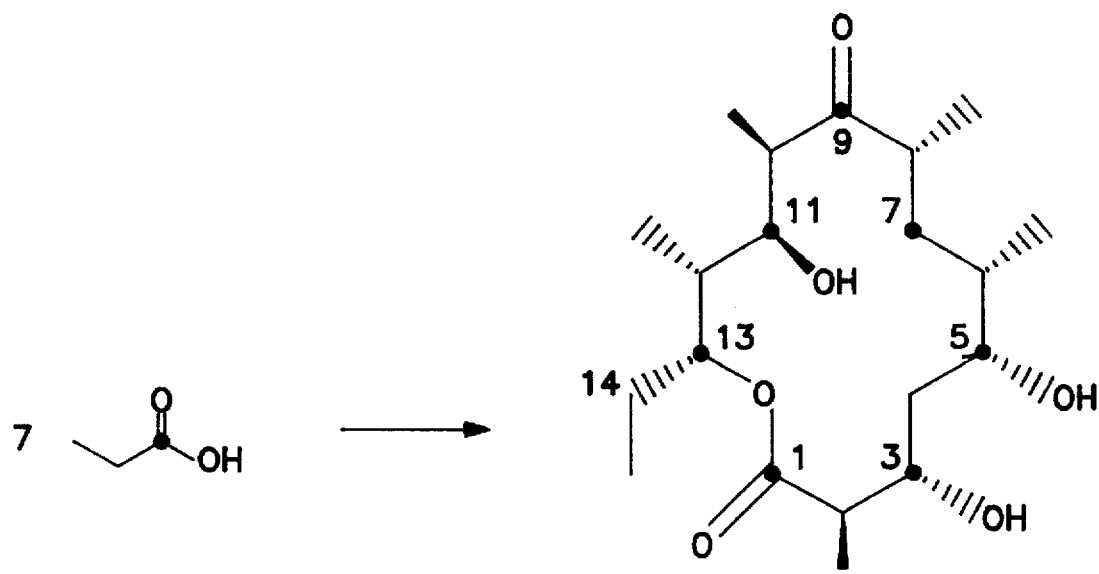
(17)
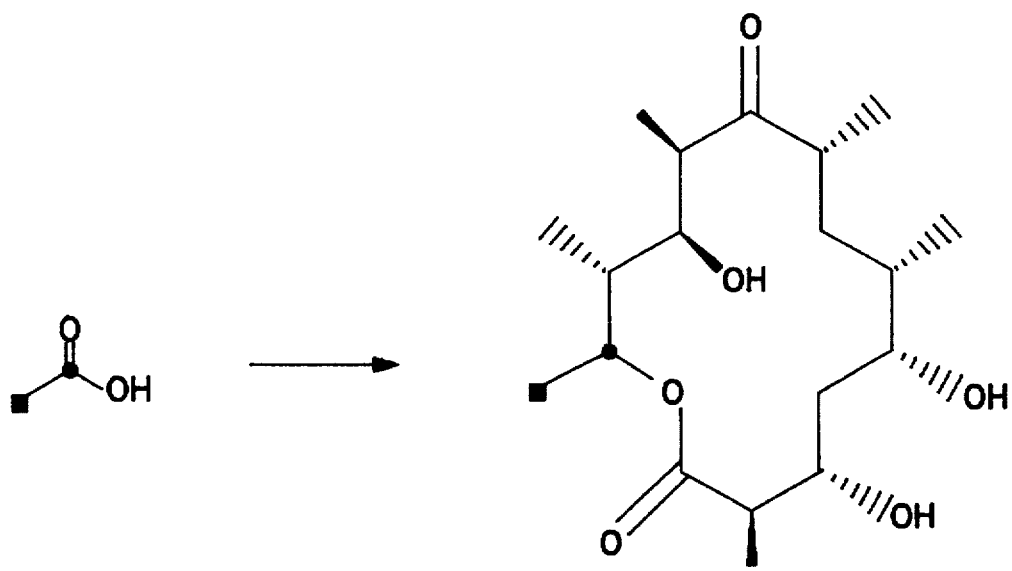
(18)
FIG. 20

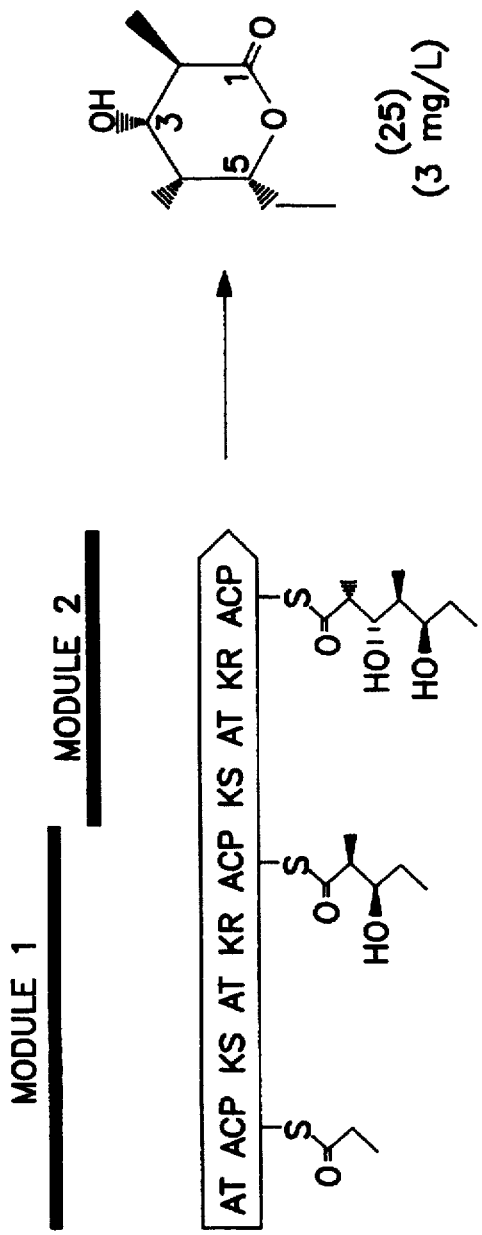
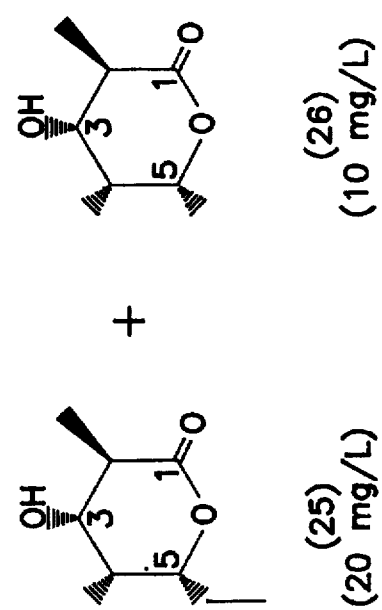
FIG. 2A
FIG. 2B

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 42 base pairs
      ( B ) TYPE: nucleic acid
      ( C ) STRANDEDNESS: both
      ( D ) TOPOLOGY: linear ( i i ) MOLECULE TYPE: other nucleic acid ( x i ) SEQUENCE DESCRIPTION: SEQ ID NO:1:

CCACCGGACG AACGCATCGA TTAATTAAGG AGGACCATCA TG      42

( 2 ) INFORMATION FOR SEQ ID NO:2:

( i ) SEQUENCE CHARACTERISTICS:
      ( A ) LENGTH: 25 base pairs
      ( B ) TYPE: nucleic acid
      ( C ) STRANDEDNESS: both
      ( D ) TOPOLOGY: linear ( i i ) MOLECULE TYPE: other nucleic acid ( x i ) SEQUENCE DESCRIPTION: SEQ ID NO:2:

NTGAATGCAT GGAGGAGCCA TCATG      25

RECOMBINANT COMBINATORIAL GENETIC LIBRARY FOR THE PRODUCTION OF NOVEL POLYKETIDES

CROSS-REFERENCE TO RELATED APPLICATIONS

This application is a continuation-in-part of U.S. patent application Ser. No. 08/238,811, filed May 6, 1994, which is a continuation-in-part of U.S. patent application Ser. No. 08/164,301, filed Dec. 8, 1993, now abandoned, which is a continuation-in-part of U.S. application Ser. No. 08/123 732 filed Sep. 20, 1993 now abandoned, from which priority is claimed pursuant to 35 U.S.C. § 120, and which disclosures are hereby incorporated by reference in their entireties.

REFERENCE TO GOVERNMENT CONTRACT

This invention was made with United States Government support in the form of a grant from the National Science Foundation (BCS-9209901).

TECHNICAL FIELD

The present invention relates generally to polyketides and polyketide synthases. In particular, the invention pertains to the recombinant production of polyketides using a novel host-vector system. In addition, the invention relates to the combinatorial biosynthesis of polyketides.

BACKGROUND OF THE INVENTION

Polyketides are a large, structurally diverse family of natural products. Polyketides possess a broad range of biological activities including antibiotic and pharmacological properties. For example, polyketides are represented by such antibiotics as tetracyclines and erythromycin, anticancer agents including daunomycin, immunosuppressants, for example FK506 and rapamycin, and veterinary products such as monensin and avermectin. Polyketides occur in most groups of organisms and are especially abundant in a class of mycelial bacteria, the actinomycetes, which produce various polyketides.

Polyketide synthases (PKSs) are multifunctional enzymes related to fatty acid synthases (FASs). PKSs catalyze the biosynthesis of polyketides through repeated (decarboxylative) Claisen condensations between acylthioesters, usually acetyl, propionyl, malonyl or methylmalonyl. Following each condensation, they introduce structural variability into the product by catalyzing all, part, or none of a reductive cycle comprising a ketoreduction, dehydration, and enoylreduction on the β-keto group of the growing polyketide chain. PKSs incorporate enormous structural diversity into their products, in addition to varying the condensation cycle, by controlling the overall chain length, choice of primer and extender units and, particularly in the case of aromatic polyketides, regiospecific cyclizations of the nascent polyketide chain. After the carbon chain has grown to a length characteristic of each specific product, it is released from the synthase by thiolysis or acyltransfer. Thus, PKSs consist of families of enzymes which work together to produce a given polyketide. It is the controlled variation in chain length, choice of chain-building units, and the reductive cycle, genetically programmed into each PKS, that contributes to the variation seen among naturally occurring polyketides.

Two general classes of PKSs exist. One class, known as Type I PKSs, is represented by the PKSs for macrolides such as erythromycin. These "complex" or "modular" PKSs include assemblies of several large multifunctional proteins carrying, between them, a set of separate active sites for each step of carbon chain assembly and modification (Cortes, J. et al. *Nature* (1990) 348:176; Donadio, S. et al. *Science* (1991) 252:675; MacNeil, D. J. et al. *Gene* (1992) 115:119). Structural diversity occurs in this class from variations in the number and type of active sites in the PKSs. This class of PKSs displays a one-to-one correlation between the number and clustering of active sites in the primary sequence of the PKS and the structure of the polyketide backbone.

The second class of PKSs, called Type II PKSs, is represented by the synthases for aromatic compounds. Type II PKSs have a single set of iteratively used active sites (Bibb, M. J. et al. *EMBO J.* (1989) 8:2727; Sherman, D. H. et al. *EMBO J.* (1989) 8:2717; Fernandez-Moreno, M. A. et al. *J. Biol. Chem.* (1992) 267:19278).

In contrast, fungal PKSs, such as the 6-methylsalicylic acid PKS, consist of a single multi-domain polypeptide which includes all the active sites required for the biosynthesis of 6-methylsalicylic acid (Beck, J. et al. *Eur. J. Biochem.* (1990) 192:487–498; Davis, R. et al. *Abstr. of the Genetics of Industrial Microorganism Meeting, Montreal*, abstr. P288 (1994)).

Streptomyces is an actinomycete which is an abundant producer of aromatic polyketides. In each Streptomyces aromatic PKS so far studied, carbon chain assembly requires the products of three open reading frames (ORFs). ORF1 encodes a ketosynthase (KS) and an acyltransferase (AT) active site; ORF2 encodes a PKS chain length determining factor (CLF); and ORF3 encodes a discrete acyl carrier protein (ACP).

*Streptomyces coelicolor* produces the blue-pigmented polyketide, actinorhodin. The actinorhodin gene cluster (act), has been cloned (Malpartida, F. and Hopwood, D. A. *Nature* (1984) 309:462; Malpartida, F. and Hopwood, D. A. *Mol. Gen. Genet.* (1986) 205:66) and completely sequenced (Fernandez-Moreno, M. A. et al. *J. Biol. Chem.* (1992) 267:19278; Hallam, S. E. et al. *Gene* (1988) 74:305; Fernandez-Moreno, M. A. et al. *Cell* (1991) 66:769; Caballero, J. et al. *Mol. Gen. Genet.* (1991) 230:401). The cluster encodes the PKS enzymes described above, a cyclase and a series of tailoring enzymes involved in subsequent modification reactions leading to actinorhodin, as well as proteins involved in export of the antibiotic and at least one protein that specifically activates transcription of the gene cluster. Other genes required for global regulation of antibiotic biosynthesis, as well as for the supply of starter (acetyl CoA) and extender (malonyl CoA) units for polyketide biosynthesis, are located elsewhere in the genome.

The act gene cluster from *S. coelicolor* has been used to produce actinorhodin in *S. parvulus*. Malpartida, F. and Hopwood, D. A. *Nature* (1984) 309:462. Bartel et al. *J. Bacteriol.* (1990) 172:4816–4826, recombinantly produced aloesaponarin II using *S. galilaeus* transformed with an *S. coelicolor* act gene cluster consisting of four genetic loci, actI, actIII, actIV and actVII. Hybrid PKSs, including the basic act gene set but with ACP genes derived from granaticin, oxytetracycline, tetracenomycin and frenolicin PKSs, have also been designed which are able to express functional synthases. Khosla, C. et al. *J. Bacteriol.* (1993) 175:2197–2204. Hopwood, D. A. et al. *Nature* (1985) 314:642–644, describes the production of hybrid polyketides, using recombinant techniques. Sherman, D. H. et al. *J. Bacteriol.* (1992) 174:6184–6190, reports the transformation of various *S. coelicolor* mutants, lacking different components of the act PKS gene cluster, with the corresponding granaticin (gra) genes from *S. violaceoruber*, in trans.

However, no one to date has described the recombinant production of polyketides using genetically engineered host cells which substantially lack their entire native PKS gene clusters.

SUMMARY OF THE INVENTION

The present invention provides for novel polyketides and novel methods of efficiently producing both new and known polyketides, using recombinant technology. In particular, a novel host-vector system is used to produce PKSs which in turn catalyze the production of a variety of polyketides. Furthermore, methods are provided for the combinatorial biosynthesis of polyketide libraries which can be screened for active compounds. Such polyketides are useful as antibiotics, antitumor agents, immunosuppressants and for a wide variety of other pharmacological purposes.

Accordingly, in one embodiment, the invention is directed to a genetically engineered cell which expresses a polyketide synthase (PKS) gene cluster in its native, nontransformed state, the genetically engineered cell substantially lacking the entire native PKS gene cluster.

In another embodiment, the invention is directed to the genetically engineered cell as described above, wherein the cell comprises:

(a) a replacement PKS gene cluster which encodes a PKS capable of catalyzing the synthesis of a polyketide; and (b) one or more control sequences operatively linked to the PKS gene cluster, whereby the genes in the gene cluster can be transcribed and translated in the genetically engineered cell, with the proviso that when the replacement PKS gene cluster comprises an entire PKS gene set, at least one of the PKS genes or control elements is heterologous to the cell.

In particularly preferred embodiments, the genetically engineered cell is *Streptomyces coelicolor*, the cell substantially lacks the entire native actinorhodin PKS gene cluster and the replacement PKS gene cluster comprises a first gene encoding a PKS ketosynthase and a PKS acyltransferase active site (KS/AT), a second gene encoding a PKS chain length determining factor (CLF), and a third gene encoding a PKS acyl carrier protein (ACP).

In another embodiment, the invention is directed to a method for producing a recombinant polyketide comprising:

(a) providing a population of cells as described above; and (b) culturing the population of cells under conditions whereby the replacement PKS gene cluster present in the cells, is expressed.

In still another embodiment, the invention is directed to a method for producing a recombinant polyketide comprising:

(a) inserting a first portion of a replacement PKS gene cluster into a donor plasmid and inserting a second portion of a replacement PKS gene cluster into a recipient plasmid, wherein the first and second portions collectively encode a complete replacement PKS gene cluster, and further wherein:

i. the donor plasmid expresses a gene which encodes a first selection marker and is capable of replication at a first, permissive temperature and incapable of replication at a second, non-permissive temperature;

ii. the recipient plasmid expresses a gene which encodes a second selection marker; and iii. the donor plasmid comprises regions of DNA complementary to regions of DNA in the recipient plasmid, such that homologous recombination can occur between the first portion of the replacement PKS gene cluster and the second portion of the replacement gene cluster, whereby a complete replacement gene cluster can be generated;

(b) transforming the donor plasmid and the recipient plasmid into a host cell and culturing the transformed host cell at the first, permissive temperature and under conditions which allow the growth of host cells which express the first and/or the second selection markers, to generate a first population of cells;

(c) culturing the first population of cells at the second, non-permissive temperature and under conditions which allow the growth of cells which express the first and/or the second selection markers, to generate a second population of cells which includes host cells which contain a recombinant plasmid comprising a complete PKS replacement gene cluster;

(d) transferring the recombinant plasmid from the second population of cells into the genetically engineered cell described above to generate transformed genetically engineered cells; and (e) culturing the transformed genetically engineered cells under conditions whereby the replacement PKS gene cluster present in the cells is expressed.

In a further embodiment, the invention is drawn to a method for preparing a combinatorial polyketide library comprising:

(a) providing a population of vectors wherein the vectors comprise a random assortment of polyketide synthase (PKS) genes, modules, active sites, or portions thereof and one or more control sequences operatively linked to said genes;

(b) transforming a population of host cells with said population of vectors;

(c) culturing said population of host cells under conditions whereby the genes in said gene cluster can be transcribed and translated, thereby producing a combinatorial library of polyketides.

In still another embodiment, the invention is drawn to a method for producing a combinatorial polyketide library comprising:

a) providing one or more expression plasmids containing a random assortment of 1 or more first modules of a modular PKS gene cluster wherein the expression plasmids express a gene which encodes a first selection marker;

b) providing a pool of donor plasmids containing a random assortment of second modules of a modular PKS gene cluster wherein the donor plasmids express a gene which encodes a second selection marker and further wherein the donor plasmids comprise regions of DNA complementary to regions of DNA in the expression plasmids, such that homologous recombination can occur between the first and second modules;

c) transforming the expression plasmids and the donor plasmids into a first population of host cells to produce a first pool of transformed host cells;

d) culturing the first pool of transformed host cells under conditions which allow homologous recombination to occur between the first and second modules to produce recombined plasmids comprising recombined PKS gene cluster modules;

e) transferring the recombined plasmids into a second population of host cells to generate a second pool of transformed host cells; and f) culturing the second pool of transformed host cells under conditions whereby the combinatorial polyketide library is produced.

In yet another embodiment, the invention is directed to a polyketide compound having the structural formula (I)

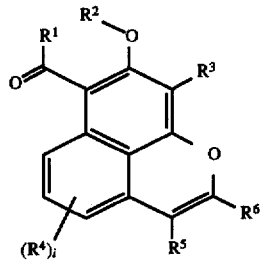

wherein:

$R^1$ is selected from the group consisting of hydrogen and lower alkyl and $R^2$ is selected from the group consisting of hydrogen, lower alkyl and lower alkyl ester, or wherein $R^1$ and $R^2$ together form a lower alkylene bridge optionally substituted with one to four hydroxyl or lower alkyl groups;

$R^3$ and $R^5$ are independently selected from the group consisting of hydrogen, halogen, lower alkyl, lower alkoxy, amino, lower alkyl mono- or di-substituted amino and nitro;

$R^4$ is selected from the group consisting of halogen, lower alkyl, lower alkoxy, amino, lower alkyl mono- or di-substituted amino and nitro;

$R^6$ is selected from the group consisting of hydrogen, lower alkyl, and —$CHR^7$—$(CO)R^8$ where $R^7$ and $R^8$ are independently selected from the group consisting of hydrogen and lower alkyl; and i is 1, 2 or 3.

In another embodiment, the invention related to novel polyketides having the structures

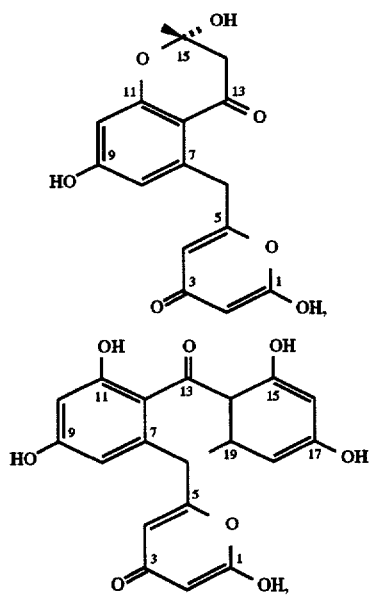

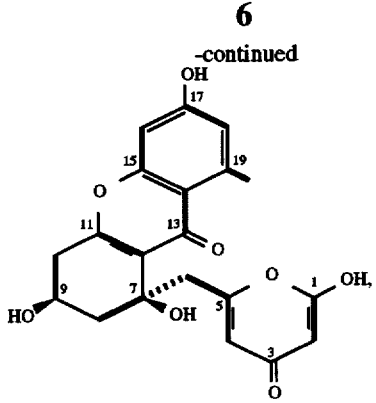

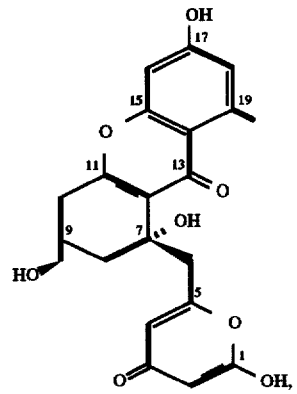

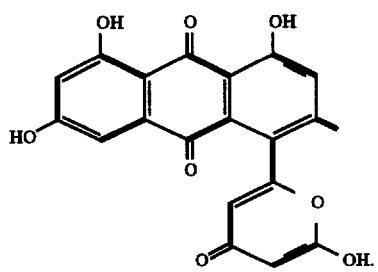

In another embodiment, the invention is directed to a polyketide compound formed by catalytic cyclization of an enzyme-bound ketide having the structure (II)

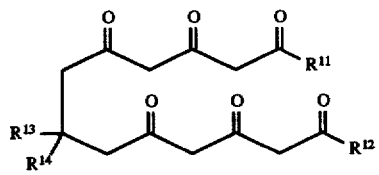

wherein:

$R^{11}$ is selected from the group consisting of methyl, —$CH_2(CO)CH_3$ and —$CH_2(CO)CH_2(CO)CH_3$;

$R^{12}$ is selected from the group consisting of —S—E and —$CH_2(CO)$—S—E, wherein E represents a polyketide synthase produced by the genetically engineered cells above; and one of $R^{13}$ and $R^{14}$ is hydrogen and the other is hydroxyl, or $R^{13}$ and $R^{14}$ together represent carbonyl.

In still another embodiment, the invention is directed to a method for producing an aromatic polyketide, comprising effecting cyclization of an enzyme-bound ketide having the structure (II), wherein cyclization is induced by the polyketide synthase.

In a further embodiment, the invention is directed to a polyketide compound having the structural formula (III)

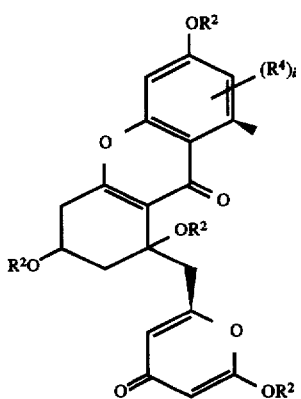

wherein $R^2$ and $R^4$ are as defined above and i is 0, 1 or 2.

In another embodiment, the invention is directed to a polyketide compound having the structural formula (IV)

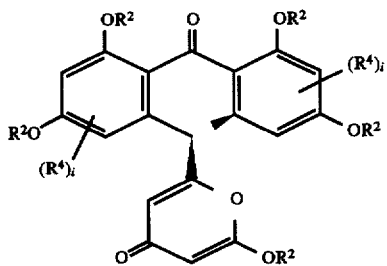

wherein $R^2$ $R^4$ and i are as defined above for structural formula (III).

In still anther embodiment, the invention is directed to a polyketide compound having the structural formula (V)

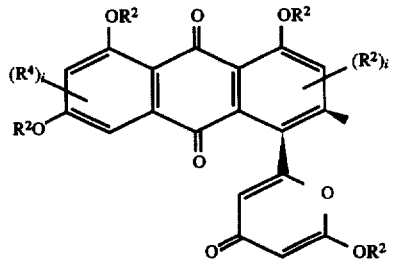

wherein $R^2$, $R^4$ and i are as defined above for structural formula (III).

These and other embodiments of the subject invention will readily occur to those of ordinary skill in the art in view of the disclosure herein.

BRIEF DESCRIPTION OF THE FIGURES

FIG. 2 shows the strategy for making S. coelicolor CH999. FIG. 2A depicts the structure of the act gene cluster present on the S. coelicolor CH1 chromosome. FIG. 2B shows the structure of pLRemEts and FIG. 2C shows the portion of the CH999 chromosome with the act gene cluster deleted.

FIG. 5 provides the structures of actinorhodin (3), granaticin (4), tetracenomycin (5) and mutactin (6), referenced in Example 4.

FIG. 7 schematically illustrates the preparation, via cyclization of the polyketide precursors, of frenolicin (7), nanomycin (8) and actinorhodin (3).

FIG. 16 shows the structures of SEK34 (22) the two novel polyketides SEK43 (23) and SEK26 (24) and other polyketides produced by genetic engineering in S. coelicolor CH999.

FIG. 20 schematically illustrates the preparation of 6-deoxyerythromolide B (17) from propionate and 8,8a-deoxyoleandolide (18) from an acetate starter.

FIG. 21A shows the biosynthesis of (2R,3S,4S,5R)-2,4-dimethyl-3,5-dihydroxy-n-heptanoic acid δ-lactone (25) by DEBS1 in S. coelicolor CH999. FIG. 21B shows the biosynthesis of (25) and (2R,3S,4S,5R)-2,4-dimethyl-3,5-dihydroxy-n-hexanoic acid δ-lactone (26) by the "1+2+TE" PKS in S. coelicolor CH999. The vertical line between ACP-2 and the TE represents the fusion junction in this deletion mutant.

DETAILED DESCRIPTION OF THE INVENTION

Figure 1A:
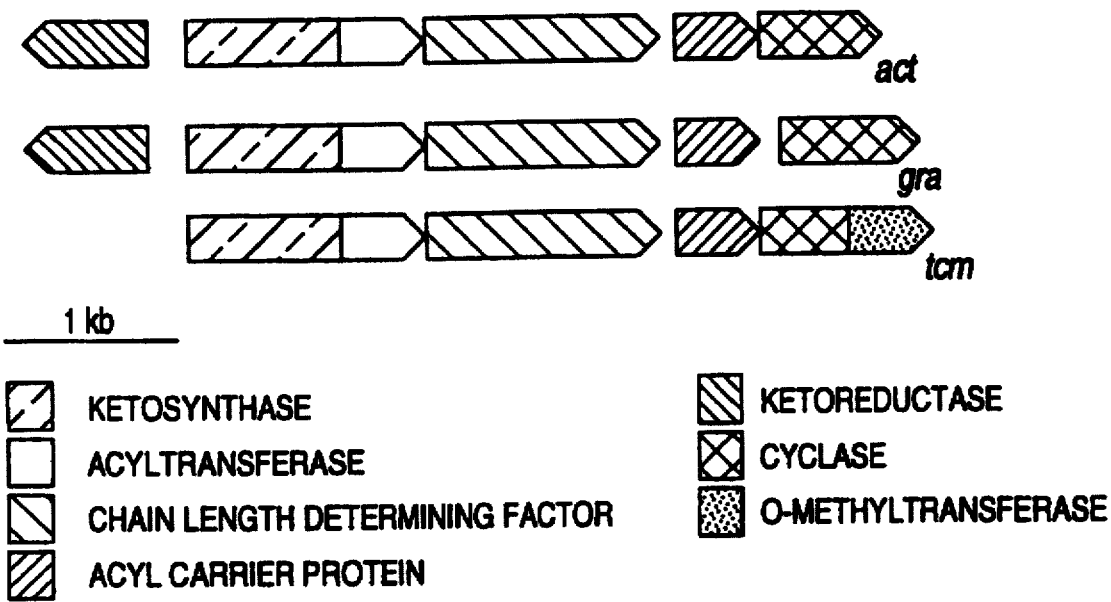
FIG. 1A shows the gene clusters for act, gra, and tcm PKSs and cyclases.

The practice of the present invention will employ, unless otherwise indicated, conventional methods of chemistry, microbiology, molecular biology and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, reference to "a polyketide" includes mixtures of polyketides, reference to "a polyketide synthase" includes mixtures of polyketide synthases, and the like.

A. Definitions

In describing the present invention, the following terms will be employed, and are intended to be defined as indicated below.

By "replacement PKS gene cluster" is meant any set of PKS genes capable of producing a functional PKS when under the direction of one or more compatible control elements, as defined below, in a host cell transformed therewith. A functional PKS is one which catalyzes the synthesis of a polyketide. The term "replacement PKS gene cluster" encompasses one or more genes encoding for the various proteins necessary to catalyze the production of a polyketide. A "replacement PKS gene cluster" need not include all of the genes found in the corresponding cluster in nature. Rather, the gene cluster need only encode the necessary PKS components to catalyze the production of an active polyketide. Thus, as explained further below, if the gene cluster includes, for example, eight genes in its native state and only three of these genes are necessary to provide an active polyketide, only these three genes need be present. Furthermore, the cluster can include PKS genes derived from a single species, or may be hybrid in nature with, e.g., a gene derived from a cluster for the synthesis of a particular polyketide replaced with a corresponding gene from a cluster for the synthesis of another polyketide. Hybrid clusters can include genes derived from both Type I and Type II PKSs. As explained above, Type I PKSs include several large multifunctional proteins carrying, between them, a set of separate active sites for each step of carbon chain assembly and modification. Type II PKSs, on the other hand, have a single set of iteratively used active sites. These classifications are well known. See, e.g., Hopwood, D. A. and Khosla, C. *Secondary metabolites: their function and evolution* (1992) Wiley Chichester (*Ciba Foundation Symposium* 171) p 88–112; Bibb, M. J. et al. *EMBO J.* (1989) 8:2727; Sherman, D. H. et al. *EMBO J.* (1989) 8:2717; Fernandez-Moreno, M. A. et al. *J. Biol. Chem.* (1992) 267:19278); Cortes, J. et al. *Nature* (1990) 348:176; Donadio, S. et al. *Science* (1991) 252:675; MacNeil, D. J. et al. *Gene* (1992) 115:119. Hybrid clusters are exemplified herein and are described further below. The genes included in the gene cluster need not be the native genes, but can be mutants or analogs thereof. Mutants or analogs may be prepared by the deletion, insertion or substitution of one or more nucleotides of the coding sequence. Techniques for modifying nucleotide sequences, such as site-directed mutagenesis, are described in, e.g., Sambrook et al., supra; *DNA Cloning*, Vols. I and II, supra; *Nucleic Acid Hybridization*, supra.

A "replacement PKS gene cluster" may also contain genes coding for modifications to the core polyketide catalyzed by the PKS, including, for example, genes encoding post-polyketide synthesis enzymes derived from natural products pathways such as 0-methyl-transferases and glycosyltransferases. A "replacement PKS gene cluster" may further include genes encoding hydroxylases, methylases or other alkylases, oxidases, reductases, glycotransferases, lyases, ester or amide synthases, and various hydrolases such as esterases and amidases.

As explained further below, the genes included in the replacement gene cluster need not be on the same plasmid or if present on the same plasmid, can be controlled by the same or different control sequences.

A "library" or "combinatorial library" of polyketides is intended to mean a collection of polyketides catalytically produced by a PKS gene cluster capable of catalyzing the synthesis of a polyketide. The library can be produced by a PKS gene cluster that contains any combination of native, homolog or mutant genes from aromatic, modular or fungal PKSs. The combination of genes can be derived from a single PKS gene cluster, e.g., act, fren, gra, tcm, whiE, gris, ery, or the like, and may optionally include genes encoding tailoring enzymes which are capable of catalyzing the further modification of a polyketide. Alternatively, the combination of genes can be rationally or stochastically derived from an assortment of PKS gene clusters, e.g. a minimal PKS gene cluster can be constructed to contain the KS/AT component from an act PKS, the CLF component from a tcm PKS and a ACP component from a fren PKS. The combination of genes can optionally include KR, CYC and ARO components of PKS gene clusters as well. The library of polyketides thus produced can be tested or screened for biological, pharmacological or other activity.

By "random assortment" is intended any combination and/or order of genes, homologs or mutants which encode for the various PKS enzymes, modules, active sites or portions thereof derived from aromatic, modular or fungal PKS gene clusters.

By "genetically engineered host cell" is meant a host cell where the native PKS gene cluster has been deleted using recombinant DNA techniques or host cell into which a heterologous PKS gene cluster has been inserted. Thus, the term would not encompass mutational events occurring in nature. A "host cell" is a cell derived from a procaryotic microorganism or a eucaryotic cell line cultured as a unicellular entity, which can be, or has been, used as a recipient for recombinant vectors bearing the PKS gene clusters of the invention. The term includes the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired PKS, are included in the definition, and are covered by the above terms.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention. Allelic variation or naturally occurring mutational events do not give rise to heterologous DNA, as used herein.

A "coding sequence" or a sequence which "encodes" a particular PKS, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. A transcription termination sequence will usually be located 3' to the coding sequence.

A "nucleic acid" sequence can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A transcription termination sequence will usually be located 3' to the coding sequence.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "selection marker" is meant any genetic marker which can be used to select a population of cells which carry the marker in their genome. Examples of selection markers include: auxotrophic markers by which cells are selected by their ability to grow on minimal media with or without a nutrient or supplement, e.g., thymidine, diaminopimelic acid or biotin; metabolic markers by which cells are selected for their ability to grow on minimal media containing the appropriate sugar as the sole carbon source or the ability of cells to form colored colonies containing the appropriate dyes or chromogenic substrates; and drug resistance markers by which cells are selected by their ability to grow on media containing one or more of the appropriate drugs, e.g., tetracycline, ampicillin, kanamycin, streptomycin or nalidixic acid.

"Recombination" is a the reassortment of sections of DNA sequences between two DNA molecules. "Homologous recombination" occurs between two DNA molecules which hybridize by virtue of homologous or complementary nucleotide sequences present in each DNA molecule.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms.

The term "alkylene" as used herein refers to a difunctional saturated branched or unbranched hydrocarbon chain containing from 1 to 24 carbon atoms, and includes, for example, methylene (—CH$_2$—), ethylene (—CH$_2$—CH$_2$—), propylene (—CH$_2$—CH$_2$—CH$_2$—), 2-methylpropylene [—CH$_2$-CH(CH$_3$)—CH$_2$—], hexylene [—(CH$_2$)$_6$—]and the like. "Lower alkylene" refers to an alkylene group of 1 to 6, more preferably 1 to 4, carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

"Halo" or "halogen" refers to fluoro, chloro, bromo or iodo, and usually relates to halo substitution for a hydrogen atom in an organic compound. Of the halos, chloro and fluoro are generally preferred.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

B. General Methods

Central to the present invention is the discovery of a host-vector system for the efficient recombinant production of both novel and known polyketides. In particular, the invention makes use of genetically engineered cells which have their naturally occurring PKS genes substantially deleted. These host cells can be transformed with recombinant vectors, encoding a variety of PKS gene clusters, for the production of active polyketides. The invention provides for the production of significant quantities of product at an appropriate stage of the growth cycle. The polyketides so produced can be used as therapeutic agents, to treat a number of disorders, depending on the type of polyketide in question. For example, several of the polyketides produced by the present method will find use as immunosuppressants, as anti-tumor agents, as well as for the treatment of viral, bacterial and parasitic infections. The ability to recombinantly produce polyketides also provides a powerful tool for characterizing PKSs and the mechanism of their actions.

More particularly, host cells for the recombinant production of the subject polyketides can be derived from any organism with the capability of harboring a recombinant PKS gene cluster. Thus, the host cells of the present invention can be derived from either procaryotic or eucaryotic organisms. However, preferred host cells are those constructed from the actinomycetes, a class of mycelial bacteria which are abundant producers of a number of polyketides. A particularly preferred genus for use with the present system is Streptomyces. Thus, for example, S. ambofaciens, S. avermitilis, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans, S. violaceoruber, among others, will provide convenient host cells for the subject invention, with S. coelicolor being preferred. (See, e.g., Hopwood, D. A. and Sherman, D. H. Ann. Rev. Genet. (1990) 24:37–66; O'Hagan, D. The Polyketide Metabolites (Ellis Horwood Limited, 1991), for a description of various polyketide-producing organisms and their natural products.)

The above-described cells are genetically engineered by deleting the naturally occurring PKS genes therefrom, using standard techniques, such as by homologous recombination. (See, e.g., Khosla, C. et al. Molec. Microbiol. (1992) 6:3237). Exemplified herein is a genetically engineered S. coelicolor host cell. Native strains of S. coelicolor produce a PKS which catalyzes the biosynthesis of the aromatic polyketide actinorhodin (structure 3, FIG. 5). The novel strain, S. coelicolor CH999 (as described in the examples), was constructed by deleting, via homologous recombination, the entire natural act cluster from the chromosome of S. coelicolor CH1 (FIG. 2) (Khosla, C. Molec. Microbiol. (1992) 6:3237), a strain lacking endogenous plasmids and carrying a stable mutation that blocks biosynthesis of another pigmented S. coelicolor antibiotic, undecylprodigiosin.

The host cells described above can be transformed with one or more vectors, collectively encoding a functional PKS set, or a cocktail comprising a random assortment of PKS genes, modules, active sites, or portions thereof. The vector (s) can include native or hybrid combinations of PKS subunits or cocktail components, or mutants thereof. As explained above, the replacement gene cluster need not correspond to the complete native gene cluster but need only encode the necessary PKS components to catalyze the production of a polyketide. For example, in each Streptomyces aromatic PKS so far studied, carbon chain assembly requires the products of three open reading frames (ORFs). ORF1 encodes a ketosynthase (KS) and an acyltransferase (AT) active site (KS/AT); as elucidated herein, ORF2 encodes a chain length determining factor (CLF), a protein similar to the ORF1 product but lacking the KS and AT motifs; and ORF3 encodes a discrete acyl carrier protein (ACP). Some gene clusters also code for a ketoreductase (KR) and a cyclase, involved in cyclization of the nascent polyketide backbone. (See FIGS. 1A and 1B for schematic representations of six PKS gene clusters.) However, it has been found that only the KS/AT, CLF, and ACP, need be present in order to produce an identifiable polyketide. Thus, in the case of aromatic PKSs derived from Streptomyces, these three genes, without the other components of the native clusters, can be included in one or more recombinant vectors, to constitute a "minimal" replacement PKS gene cluster.

Furthermore, the recombinant vector(s) can include genes from a single PKS gene cluster, or may comprise hybrid replacement PKS gene clusters with, e.g., a gene for one cluster replaced by the corresponding gene from another gene cluster. For example, it has been found that ACPs are readily interchangeable among different synthases without an effect on product structure. Furthermore, a given KR can recognize and reduce polyketide chains of different chain lengths. Accordingly, these genes are freely interchangeable in the constructs described herein. Thus, the replacement clusters of the present invention can be derived from any combination of PKS gene sets which ultimately function to produce an identifiable polyketide.

Examples of hybrid replacement clusters include clusters with genes derived from two or more of the act gene cluster, the whiE gene cluster, frenolicin (fren), granaticin (gra), tetracenomycin (tcm), 6-methylsalicylic acid (6-msas), oxytetracycline (otc), tetracycline (tet), erythromycin (ery), griseusin (gris), nanaomycin, medermycin, daunorubicin, tylosin, carbomycin, spiramycin, avermectin, monensin, nonactin, curamycin, rifamycin and candicidin synthase gene clusters, among others. (For a discussion of various PKSs, see, e.g., Hopwood, D. A. and Sherman, D. H. Ann. Rev. Genet. (1990) 24:37–66; O'Hagan, D. The Polyketide Metabolites (Ellis Horwood Limited, 1991).)

More particularly, a number of hybrid gene clusters have been constructed herein, having components derived from the act, fren, tcm, gris and gra gene clusters, as depicted in Tables 1, 2, 5 and 6. Several of the hybrid clusters were able to functionally express both novel and known polyketides in S. coelicolor CH999 (described above). However, other hybrid gene clusters, as described above, can easily be produced and screened using the disclosure herein, for the production of identifiable polyketides.

Furthermore, a library of randomly cloned ORF1, ORF2, ORF3 and homologs or mutant thereof, as well as other PKS genes and homologs or mutants thereof including ketoreductases, cyclases and aromatases from a collection of aromatic PKS gene clusters, could be constructed and screened for identifiable polyketides using methods described and exemplified herein. In addition, a considerable degree of variability exists for both the starter units (e.g., acetyl CoA, maloamyl CoA, propionyl CoA, acetate, butyrate, isobutyrate and the like) and the extender units among certain naturally occurring aromatic PKSs; thus, these units can also be used for obtaining novel polyketides via genetic engineering.

Additionally, a library of randomly cloned open reading frames or homologs from a collection of modular PKS gene clusters could be constructed and screened for identifiable polyketides. Such gene clusters are described in further detail below. Recombinant vectors can optionally include genes from an aromatic and a modular PKS gene cluster.

The recombinant vectors, harboring the gene clusters or random assortment of PKS genes, modules, active sites or portions thereof described above, can be conveniently generated using techniques known in the art. For example, the PKS subunits of interest can be obtained from an organism that expresses the same, using recombinant methods, such as by screening cDNA or genomic libraries, derived from cells expressing the gene, or by deriving the gene from a vector known to include the same. The gene can then be isolated and combined with other desired PKS subunits, using standard techniques. If the gene in question is already present in a suitable expression vector, it can be combined in situ, with, e.g., other PKS subunits, as desired. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence can be assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Mutations can be made to the native PKS subunit sequences and such mutants used in place of the native sequence, so long as the mutants are able to function with other PKS subunits to collectively catalyze the synthesis of an identifiable polyketide. Such mutations can be made to the native sequences using conventional techniques such as by preparing synthetic oligonucleotides including the mutations and inserting the mutated sequence into the gene encoding a PKS subunit using restriction endonuclease digestion. (See, e.g., Kunkel, T. A. *Proc. Natl. Acad. Sci. USA* (1985) 82:448; Geisselsoder et al. *BioTechniques* (1987) 5:786.) Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409. PCR mutagenesis will also find use for effecting the desired mutations.

Random mutagenesis of the nucleotide sequences obtained as described above can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

Large populations of random enzyme variants can be constructed in vivo using "recombination-enhanced mutagenesis." This method employs two or more pools of, for example, $10^6$ mutants each of the wild-type encoding nucleotide sequence that are generated using any convenient mutagenesis technique, described more fully above, and then inserted into cloning vectors.

Once the mutant sequences are generated, the DNA is inserted into an appropriate cloning vector, using techniques well known in the art (see, e.g., Sambrook et al., supra). The choice of vector depends on the pool of mutant sequences, i.e., donor or recipient, with which they are to be employed. Furthermore, the choice of vector determines the host cell to be employed in subsequent steps of the claimed method. Any transducible cloning vector can be used as a cloning vector for the donor pool of mutants. It is preferred, however, that phagemids, cosmids, or similar cloning vectors be used for cloning the donor pool of mutant encoding nucleotide sequences into the host cell. Phagemids and cosmids, for example, are advantageous vectors due to the ability to insert and stably propagate therein larger fragments of DNA than in M13 phage and λ phage, respectively. Phagemids which will find use in this method generally include hybrids between plasmids and filamentous phage cloning vehicles. Cosmids which will find use in this method generally include λ phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., supra). The utility of employing such vectors having different marker genes may be exploited to facilitate a determination of successful transduction.

Thus, for example, the cloning vector employed may be a phagemid and the host cell may be *E. coli*. Upon infection of the host cell which contains a phagemid, single-stranded phagemid DNA is produced, packaged and extruded from the cell in the form of a transducing phage in a manner similar to other phage vectors. Thus, clonal amplification of mutant encoding nucleotide sequences carried by phagemids is accomplished by propagating the phagemids in a suitable host cell.

Following clonal amplification, the cloned donor pool of mutants is infected with a helper phage to obtain a mixture of phage particles containing either the helper phage genome or phagemids mutant alleles of the wild-type encoding nucleotide sequence.

Infection, or transfection, of host cells with helper phage is generally accomplished by methods well known in the art (see, e.g., Sambrook et al., supra; and Russell et al. (1986) *Gene* 45:333–338).

The helper phage may be any phage which can be used in combination with the cloning phage to produce an infective transducing phage. For example, if the cloning vector is a cosmid, the helper phage will necessarily be a λ phage. Preferably, the cloning vector is a phagemid and the helper phage is a filamentous phage, and preferably phage M13.

If desired after infecting the phagemid with helper phage and obtaining a mixture of phage particles, the transducing phage can be separated from helper phage based on size differences (Barnes et al. (1983) *Methods Enzymol.* 101:98–122), or other similarly effective technique.

The entire spectrum of cloned donor mutations can now be transduced into clonally amplified recipient cells into which has been transduced or transformed a pool of mutant encoding nucleotide sequences. Recipient cells which may be employed in the method disclosed and claimed herein may be, for example, *E. coli*, or other bacterial expression systems which are not recombination deficient. A recombination deficient cell is a cell in which recombinatorial events is greatly reduced, such as the rec⁻ mutants of *E. coli* (see, Clark et al. (1965) *Proc. Natl. Acad. Sci. USA* 53:451–459).

By maintaining a high multiplicity of infection (MOI) and a ratio of [transductant forming units (tfu)]: [plaque forming units (pfu)]greater than 1, one can insure that virtually every recipient cell receives at least one mutant gene from the donor pool. The MOI is adjusted by manipulating the ratio of transducing particles to cell density. By the term "high multiplicity of infection" is meant a multiplicity of infection of greater than 1, preferably between 1 to 100, more preferably between 1 and 10.

It is preferred that the tfu:pfu ratio, as reflecting the ratio of transducing phages to helper phages, be as large as possible, at least greater than one, more preferably greater than 100 or more. By exercising the option to separate transducing phage from helper phage, as described above, the tfu:pfu ratio can be maximized.

These transductants can now be selected for the desired expressed protein property or characteristic and, if necessary or desirable, amplified. Optionally, if the phagemids into which each pool of mutants is cloned are constructed to express different genetic markers, as described above, transductants may be selected by way of their expression of both donor and recipient plasmid markers.

The recombinants generated by the above-described methods can then be subjected to selection or screening by any appropriate method, for example, enzymatic or other biological activity.

The above cycle of amplification, infection, transduction, and recombination may be repeated any number of times using additional donor pools cloned on phagemids. As above, the phagemids into which each pool of mutants is cloned may be constructed to express a different marker gene. Each cycle could increase the number of distinct mutants by up to a factor of $10^6$. Thus, if the probability of occurrence of an inter-allelic recombination event in any individual cell is f (a parameter that is actually a function of the distance between the recombining mutations), the transduced culture from two pools of $10^6$ allelic mutants will express up to $10^{12}$ distinct mutants in a population of $10^{12}$/f cells.

The gene sequences, native or mutant, which collectively encode a replacement PKS gene cluster, can be inserted into one or more expression vectors, using methods known to those of skill in the art. In order to incorporate a random assortment of PKS genes, modules, active sites or portions thereof into am expression vector, a cocktail of same can be prepared and used to generate the expression vector by techniques well known in the art and described in detail below. Expression vectors will include control sequences operably linked to the desired PKS coding sequence. Suitable expression systems for use with the present invention include systems which function in eucaryotic and procaryotic host cells. However, as explained above, procaryotic systems are preferred, and in particular, systems compatible with Streptomyces spp. are of particular interest. Control elements for use in such systems include promoters, optionally containing operator sequences, and ribosome binding sites. Particularly useful promoters include control sequences derived from PKS gene clusters which result in the production of polyketides as secondary metabolites, such as one or more act promoters, tcm promoters, spiramycin promoters, and the like. However, other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the β-lactamase (bla) promoter system, bacteriophage lambda PL, and T5. In addition, synthetic promoters, such as the tac promoter (U.S. Pat. No. 4,551,433), which do not occur in nature also function in bacterial host cells.

Other regulatory sequences may also be desirable which allow for regulation of expression of the PKS replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for selecting cells successfully transformed by the present constructs.

The various PKS subunits of interest, or the cocktail of PKS genes, modules, active sites, or portions thereof, can be cloned into one or more recombinant vectors as individual cassettes, with separate control elements, or under the control of, e.g., a single promoter. The PKS subunits or cocktail components can include flanking restriction sites to allow for the easy deletion and insertion of other PKS subunits or cocktail components so that hybrid PKSs can be generated. The design of such unique restriction sites is known to those of skill in the art and can be accomplished using the techniques described above, such as site-directed mutagenesis and PCR.

Using these techniques, a novel plasmid, pRM5, (FIG. 3 and Example 2) was constructed as a shuttle vector for the production of the polyketides described herein. Plasmid pRM5 includes the act genes encoding the KS/AT (ORF1), CLF (ORF2) and ACP (ORF3) PKS subunits, flanked by PacI, NsiI and XbaI restriction sites. Thus, analogous PKS subunits, encoded by other PKS genes, can be easily substituted for the existing act genes. (See, e.g., Example 4, describing the construction of hybrid vectors using pRM5 as the parent plasmid). The shuttle plasmid also contains the act KR gene (actIII), the cyclase gene (actVII), and a putative dehydratase gene (actIV), as well as a ColEI replicon (to allow transformation of *E. coli*), an appropriately truncated SCP2* (low copy number) Streptomyces replicon, and the actII-ORF4 activator gene from the act cluster, which induces transcription from act promoters during the transition from growth phase to stationary phase in the vegetative mycelium. pRM5 carries the divergent actI/actIII promoter pair.

Methods for introducing the recombinant vectors of the present invention into suitable hosts are known to those of skill in the art and typically include the use of $CaCl_2$ or other agents, such as divalent cations and DMSO. DNA can also be introduced into bacterial cells by electroporation. Once the PKSs are expressed, the polyketide producing colonies can be identified and isolated using known techniques. The produced polyketides can then be further characterized.

Figure 9:
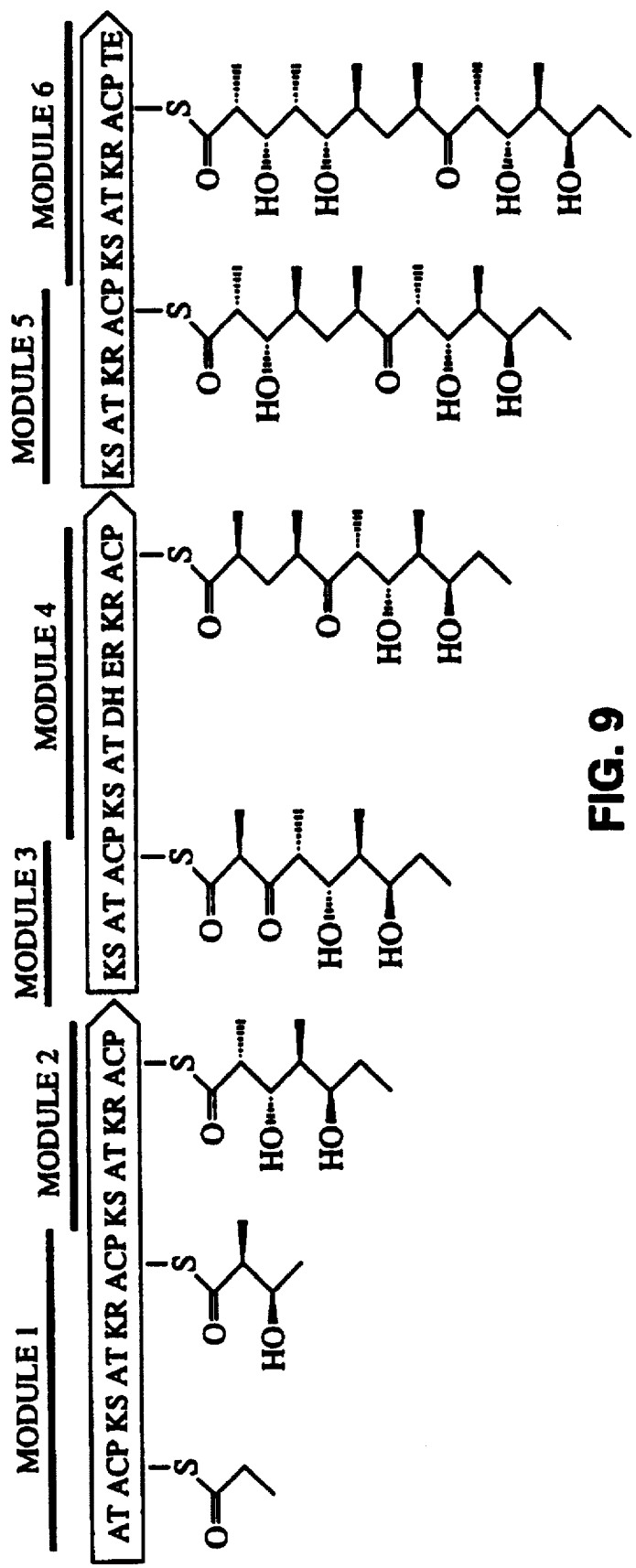
FIG. 9 depicts the genetic model for the 6-deoxyerythronolide B synthase (DEBS).

As explained above, the above-described recombinant methods also find utility in the catalytic biosynthesis of polyketides by large, modular PKSs. For example, 6-deoxyerythronolide B synthase (DEBS) catalyzes the biosynthesis of the erythromycin aglycone, 6-deoxyerythronolide B (17). Three open reading frames (eryAI, eryAII, and eryAIII) encode the DEBS polypeptides and span 32 kb in the ery gene cluster of the Saccharopolyspora erythraea genome. The genes are organized in six repeated units, each designated a "module." Each module encodes a set of active sites that, during polyketide biosynthesis, catalyzes the condensation of an additional monomer onto the growing chain. Each module includes an acyltransferase (AT), β-ketoacyl carrier protein synthase (KS), and acyl carrier protein (ACP) as well as a subset of reductive active sites (β-ketoreductase (KR), dehydratase (DH), enoyl reductase (ER)) (FIG. 9). The number of reductive sites within a module corresponds to the extent of β-keto reduction in each condensation cycle. The thioesterase (TE) encoded at the end of module appears to catalyze lactone formation.

Due to the large sizes of eryAI, eryAII, and eryAIII, and the presence of multiple active sites, these genes can be conveniently cloned into a plasmid suitable for expression in a genetically engineered host cell, such as CH999, using an in vivo recombination technique. This technique, described in Example 7 and summarized in FIG. 10, utilizes derivatives of the plasmid pMAK705 (Hamilton et al. (1989) *J. Bacteriol.* 171:4617) to permit in vivo recombination between a temperature-sensitive donor plasmid, which is capable of replication at a first, permissive temperature and incapable of replication at a second, non-permissive temperature, and recipient plasmid. The eryA genes thus cloned gave pCK7, a derivative of pRM5 (McDaniel et al. (1993) *Science* 262:1546). A control plasmid, pCK7f, was constructed to carry a frameshift mutation in eryAI. pCK7 and pCK7f possess a ColEI replicon for genetic manipulation in *E. coli* as well as a truncated SCP2* (low copy number) Streptomyces replicon. These plasmids also contain the divergent actI/actIII promoter pair and actII-ORF4, an activator gene, which is required for transcription from these promoters and activates expression during the transition from growth to stationary phase in the vegetative mycelium. High-level expression of PKS genes occurs at the onset of stationary phase of mycelial growth; the recombinant strains therefore produce "reporter" polyketides as secondary metabolites in a quasi-natural manner.

Recombinant vectors harboring modular PKSs can also be generated using techniques known in the art. For example, the PKS of interest can be obtained from an organism that expresses the same using recombinant techniques as describe above and exemplified in Examples 7 and 8. For example, the gene can be isolated, subjected to mutation-producing protocols and reexpressed (see Example 8).

The method described above for producing polyketides synthesized by large, modular PKSs may be used to produce other polyketides as secondary metabolites such as sugars, β-lactams, fatty acids, aminoglycosides, terpinoids, non-ribosomal peptides, prostanoid hormones and the like. In this manner, the polyketides can be produced after the host cell has matured, thereby reducing any potential toxic or other bioactive effects of the polyketide on the host cell.

As with aromatic (Type II) and modular (Type I) PKSs, the above described methods also find utility in the catalytic biosynthesis of polyketides using the PKS genes from fungi. Fungal PKSs, such as the 6-methylsalicylic acid PKS consist of a single multi-domain polypeptide which includes all active sites required for the biosynthesis of 6-methylsalicylic acid.

Using the above recombinant methods, a number of polyketides have been produced. These compounds have the general structure (I)

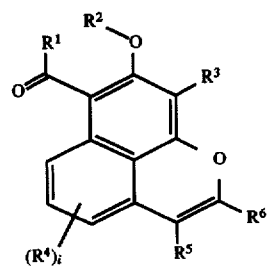

wherein $R^1$, $R^2$, $R^3$, $R^4$, $R^5$, $R^6$, $R^7$, $R^8$ and i are as defined above. One group of such compounds are wherein: $R^1$ is lower alkyl, preferably methyl; $R^2$, $R^3$ and $R^6$ are hydrogen; $R^6$ is —$CHR^7$—(CO)—$R^8$; and i is 0. A second group of such compounds are wherein: $R^1$ and $R^6$ are lower alkyl, preferably methyl; $R^2$, $R^3$ and $R^5$ are hydrogen; and i is 0. Still a third group of such compounds are wherein: $R^1$ and $R^2$ are linked together to form a lower alkylene bridge —$CHR^9$—$CHR^{10}$ wherein $R^9$ and $R^{10}$ are independently selected from the group consisting of hydrogen, hydroxyl and lower alkyl, e.g., —$CH^2$—CHOH—; $R^3$ and $R^5$ are hydrogen; $R^6$ is —$CHR^7$—(CO)—$R^8$ where $R^8$ is hydrogen or lower alkyl, e.g., —$CH^2$—(CO)—$CH^3$; and i is 0. Specific such compounds include the following compounds 9, 10 and 11 as follows:

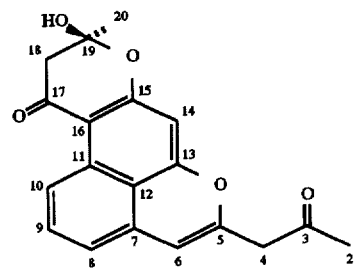

9

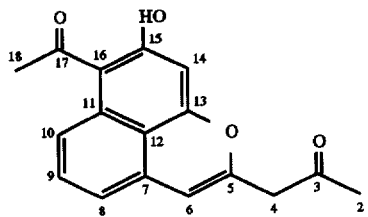

10

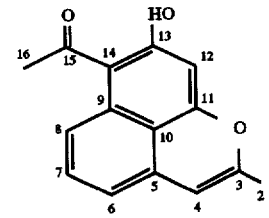

11

Other novel polyketides within the scope of the invention are those having the structure

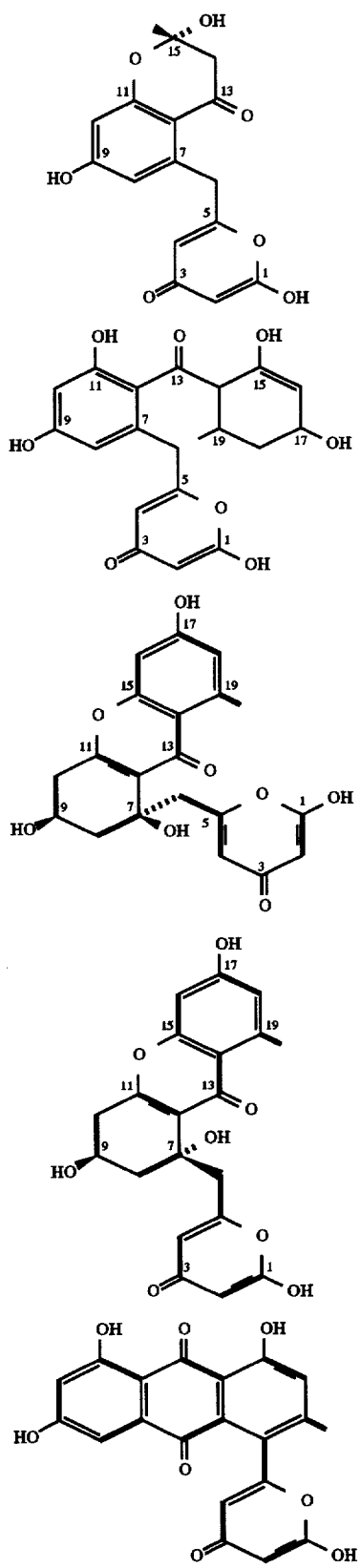

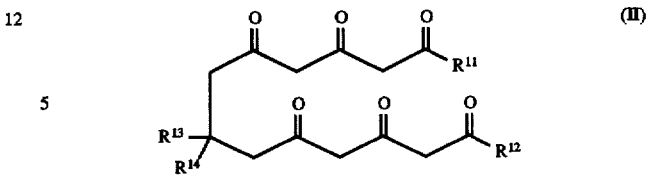

wherein $R^{11}$, $R^{12}$, $R^{13}$ and $R^{14}$ and E are as defined earlier herein. Examples of such compounds include: a first group wherein $R^{11}$ is methyl and $R^{12}$ is —$CH_2(CO)$—S—E; a second group wherein $R^{11}$ is —$CH_2(CO)CH_3$ and $R^{12}$ is —S—E; a third group wherein $R^{11}$ is —$CH_2(CO)CH_3$ and $R^{12}$ is -$CH_2$ (CO)—S—E; and a fourth group wherein $R^{11}$ is -$CH_2$ (CO)$CH_2$ (CO)$CH_3$ and $R^{12}$ is —$CH_2(CO)$—S—E (see FIG. 8 for structural exemplification).

The remaining structures encompassed by generic formula (I)—i.e., structures other than 9, 10 and 11—may be prepared from structures 9, 10 or 11 using routine synthetic organic methods well-known to those skilled in the art of organic chemistry, e.g., as described by H. O. House, *Modern Synthetic Reactions*, Second Edition (Menlo Park, Calf.: The Benjamin/Cummings Publishing Company, 1972), or by J. March, *Advanced Organic Chemistry: Reactions, Mechanisms and Structure*, 4th Ed. (New York: Wiley-Interscience, 1992), the disclosures of which are hereby incorporated by reference. Typically, as will be appreciated by those skilled in the art, incorporation of substituents on the aromatic rings will involve simple electrophilic aromatic addition reactions. Structures 12 and 13 may be modified in a similar manner to produce polyketides which are also intended to be within the scope of the present invention.

In addition, the above recombinant methods have been used to produce polyketide compound having the general structure (III)

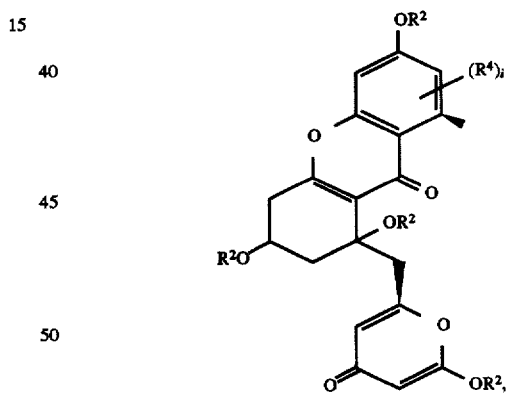

general structure (IV)

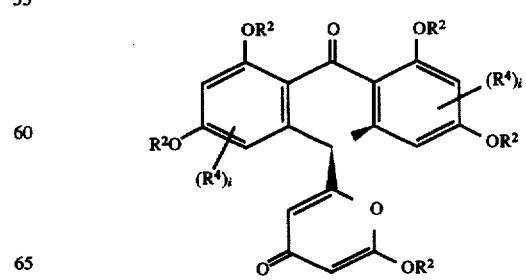

Preparation of compounds 9, 10, 11, 12, 13, 14, 15 and 16 is effected by cyclization of an enzyme-bound polyketide having the structure (II)

and general structure (V)

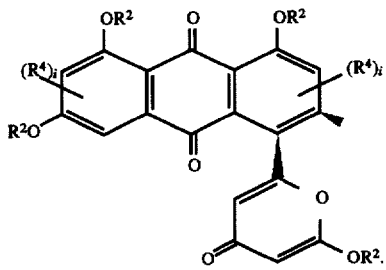

Particularly preferred compounds of structural formulas (III), (IV) and (V) are wherein: $R^2$ is hydrogen and i is 0.

As disclosed hereinabove and in the Examples which follow, a system has been developed to functionally express recombinant PKSs and to produce novel aromatic polyketides (Examples 1–6). This technology has been extrapolated to larger gene clusters using an in vivo recombination strategy (Kao et al. *Science* (1994) 265:509–512; see Examples 7 and 8). These systems may be used to genetically manipulate polyketide biosynthesis to generate libraries of synthetic products.

Figure 10:
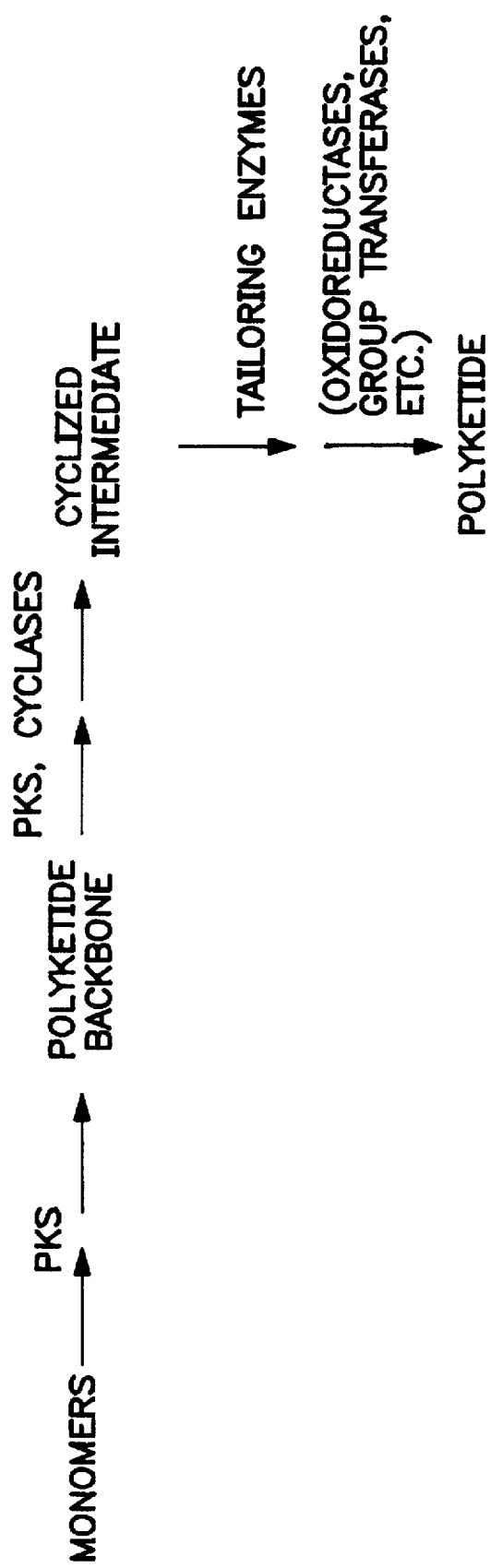
FIG. 10 is a representation of the overall biosynthetic pathway for a typical polyketide natural product.

A typical pathway for polyketide biosynthesis is shown in FIG. 10. Generally, polyketide synthesis occurs in three stages. In the first stage, catalyzed by the PKS, a nascent polyketide backbone is generated from monomeric CoA thioesters. In the second stage this backbone is regiospecifically cyclized. While some cyclization reactions are controlled by the PKS itself, others result from activities of downstream enzymes. In the final stage, the cyclized intermediate is modified further by the action of mechanistically diverse "tailoring enzymes," giving rise to the natural product.

More particularly, polyketide biosynthesis begins with a primer unit loading on to the active site of the condensing enzyme, β-keto acyl synthase (KS). An extender unit (usually malonate) is then transferred to the pathetheinyl arm of the acyl carrier protein (ACP). The KS catalyzes the condensation between the ACP-bound malonate and the starter unit. Additional extender units are added sequentially until the nascent polyketide chain has grown to a desired chain length determined by the protein chain length factor (CLF), perhaps together with the KS. Thus, the KS, CLF and the ACP form a minimal set to generate a polyketide backbone, and are together called the "minimal PKS." The nascent polyketide chain is then subjected to regiospecific ketoreduction by a ketoreductase (KR) if it exists. Cyclases (CYC) and aromatases (ARO) later catalyze regiospecific ring formation events through intramolecular aldol condensations. The cyclized intermediate may then undergo additional regiospecific and/or stereospecific modifications (e.g., O-methylation, hydroxylation, glycosylation, etc.) controlled by downstream tailoring enzymes).

Figure 11B:
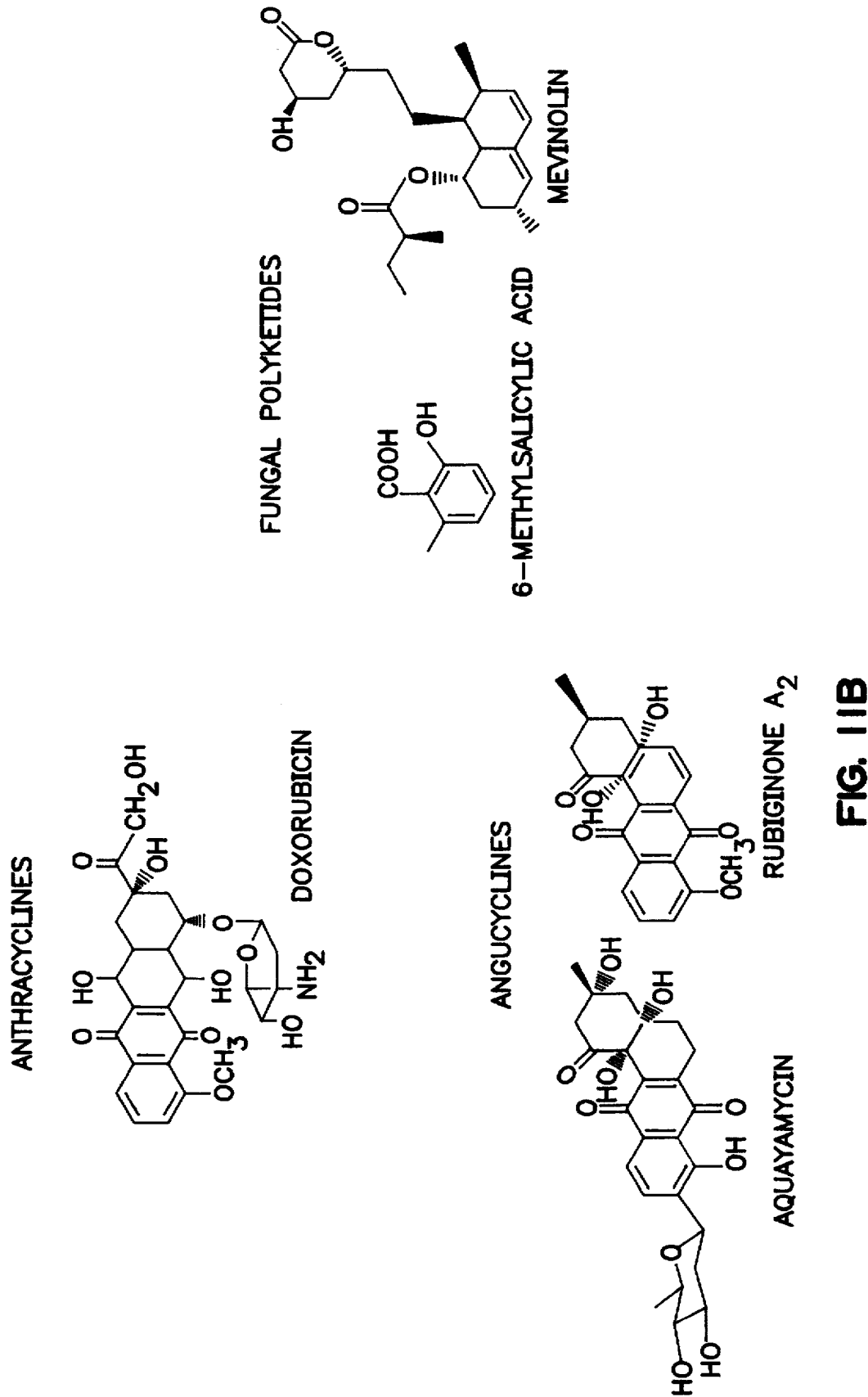
FIG. 11 shows the structures of various polyketide of aromatic, modular and fungal PKSs.

Acetyl CoA is the usual starter unit for most aromatic polyketides. However, maloamyl CoA (Gatenbeck, *S. Biochem. Biophy. Res. Commun.* (1961) 6:422–426) and propionyl CoA (Paulick, R. C. et al. *J. Am. Chem. Soc.* (1976) 98:3370–3371) are primers for many members of the tetracycline and anthracycline classes of polyketides, respectively (FIG. 11). Daunorubicin PKS can also accept acetate, butyrate, and isobutyrate as starter units. (Oki, T. et al. *J. Antibiot.* (1981) 34:783–790; Yoshimoto, A. et al. *J. Antiobiot.* (1993) 46:1758–1761).

The act KR can productively interact with all minimal PKSs studied thus far and is both necessary and sufficient to catalyze a C-9 ketoreduction. Although homologous KRs have been found in other PKS clusters, they catalyze ketoreduction with the same regiospecificity. However, the structures of frenolicin, griseusin and daunorubicin (FIG. 11) suggest that an additional C-17 ketoreduction occurs in these biosynthetic pathways. Likewise, several angucyclines undergo a C-15 ketoreduction, which occurs before the nascent polyketide chain is cyclized (Gould, S. J. et al. *J. Am. Chem. Soc.* (1992) 114:10066–10068). The ketoreductases responsible for C-15 and C-17 reductions have not yet been identified; however, two homologous KRs have been found in the daunorubicin PKS cluster (Grimm, A. et al. *Gene* (1994) 151:1–10; Ye, J. et al. *J. Bacteriol.* (1994) 176:6270–6280). It is likely that they catalyze the C-9 and C-17 reductions. Thus, KRs responsible for regiospecific reduction of the carbon chain backbone at positions other than C-9 may also be targets for use in the construction of combinatorial libraries.

The formation of the first two six-membered rings in the biosynthesis of most naturally occurring bacterial aromatic polyketides is controlled by PKS subunits; further ring closures are controlled by additional cyclases and modifying enzymes. The structural diversity introduced via these reactions appears to be greater than via the first two cyclizations. However, certain preferred patterns are observed, which suggests that at least some of these downstream cyclases may be useful for the construction of combinatorial libraries. For example, the pyran ring in isochromanequinones (FIG. 11) is invariably formed via cyclization between C-3 and C-15; two stereochemically distinct classes of products are observed (see, for example, the structures of actinorhodin and frenolicin in (FIG. 11)). In anthracyclines and tetracyclines a third aldol condensation usually occurs between C-3 and C-16, whereas in unreduced tetracenomycins (FIG. 11) and related compounds it occurs between C-5 and C-18, and in angucyclines (FIG. 11) it occurs between C-4 and C-17. Representative gene(s) encoding a few of these enzymes have already been cloned (Fernandez-Moreno, M. A., et al. *J. Biol. Chem.* (1994) 269:24854–24863; Shen, B. et al. *Biochemistry* (1993) 32:11149–11154). At least some cyclases might recognize chains of altered lengths and/or degrees of reduction, thereby increasing the diversity of aromatic polyketide combinatorial libraries.

In the absence of downstream cyclases, polyketide chains undergo non-enzymatic reactions. Recently, some degree of predictability has emerged within this repertoire of possibilities. For instance, hemiketals and benzene rings are two common moieties seen on the methyl end. Hemiketals are formed with an appropriately-positioned enol and can be followed by a dehydration. Benzene rings are formed with longer uncyclized methyl terminus. On the carboxyl terminus, a γ-pyrone ring formed by three ketide units is frequently observed. Spontaneous decarboxylations occur on free carboxyl ends activated by the existence of a β-carbonyl.

A cyclized intermediate can undergo various types of modifications to generate the final natural product. The recurrence of certain structural motifs among naturally occurring aromatic polyketides suggests that some tailoring enzymes, particularly group transferases, may be combinatorially useful. Two examples are discussed below.

O-methylation is a common downstream modification. Although several SAM-dependent O-methyltransferase genes have been found in PKS gene clusters (Decker, H. et al. *J. Bacteriol.* (1993) 175:3876–3886), their specificities have not been systematically studied as yet. Perhaps some of them could be useful for combinatorial biosynthesis. For instance, O-11-methylation occurs in several members of the anthracycline, tetracenomycin, and angucycline classes of aromatic polyketides (FIG. 11).

Both aromatic and complex polyketides are often glycosylated. In many cases (e.g. doxorubicin and erythromycin) absence of the sugar group(s) results in considerably weaker bioactivity. There is tremendous diversity in both the types and numbers of sugar units attached to naturally occurring polyketide aglycones. In particular, deoxy- and aminosugars are commonly found. Regiochemical preferences can be detected in many glycosylated natural products. Among anthracyclines, O-17 is frequently glycosylated, whereas among angucyclines, C-10 is usually glycosylated. Glycosyltransferases involved in erythromycin biosynthesis may have relaxed specificities for the aglycone moiety (Donadio, S. et al. *Science* (1991) 252:675–679). An elloramycin glycosyltransferase may be able to recognize an unnatural NDP-sugar unit and attach it regiospecifically to an aromatic polyketide aglycone (Decker, H. et al. *Angew. Chem.* (1995), in press). These early results suggest that glycosyltransferases derived from secondary metabolic pathways have unique properties and may be attractive targets for use in the generation of combinatorial libraries.

Although modular PKSs have not been extensively analyzed, the one-to-one correspondence between active sites and product structure (FIG. 9), together with the incredible chemical diversity observed among naturally occurring "complex" polyketides, indicates that the combinatorial potential within these multienzyme systems could be considerably greater than that for aromatic PKSs. For example, a wider range of primer units including aliphatic monomers (acetate, propionate, butyrate, isovalerate, etc.), aromatics (aminohydroxybenzoic acid), alicyclics (cyclohexanoic acid), and heterocyclics (pipecolic acid) are found in various macrocyclic polyketides. Recent studies have shown that modular PKSs have relaxed specificity for their starter units (Kao et al. *Science* (1994), supra). The degree of β-ketoreduction following a condensation reaction can also be altered by genetic manipulation (Donadio et al. *Science* (1991), supra; Donadio, S. et al. *Proc. Natl. Acad. Sci. USA* (1993) 90:7119–7123). Likewise, the size of the polyketide product can be varied by designing mutants with the appropriate number of modules (Kao, C. M. et al. *J. Am. Chem. Soc.* (1994) 116:11612–11613). Modular PKSs also exhibit considerable variety with regards to the choice of extender units in each condensation cycle, although it remains to be seen to what extent this property can be manipulated. Lastly, these enzymes are particularly well-known for generating an impressive range of asymmetric centers in their products in a highly controlled manner. Thus, the combinatorial potential within modular PKS pathways could be virtually unlimited.

Like the actinomycetes, filamentous fungi are a rich source of polyketide natural products. The fact that fungal PKSs, such as the 6-methylsalicylic acid synthase (6-MSAS) and the mevinolin synthase, are encoded by single multi-domain proteins (Beck et al. *Eur. J. Biochem.* (1990), supra; Davis, R. et al. *Abstr. Genet. Ind. Microorg. Meeting*, supra) indicates that they may also be targeted for combinatorial mutagenesis. Moreover, fungal PKSs can be functionally expressed in *S. coelicolor* CH999 using the genetic strategy outlined above. Chain lengths not observed in bacterial aromatic polyketides (e.g. tetraketides, pentaketides and hexaketides) have been found among fungal aromatic polyketides (O'Hagan, D. *The Polyketide Metabolites* (Ellis Horwood, Chichester, U. K., 1991). Likewise, the cyclization patterns of fungal aromatic polyketides are quite different from those observed in bacterial aromatic polyketides (Id.). In contrast with modular PKSs from bacteria, branched methyl groups are introduced into fungal polyketide backbones by S-adenosylmethioninedependent methyltransferases; in the case of the mevinolin PKS (Davis, R. et al. *Abstr. Genet. Ind. Microorg. Meeting*, supra), this activity is encoded as one domain within a monocistronic PKS. It is now possible to experimentally evaluate whether these and other sources of chemical diversity in fungal polyketides are indeed amenable to combinatorial manipulation.

Based on the above-discussed state of the art, and the results presented in Examples 1–8 hereinbelow, the inventors herein have developed the following set of design rules for rationally or stochastically manipulating early biosynthetic steps in aromatic polyketide pathways including chain synthesis, C-9 ketoreduction, and the formation of the first two aromatic rings. If each biosynthetic degree of freedom was independent of all others, then it should be possible to design a single combinatorial library of $N_1 \times N_2 \times \ldots N_i \times \ldots N_{n-1} \times N_n$ clones, where $N_i$ is the number of ways in which the ith degree of freedom can be exploited. In practice however, not all enzymatic degrees of freedom are independent. Therefore, to minimize redundancy, it is preferable to design several sub-libraries of aromatic polyketide-producing clones.

Figure 12:
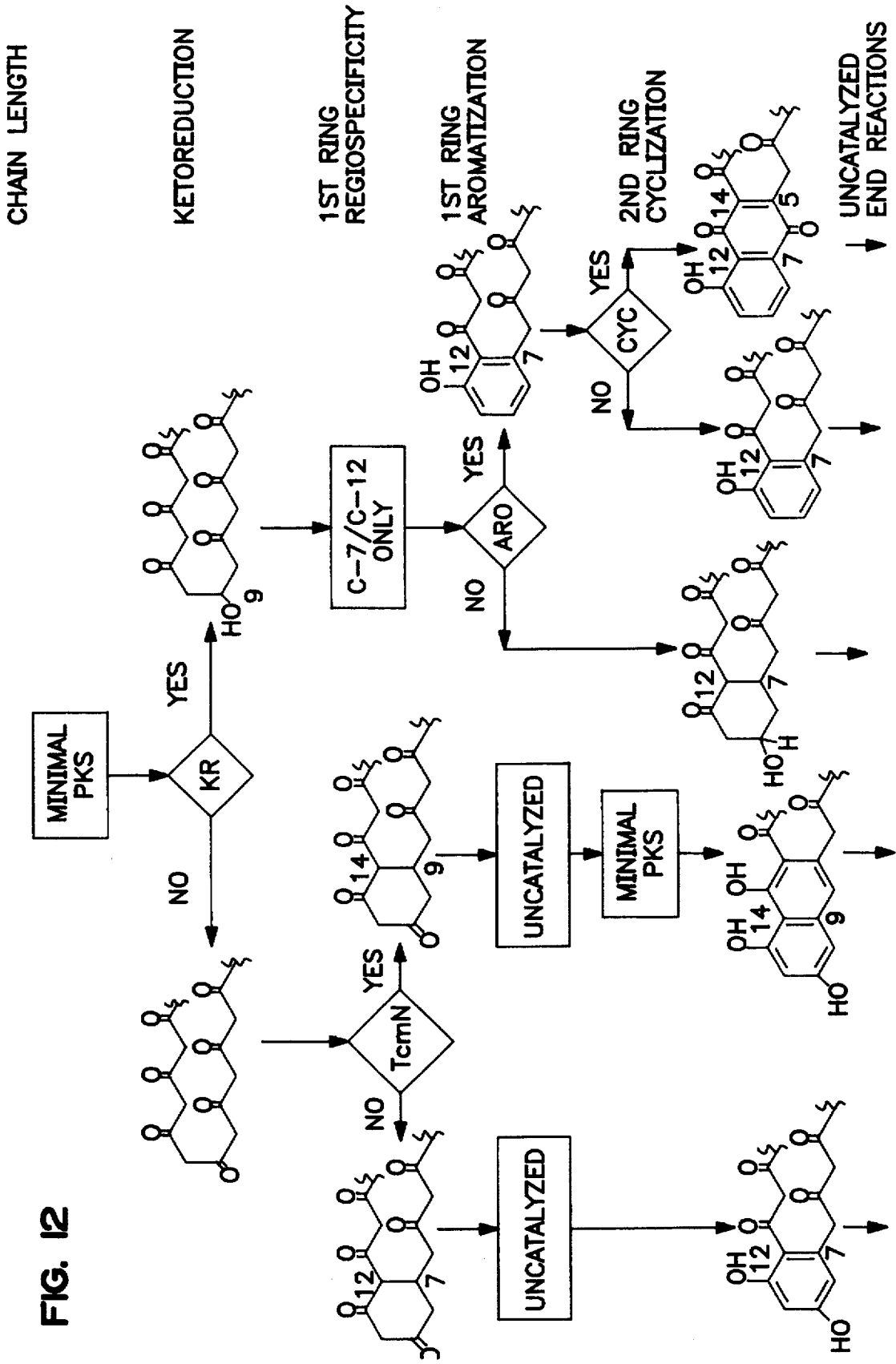
FIG. 12 is a scheme for rationally engineered biosynthesis of polyketides.

(1) Chain length. Polyketide carbon chain length is dictated by the minimal PKS (FIG. 12). Within the minimal PKS, the acyl carrier protein can be interchanged without affecting specificity, whereas the chain length factor is crucial. Although some ketosynthase/chain length factor combinations are functional, others are not; therefore, biosynthesis of a polyketide chain of specified length can be insured with a minimal PKS in which both the ketosynthase and chain length factor originate from the same PKS gene cluster. So far, chain lengths of 16 (octaketide), 18 (nonaketide), 20 (decaketide), and 24 carbons (dodecaketide) can be generated with minimal PKSs from the act, fren, tcm, and, whiE PKS clusters, respectively (McDaniel et al. *Science* (1993), supra; McDaniel et al. *J. Am. Chem. Soc.* (1993), supra; McDaniel et al. *Proc. Natl. Acad. Sci. USA* (1994), supra). The whiE minimal PKS can also generate 22-carbon backbones in the presence of a KR, suggesting a degree of relaxed chain length control as found for the fren PKS.

(2) Ketoreduction. Ketoreduction requires a ketoreductase (FIG. 12). The act KR can catalyze reduction of the C-9 carbonyl (counting from the carboxyl end) of a nascent polyketide backbone of any length studied so far. Furthermore, the act KR is compatible with all the minimal PKSs mentioned above. Homologous ketoreductases have been identified in other PKS clusters (Sherman, D. H., et al. *EMBO J.* (1989) 8:2717–2725; Yu, T.-W. et al. *J. Bacteriol.* (1994) 176:2627–2534; Bibb, M. J. et al. *Gene* (1994) 142:31–39). These enzymes may catalyze ketoreduction at C-9 as well since all the corresponding natural products undergo this modification. In unusual circumstances, C-7 ketoreductions have also been observed with the act KR.

(3) Cyclization of the first ring. Although the minimal PKS alone can control formation of the first ring, the regiospecific course of this reaction may be influenced by other PKS proteins. For example, most minimal PKSs studied so far produce polyketides with C-7/C-12 cyclizations when present alone (FIG. 12). In contrast, the tcm minimal PKS alone generates both C-7/C-12 and C-9/C-14 cyclized products. The presence of a ketoreductase with any minimal PKS restricts the nascent polyketide chain to cyclize exclusively with respect to the position of ketoreduction: C-7/C-12 cyclization for C-9 ketoreduction and C-5/C-10 cyclization for C-7 ketoreduction (McDaniel, R. et al. *J. Am. Chem. Soc.* (1993) 115:11671–11675; McDaniel, R. et al. *Proc. Natl. Acad. Sci. USA* (1994) 91:11542–11546; McDaniel, R. et al. *J. Am. Chem. Soc.* (1994) 116:10855–10859). Likewise, use of the TcmN enzyme alters the regiospecificity to C-9/C-14 cyclizations for unreduced polyketides of different lengths, but has no effect on reduced molecules (see Example 5 below).

(4) First ring aromatization. The first ring in unreduced polyketides aromatizes non-catalytically. In contrast, an aromatizing subunit is required for reduced polyketides (FIG. 12). There appears to be a hierarchy in the chain length specificity of these subunits from different PKS clusters. For example, the act ARO will recognize only 16-carbon chains (McDaniel et al. *Proc. Natl. Acad. Sci. USA* (1994), supra), the fren ARO recognizes both 16- and 18-carbon chains, while the gris ARO recognizes chains of 16, 18, and 20 carbons.

(5) Second ring cyclization. C-5/C-14 cyclization of the second ring of reduced polyketides may be achieved with an appropriate cyclase (FIG. 12). While the act CYC can cyclize octa- and nonaketides, it does not recognize longer chains. No equivalent C-5/C-14 cyclase with specificity for decaketides or longer chains has been identified, although the structures of natural products such as griseusin imply their existence. In the case of sufficiently long unreduced chains with a C-7/C-16 first ring, formation of a C-7/C-16 second ring is catalyzed by the minimal PKS (FIG. 12) (McDaniel et al. *Proc. Natl. Acad. Sci. USA* (1994), supra).

Figure 13A:
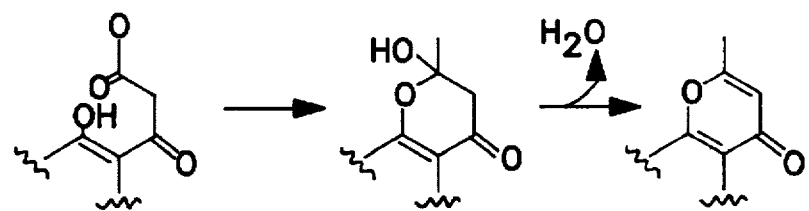
FIG. 13 shows the common moieties observed in engineered polyketides formed by non-enzymatic reactions involving the uncyclized portions of the carbon chain. Hemiketals (a) and benzene rings (b) are formed at the methyl ends, whereas γ-pyrone rings (c) and decarboxylations (d) occur at the carboxyl ends. The two chain ends can also co-cyclize via aldol condensations (e).
Figure 13B:
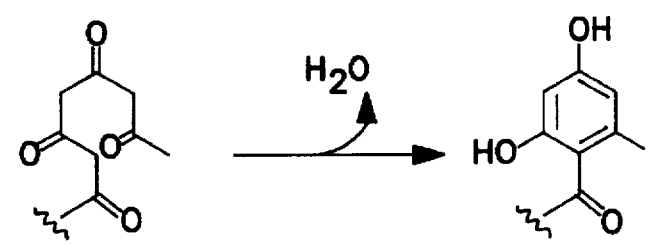
Figure 13C:
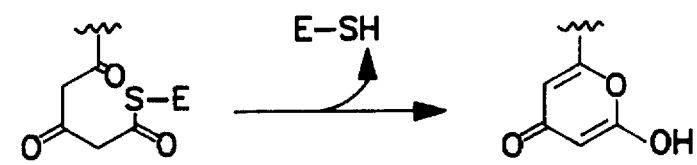
Figure 13D:
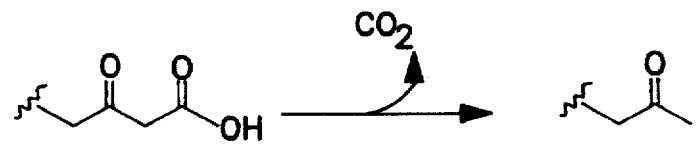

(6) Additional cyclizations. The KS, CLF, ACP, KR, ARO, and CYC subunits of the PKS together catalyze the formation of an intermediate with a defined chain length, reduction pattern, and first two cyclizations. While the biosynthesis of naturally occurring polyketides typically requires the activity of downstream cyclases and other modifying enzymes to generate the characteristic biologically active product, subsequent reactions in the biosynthesis of engineered polyketides described here and in our earlier work occur in the absence of specific enzymes and are determined by the different physical and chemical properties of the individual molecules. Presumably reflecting such chemical possibilities and constraints, consistent patterns have been observed, leading to some degree of predictability. Two common moieties formed by the uncyclized methyl terminus of polyketide chains are hemiketals and benzene rings. Formation of a hemiketal occurs in the presence of an appropriately positioned enol and can be followed by a dehydration since both the hydrated and dehydrated forms are often isolated (FIG. 13(a)) (McDaniel, R. et al. *Science* (1993) 262:15461550; McDaniel, R. et al. *J. Am. Chem. Soc.* (1994) 116:10855–10859; Fu, H. et al. *J. Am. Chem. Soc.* (1994) 116:4166–4170), while benzene ring formation occurs with longer unprocessed methyl ends (FIG. 13(b)) (Fu et al. *J. Am. Chem. Soc.* (1994), supra). The most frequently observed moiety at the carboxyl terminus of the chain is a γ-pyrone ring formed by three ketide units (FIG. 13(c)) (McDaniel et al. *J. Am. Chem. Soc.* (1994), supra; Fu et al. *J. Am. Chem. Soc.* (1994), supra; Fu, H., et al. *Biochemistry* (1994) 33:9321–9326; Fu, H. et al. *Chem. & Biol.* (1994) 1:205–210; Zhang, H.-1. et al. *J. Org. Chem.* (1990) 55:1682–1684); if a free carboxylic acid remains, decarboxylation typically occurs if a β-carbonyl exists (FIG. 13(d)) (McDaniel et al. *Science* (1993), supra; McDaniel, R., Ebert-Khosla, S., Hopwood, D. A. & Khosla, C. *J. Am. Chem. Soc.* (1993), supra; Kao, C. M. et al. *J. Am. Chem.*

Figure 13E:
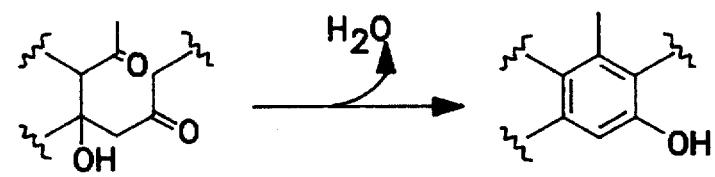

*Soc.* (1994) 116:11612–11613). Many aldol condensations can be predicted as well, bearing in mind that the methyl and carboxyl ends tend preferentially to cyclize independently but will co-cyclize if no alternative exists (FIG. 13(e)) (McDaniel et al. *Proc. Natl. Acad. Sci. USA* (1994), supra. These non-enzymatic cyclization patterns observed in vivo are also consistent with earlier biomimetic studies (Griffin, D. A. et al. *J. Chem. Soc. Perkin Trans.* (1984) 1:1035–1042).

Taken together with the structures of other naturally occurring bacterial aromatic polyketides, the design rules presented above can be extrapolated to estimate the extent of molecular diversity that might be generated via in vivo combinatorial biosynthesis of, for example, reduced and unreduced polyketides. For reduced polyketides, the identified degrees of freedom include chain length, aromatization of the first ring, and cyclization of the second ring. For unreduced ones, these include chain length and regiospecificity of the first ring cyclization. The number of accessible structures is the product of the number of ways in which each degree of freedom can be varied. Chains of five different lengths have so far been manipulated (16-, 18-20-, 22- and 24-carbon lengths). From the structure and deduced biosynthetic pathways of the dynemicin anthraquinone (Tokiwa, Y. et al. *J. Am. Chem. Soc.* (1992) 114:4107–4110), simaomicin (Carter, G. T. et al. *J. Org. Chem.* (1989) 54:4321–4323), and benastatin (Aoyama, T. et al. *J. Antibiot.* (1992) 45:1767–1772), the isolation of minimal PKSs that generate 14-, 26-, and possibly 28-carbon backbones, respectively, is anticipated, bringing the potential number to eight. Cloning of such minimal PKSs can be accomplished using the genes for minimal PKSs which have previously been isolated, such as the actI genes (Sherman et al. *EMBO J.* (1989), supra; Yu et al. *J. Bacteriol.* (1994), supra; Bibb et al. *Gene* (1994), supra; Malpartida, F. et al. *Nature* (1987) 325:818–821). Reduced chains can either be aromatized or not; a second ring cyclase is optional where the first ring is aromatized (FIG. 12). The regiospecificity of the first cyclization of an unreduced chain can be varied, depending on the presence of an enzyme like TcmN.

For example, for reduced polyketides the relevant degrees of freedom include the chain length (which can be manipulated in at least seven ways), the first ring aromatization (which can be manipulated in at least two ways), and the second ring cyclization (which can be manipulated in at least two ways for aromatized intermediates only). For unreduced polyketides, the regiospecificity of the first cyclization can also be manipulated. Thus, the combinatorial potential for reduced polyketides is at least 7×3=21; for unreduced polyketides the combinatorial potential is at least 7×2=14. Moreover, these numbers do not include additional minor products, on the order of 5 to 10 per major product, that are produced in the recombinant strains through non-enzymatic or non-specific enzyme catalyzed steps. Thus, the number of polyketides that can be generated from combinatorial manipulation of only the first few steps in aromatic polyketide biosynthesis is on the order of a few hundred. Thus, genetically engineered biosynthesis represents a potentially unlimited source of chemical diversity for drug discovery.

The number of potential novel polyketides increase geometrically as new degrees of freedom are exploited and/or protein engineering strategies are brought to bear on the task of creating enzyme subunits with specificities not observed in nature. For example, non-acetate starter units can be incorporated into polyketide backbones (e.g. propionate in daunorubicin and malonamide in oxytetracycline).

Furthermore, enzymes that catalyze downstream cyclizations and late-step modifications, such as group transfer reactions and oxidoreductions commonly seen in naturally occurring polyketides, can be studied along the lines presented here and elsewhere. It is therefore possible that at least some of these degrees of freedom can be combinatorially exploited to generate libraries of synthetic products with structural diversity that is comparable to that observed in nature.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Bacterial strains, plasmids, and culture conditions

S. coelicolor CH999 was used as a host for transformation by all plasmids. The construction of this strain is described below. DNA manipulations were performed in Escherichia coli MC1061. Plasmids were passaged through E. coli ET12567 (dam dcm hsdS Cm$^r$) (MacNeil, D. J. J. Bacteriol. (1988) 170:5607) to generate unmethylated DNA prior to transformation of S. coelicolor. E. coli strains were grown under standard conditions. S. coelicolor strains were grown on R2YE agar plates (Hopwood, D. A. et al. Genetic manipulation of Streptomyces. A laboratory manual. The John Innes Foundation: Norwich, 1985).

Manipulation of DNA and organisms

Polymerase chain reaction (PCR) was performed using Taq polymerase (Perkin Elmer Cetus) under conditions recommended by the enzyme manufacturer. Standard in vitro techniques were used for DNA manipulations (Sambrook, et al. Molecular Cloning: A Laboratory Manual (Current Edition)). E. coli was transformed with a Bio-Rad E. Coli Pulsing apparatus using protocols provided by Bio-Rad. S. coelicolor was transformed by standard procedures (Hopwood, D. A. et al. Genetic manipulation of Streptomyces. A laboratory manual. The John Innes Foundation: Norwich, 1985) and transformants were selected using 2 ml of a 500 mg/ml thiostrepton overlay.

Construction of plasmids containing recombinant PKSs

All plasmids are derivatives of pRM5, described below. fren PKS genes were amplified via PCR with 5' and 3' restriction sites flanking the genes in accordance with the location of cloning sites on pRM5 (i.e. PacI-NsiI for ORF1, NsiI-XbaI for ORF2, and XbaI-PstI for ORF3). Following subcloning and sequencing, the amplified fragments were cloned in place of the corresponding fragments in pRM5 to generate the plasmids for transformation.

Production and purification of polyketides

For initial screening, all strains were grown at 30° C. as confluent lawns on 10–30 plates each containing approximately 30 ml of agar medium for 6–8 days. Additional plates were made as needed to obtain sufficient material for complete characterization. CH999 was a negative control when screening for potential polyketides. The agar was finely chopped and extracted with ethyl acetate/1% acetic acid or ethyl acetate:methanol (4:1)/1% acetic acid. The concentrated extract was then flashed through a silica gel (Baker 40 mm) chromatography column in ethyl acetate/1% acetic acid. Alternatively, the extract was applied to a Florisil column (Fisher Scientific) and eluted with ethyl acetate:ethanol:acetic acid (17:2:1). The primary yellow fraction was further purified via high-performance liquid chromatography (HPLC) using a 20–60% acetonitrile/water/1% acetic acid gradient on a preparative reverse phase (C-18) column (Beckman). Absorbance was monitored at 280nm and 410nm. In general, the yield of purified product from these strains was approximately 10 mg/l for compounds 1 and 2 (FIG. 4), and 5 mg/l for compounds 7 and 8 (FIG. 7).

SEK4, (12), was produced and purified as follows. CH999/pSEK4 was grown on 90 agar plates (~34 ml/plate) at 30° C. for 7 days. The agar was chopped and extracted with ethyl acetate/methanol (4/1) in the presence of 1% acetic acid (3×1000 ml). Following removal of the solvent under vacuum, 200 ml of ethyl acetate containing 1% acetic acid were added. The precipitate was filtered and discarded, and the solvent was evaporated to dryness. The product mixture was applied to a Florisil column (Fisher Scientific), and eluted with ethyl acetate containing 3% acetic acid. The first 100 ml fraction was collected, and concentrated down to 5 ml. 1 ml methanol was added, and the mixture was kept at 4° C. overnight. The precipitate was collected by filtration, and washed with ethyl acetate to give 850 mg of pure product. $R_f$=0.48 (ethyl acetate with 1% acetic acid). Results from NMR spectroscopy on SEK4 are reported in Table 4. FAB HRMS (NBA), M+H$^+$, calculated m/e 319.0818, observed m/e 319.0820.

To produce SEK15 (13) and SEK15b (16), CH999/pSEK15 was grown on 90 agar plates, and the product was extracted in the same manner as SEK4. The mixture was applied to a Florisil column (ethyl acetate with 5% acetic acid), and fractions containing the major products were combined and evaporated to dryness. The products were further purified using preparative C-18 reverse phase HPLC (Beckman) (mobile phase: acetonitrile/water =1/10 to 3/5 gradient in the presence of 1% acetic acid). The yield of SEK15, (13), was 250 mg. $R_f$=0.41 (ethyl acetate with 1% acetic acid). Results from NMR spectroscopy on SEK4 are reported in Table 4. FAB HRMS (NBA), M+H$^+$calculated m/e 385.0923, observed m/e 385.0920.

$[1,2^{-13}C_2]$ acetate feeding experiments

Two 2 1 flasks each containing 400 ml of modified NMP medium (Strauch, E. et al. Mol. Microbiol. (1991) 5:289) were inoculated with spores of S. coelicolor CH999/pRM18, CH999/pSEK4 or CH999/pSEK15, and incubated in a shaker at 30 degrees C. and 300 rpm. To each flask, 50 mg of sodium $[1,2^{-13}C_2]$ acetate (Aldrich) was added at 72 and 96 hrs. After 120 hrs, the cultures were pooled and extracted with two 500 ml volumes of ethyl acetate/1% acetic acid. The organic phase was kept and purification proceeded as described above. $^{13}$C NMR data indicate approximately a 2–3% enrichment for the CH999/pRM18 product; a 0.5–1% enrichment for SEK4 and a 1–2% enrichment for SEK15.

NMR spectroscopy

All spectra were recorded on a Varian XL-400 except for HETCOR analysis of RM18 (10) (FIG. 8), which was performed on a Nicolet NT-360. $^{13}$C spectra were acquired with continuous broadband proton decoupling. For NOE studies of RM18 (10), the one-dimensional difference method was employed. All compounds were dissolved in DMSO-$d_6$ (Sigma, 99+ atom % D) and spectra were referenced internally to the solvent. Hydroxyl resonances were identified by adding D$_2$O (Aldrich, 99 atom % D) and checking for disappearance of signal.

EXAMPLE 1

Production of S. coelicolor CH999

An S. coelicolor host cell, genetically engineered to remove the native act gene cluster, and termed CH999, was constructed using *S. coelicolor* CH1 (Khosla, *C. Molec. Microbiol.* (1992) 6:3237), using the strategy depicted in FIG. 2. (CH1 is derived from *S. coelicolor* B385 (Rudd, B. A. M. Genetics of Pigmented Secondary Metabolites in *Streptomyces coelicolor* (1978) Ph.D. Thesis, University of East Anglia, Norwich, England.) CH1 includes the act gene cluster which codes for enzymes involved in the biosynthesis and export of the polyketide antibiotic actinorhodin. The cluster is made up of the PKS genes, flanked by several post-PKS biosynthetic genes including those involved in cyclization, aromatization, and subsequent chemical tailoring (FIG. 2A). Also present are the genes responsible for transcriptional activation of the act genes. The act gene cluster was deleted from CH1 using homologous recombination as described in Khosla, C. et al. *Molec. Microbiol.* (1992) 6:3237.

In particular, plasmid pLRermEts (FIG. 2B) was constructed with the following features: a ColEI replicon from pBR322, the temperature sensitive replicon from pSG5 (Muth, G. et al. *Mol. Gen. Genet.* (1989) 219:341), ampicillin and thiostrepton resistance markers, and a disruption cassette including a 2 kb BamHI/XhoI fragment from the 5' end of the act cluster, a 1.5 kb ermE fragment (Khosla, C. et al. *Molec. Microbiol.* (1992) 6:3237), and a 1.9 kb SphI/PstI fragment from the 3' end of the act cluster. The 5' fragment extended from the BamHI site 1 (Malpartida, F. and Hopwood, D. A. *Nature* (1984) 309:462; Malpartida, F. and Hopwood, D.A. *Mol. Gen. Genet.* (1986) 205:66) downstream to a XhoI site. The 3' fragment extended from PstI site 20 upstream to SphI site 19.2 (Fernandez-Moreno, M. A. et al. *J. Biol. Chem.* (1992) 267:19278). The 5' and 3' fragments (shown as hatched DNA in FIG. 2) were cloned in the same relative orientation as in the act cluster. CH1 was transformed with pLRermEts. The plasmid was subsequently cured from candidate transformants by streaking non-selectively at 39° C. Several colonies that were lincomycin resistant, thiostrepton sensitive, and unable to produce actinorhodin, were isolated and checked via Southern blotting. One of them was designated CH999.

EXAMPLE 2

Production of the Recombinant Vector pRM5

Figure 3:
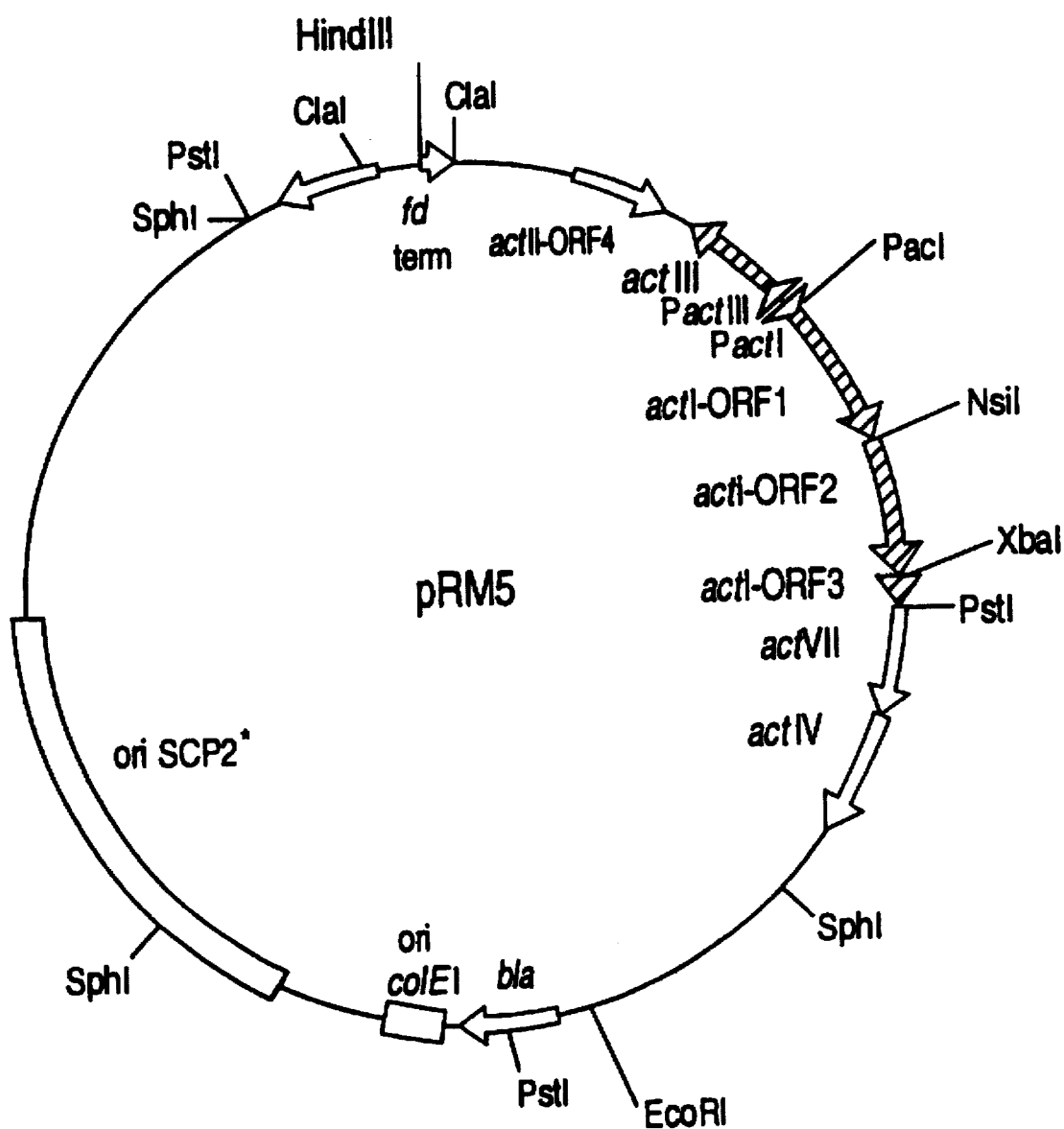
FIG. 3 is a diagram of plasmid pRM5.

Shuttle plasmids are used to express recombinant PKSs in CH999. Such plasmids typically include a colEI replicon, an appropriately truncated SCP2* Streptomyces replicon, two act-promoters to allow for bidirectional cloning, the gene encoding the actII-ORF4 activator which induces transcription from act promoters during the transition from growth phase to stationary phase, and appropriate marker genes. Restriction sites have been engineered into these vectors to facilitate the combinatorial construction of PKS gene clusters starting from cassettes encoding individual subunits (or domains) of naturally occurring PKSs. The primary advantages of this method are that (i) all relevant biosynthetic genes are plasmid-borne and therefore amenable to facile manipulation and mutagenesis in *E.coli*, (ii) the entire library of PKS gene clusters can be expressed in the same bacterial host which is genetically and physiologically well-characterized and presumably contains most, if not all, ancillary activities required for in vivo production of polyketides, (iii) polyketides are produced in a secondary metabolite-like manner, thereby alleviating the toxic effects of synthesizing potentially bioactive compounds in vivo, and (iv) molecules thus produced undergo fewer side reactions than if the same pathways were expressed in wild-type organisms or blocked mutants.

pRM5 (FIG. 3) was the shuttle plasmid used for expressing PKSs in CH999. It includes a ColEI replicon to allow genetic engineering in *E. coli*, an appropriately truncated SCP2* (low copy number) Streptomyces replicon, and the actII-ORF4 activator gene from the act cluster, which induces transcription from act promoters during the transition from growth phase to stationary phase in the vegetative mycelium. As shown in FIG. 3, pRM5 carries the divergent actI/actIII promoter pair, together with convenient cloning sites to facilitate the insertion of a variety of engineered PKS genes downstream of both promoters. pRM5 lacks the par locus of SCP2*; as a result the plasmid is slightly unstable (approx. 2% loss in the absence of thiostrepton). This feature was deliberately introduced in order to allow for rapid confirmation that a phenotype of interest could be unambiguously assigned to the plasmid-borne mutant PKS. The recombinant PKSs from pRM5 are expressed approximately at the transition from exponential to stationary phase of growth, in good yields.

pRM5 was constructed as follows. A 10.5 kb SphI/HindIII fragment from pIJ903 (containing a portion of the fertility locus and the origin of replication of SCP2* as well as the colEI origin of replication and the β-lactamase gene from pBR327) (Lydiate, D. J. *Gene* (1985) 35:223) was ligated with a 1.5 kb HindIII/SphI tsr gene cassette to yield pRM1. pRM5 was constructed by inserting the following two fragments between the unique HindIII and EcoRI sites of pRM1: a 0.3 kb HindIII/HpaI(blunt) fragment carrying a transcription terminator from phage fd (Khosla, C. et al. *Molec. Microbiol.* (1992) 6:3237), and a 10 kb fragment from the act cluster extending from the NcoI site (1 kb upstream of the actII-ORF4 activator gene) (Hallam, S. E. et al. *Gene* (1988) 74:305; Fernandez-Moreno, M. A. et al. *Cell* (1991) 66:769; Caballero, J. L. *Mol. Gen. Genet.* (1991) 230:401) to the PstI site downstream of the actI-VII-IV genes (Fernandez-Moreno, M. A. et al. *J. Biol. Chem.* (1992) 267:19278).

To facilitate the expression of any desired recombinant PKS under the control of the actI promoter (which is activated by the actII-ORF4 gene product), restriction sites for PacI, NsiI, XbaI, and PstI were engineered into the act DNA in intercistronic positions. In pRM5, as well as in all other PKS expression plasmids described here, ORF1, 2, and 3 alleles were cloned between these sites as cassettes engineered with their own RBSs.

In particular, in most naturally occurring aromatic polyketide synthase gene clusters in actinomycetes, ORF1 and ORF2 are translationally coupled. In order to facilitate construction of recombinant PKSs, the ORF1 and ORF2 alleles used here were cloned as independent (uncoupled) cassettes. For act ORF1, the following sequence was engineered into pRM5: CCACCGGACGAACGCATCGAT-TAATTAAGGAGGACCATCATG SEQ ID NO:1, where the boldfaced sequence corresponds to upstream DNA from the actI region, TTAATTAA is the PacI recognition site, and ATG is the start codon of act ORF1. The following sequence was engineered between act ORF1 and ORF2: NTGAAT-GCATGGAGGAGCCATCATG SE2 ID NO:2, where TGA and ATG are the stop and start codons of ORF1 and ORF2, respectively, ATGCAT is the NsiI recognition site, and the replacement of N (A in act DNA, A or G in alleles from other PKSs) with a C results in translational decoupling. The following sequence was engineered downstream of act ORF2: TAATCTAGA, where TAA is the stop codon, and TCTAGA is the XbaI recognition site. This allowed fusion of act ORF1 and ORF2 (engineered as above) to an XbaI site that had been engineered upstream of act ORF3 (Khosla, C.

et al. *Molec. Microbiol.* (1992) 6:3237). As a control, pRM2 was constructed, identical to pRM5, but lacking any of the engineered sequences. ORF1 and ORF2 in pRM2 are translationally coupled. Comparison of the product profiles of CH999/pRM2 and CH999/pRM5 revealed that the decoupling strategy described here had no detectable influence on product distribution or product levels.

EXAMPLE 3

Polyketides Produced using CH999 Transformed with pRM5

Figure 4:
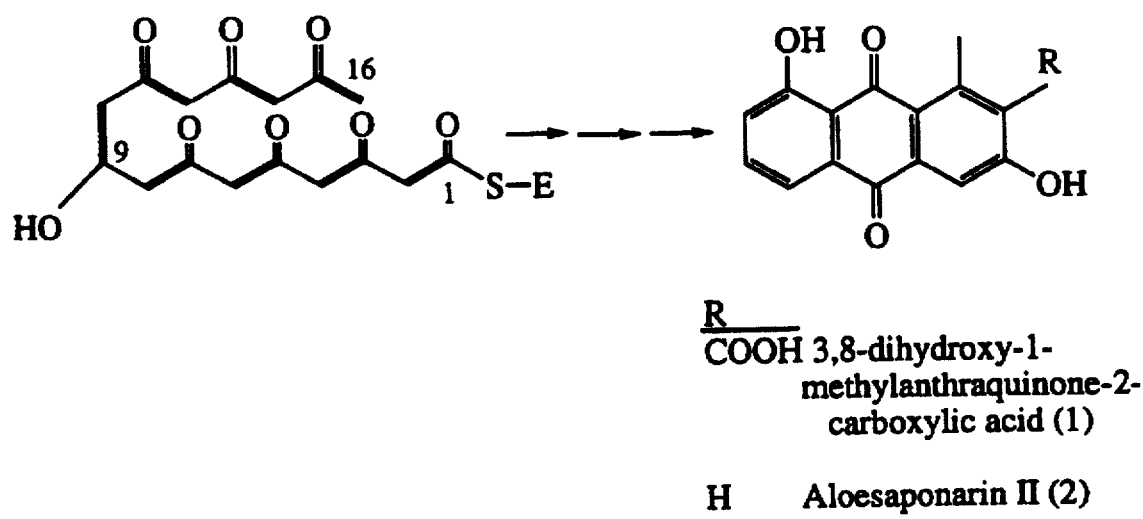
FIG. 4 schematically illustrates formation of aloesaponarin II (2) and its carboxylated analog, 3,8-dihydroxy-1-methylanthraquinone-2-carboxylic acid (1) as described in Example 3.

Plasmid pRM5 was introduced into *S. coelicolor* CH999 using standard techniques. (See, e.g., Sambrook, et al. *Molecular Cloning: A Laboratory Manual* (Current Edition.) CH999 transformed with pRM5 produced a large amount of yellowish-brown material. The two most abundant products were characterized by NMR and mass spectroscopy as aloesaponarin II (2) (Bartel, P. L. et al. *J. Bacteriol.* (1990) 172:4816) and its carboxylated analog, 3,8-dihydroxy-1-methylanthraquinone-2-carboxylic acid (1) (Cameron, D. W. et al. *Liebigs Ann. Chem.* (1989) 7:699) (FIG. 4). It is presumed that 2 is derived from 1 by non-enzymatic decarboxylation (Bartel, P. L. et al. *J. Bacteriol.* (1990) 172:4816). Compounds 1 and 2 were present in approximately a 1:5 molar ratio. Approximately 100 mg of the mixture could be easily purified from 1 l of culture. The CH999/pRM5 host-vector system was therefore functioning as expected to produce significant amounts of a stable, only minimally modified polyketide metabolite. The production of 1 and 2 is consistent with the proposed pathway of actinorhodin biosynthesis (Bartel, P. L. et al. *J. Bacteriol.* (1990) 172:4816). Both metabolites, like the actinorhodin backbone, are derived from a 16-carbon polyketide with a single ketoreduction at C-9.

When CH999 was transformed with pSEK4, identical to pRM5 except for replacement of a 140 bp SphI/SalI fragment within the act KR gene by the SphI/SalI fragment from pUC19, the resulting strain produced abundant quantities of the aromatic polyketide SEK4 (12). The exact structure of this product is slightly different from desoxyerythrolaccin (Bartel, P. L. et al. *J. Bacteriol.* (1990) 172:4816). However, in vivo isotopic labeling studies using 1,2-$^{13}C_2$- labeled acetate confirmed that the polyketide backbone is derived from 8 acetates. Moreover, the aromatic region of the $^1H$ spectrum, as well as the 13C NMR spectrum of this product, are consistent with a tricyclic structure similar to 1, but lacking any ketoreduction (see Table 4).

EXAMPLE 4

Construction and Analysis of Hybrid Polyketide Synthases

A. Construction of hybrid PKSs including components from act, gra and tcm PKSs

Figure 1B:
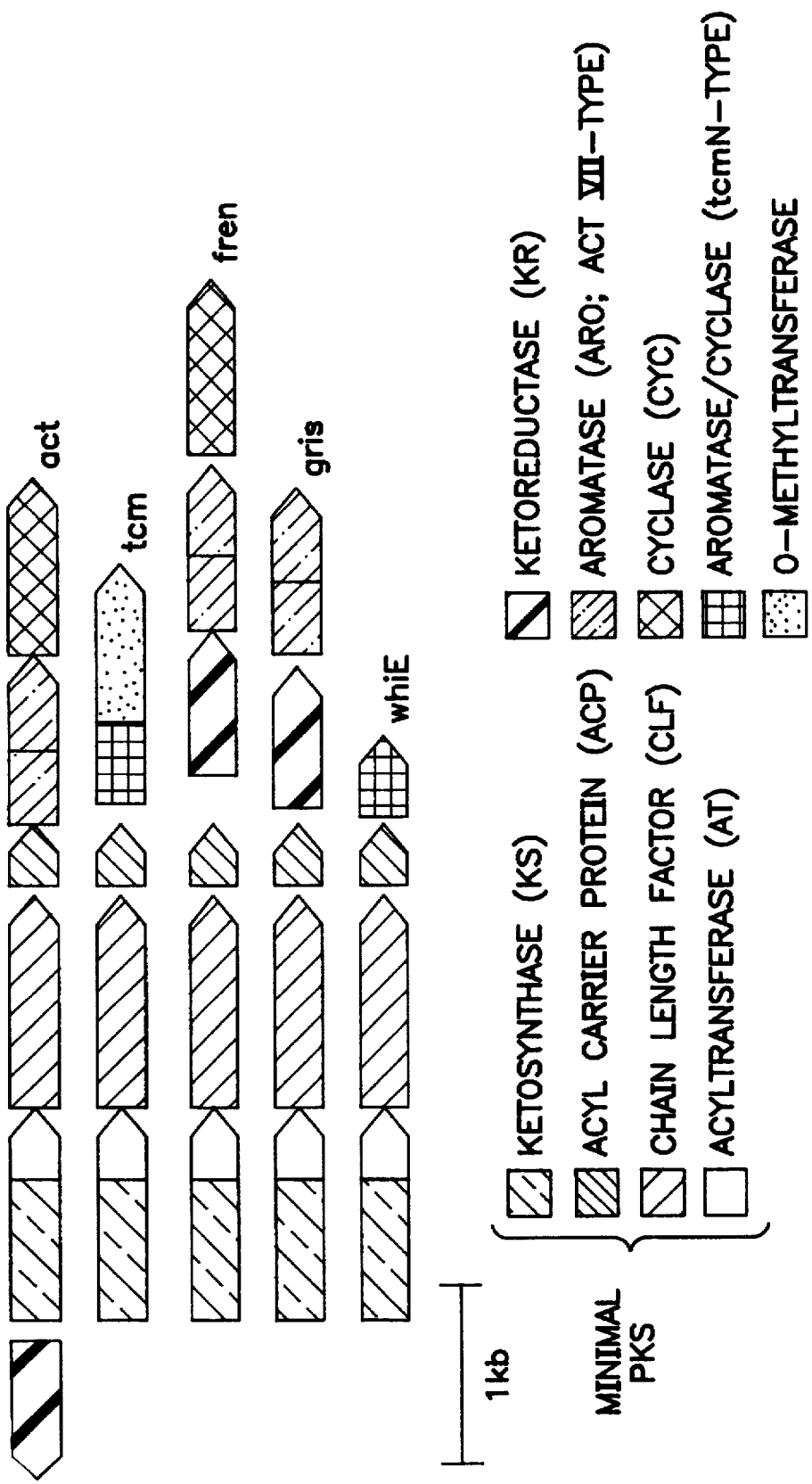
FIG. 1B shows the gene clusters for act, tcm, fren, gris, and whiE PKSs and cyclases.
Figure 6:
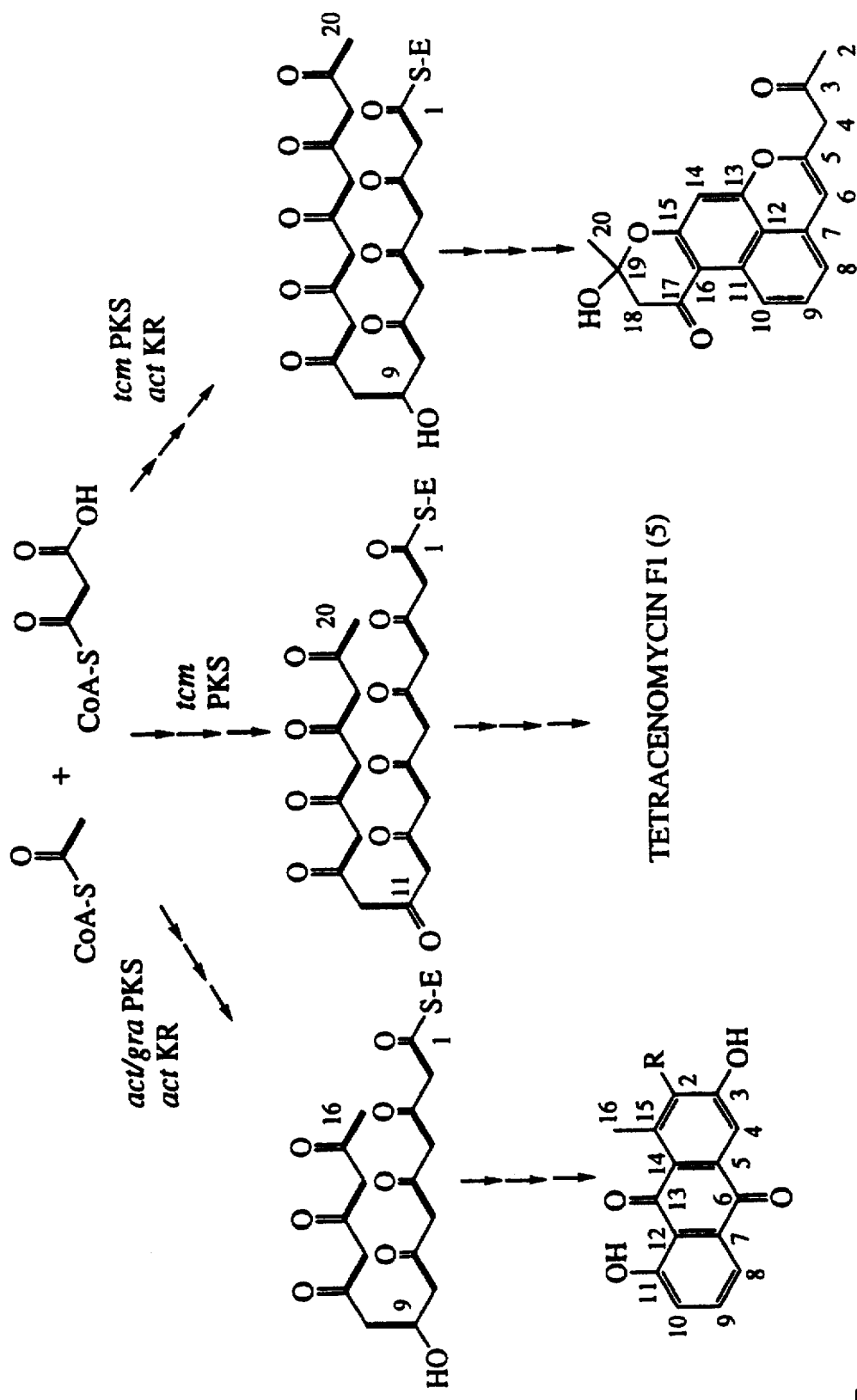
FIG. 6 schematically illustrates the preparation, via cyclization of the polyketide precursors, of aloesaponarin II (2), its carboxylated analog, 3,8-dihydroxy-1-methylanthraquinone-2-carboxylic acid (1), tetracenomycin (5) and new compound RM20 (9), as explained in Example 4, part (A).

FIG. 1A shows the PKSs responsible for synthesizing the carbon chain backbones of actinorhodin (3), granaticin (4), and tetracenomycin (5) (structures shown in FIG. 5) which contain homologous putative KS/AT and ACP subunits, as well as the ORF2 product. The act and gra PKSs also have KRs, lacking in the tcm PKS. Corresponding proteins from each cluster show a high degree of sequence identity. The percentage identities between corresponding PKS proteins in the three clusters are as follows: KS/AT: act/gra 76, act/tcm 64, gra/tcm 70; CLF: act/gra 60, act/tcm 58, gra/tcm 54; ACP: act/gra 60, act/tcm 43, gra/tcm 44. The act and gra PKSs synthesize identical 16-carbon backbones derived from 8 acetate residues with a ketoreduction at C-9 (FIG. 6). In contrast, also as shown in FIG. 6, the tcm polyketide backbone differs in overall carbon chain length (20 instead of 16 carbons), lack of any ketoreduction, and regiospecificity of the first cyclization, which occurs between carbons 9 and 14, instead of carbons 7 and 12 for act and gra.

In an attempt to generate novel polyketides, differing in a range of properties, as well as to elucidate aspects of the programming of aromatic PKSs, a systematic series of minimal PKS gene clusters, using various permutations of the ORF1 (encoding the KS/AT subunit), ORF2 (encoding the CLF subunit) and ORF3 (encoding the ACP subunit) gene products from the act, gra and tcm gene clusters were cloned into pRM5 in place of the existing act genes, as shown in Table 1. The resulting plasmids were used to transform CH999 as above.

Analysis of the products of the recombinant PKSs containing various permutations among the KS/AT, ORF2 product, and ACP subunits of the PKSs (all constructs also containing the act KR, cyclase, and dehydratase genes) indicated that the synthases could be grouped into three categories (Table 1): those that did not produce any polyketide; those that produced compound 1 (in addition to a small amount of 2); and those that produced a novel polyketide 9 (designated RM20) (FIG. 6). The structure of 9 suggests that the polyketide backbone precursor of this molecule is derived from 10 acetate residues with a single ketoreduction at the C-9 position.

In order to investigate the influence of the act KR on the reduction and cyclization patterns of a heterologous polyketide chain, pSEK15 was also constructed, which included tcm ORFs 1–3, but lacked the act KR. (The deletion in the act KR gene in this construct was identical to that in pSEK4.) Analysis of CH999/pSEK15 showed the 20 carbon chain product, SEK15 (13) which resembled, but was not identical to, tetracenomycin C or its shunt products. NMR spectroscopy was also consistent with a completely unreduced decaketide backbone (see Table 4).

All act/gra hybrids produced compound 1, consistent with the identical structures of the presumed actinorhodin and granaticin polyketides. In each case where a product could be isolated from a tcm/act hybrid, the chain length of the polyketide was identical to that of the natural product corresponding to the source of ORF2. This implies that the ORF2 product, and not the ACP or KS/AT, controls carbon chain length. Furthermore, since all polyketides produced by the hybrids described here, except the ones lacking the KR (CH999/pSEK4 and CH999/pSEK15), underwent a single ketoreduction, it can be concluded that: (i) the KR is both necessary and sufficient for ketoreduction to occur; (ii) this reduction always occurs at the C-9 position in the final polyketide backbone (counting from the carboxyl end of the chain); and (iii) while unreduced polyketides may undergo alternative cyclization patterns, in nascent polyketide chains that have undergone ketoreduction, the regiochemistry of the first cyclization is dictated by the position of the resulting hydroxyl, irrespective of how this cyclization occurs in the non-reduced product. In other words, the tcm PKS could be engineered to exhibit new cyclization specificity by including a ketoreductase.

A striking feature of RM20 (9) is the pattern of cyclizations following the first cyclization. Isolation of mutactin (6) from an actVII mutant suggested that the actVII product and its tcm homolog catalyze the cyclization of the second ring in the biosynthesis of actinorhodin (3) and tetracenomycin (5), respectively (Sherman, D. H. et al. *Tetrahedron* (1991) 47:6029; Summers, R. G. et al. *J. Bacteriol.* (1992) 174:1810). The cyclization pattern of RM20 (9) is different from that of 1 and tetracenomycin F1, despite the presence of the actVII gene on pRM20 (9). It therefore appears that the act cyclase cannot cyclize longer polyketide chains.

Figure 8A:
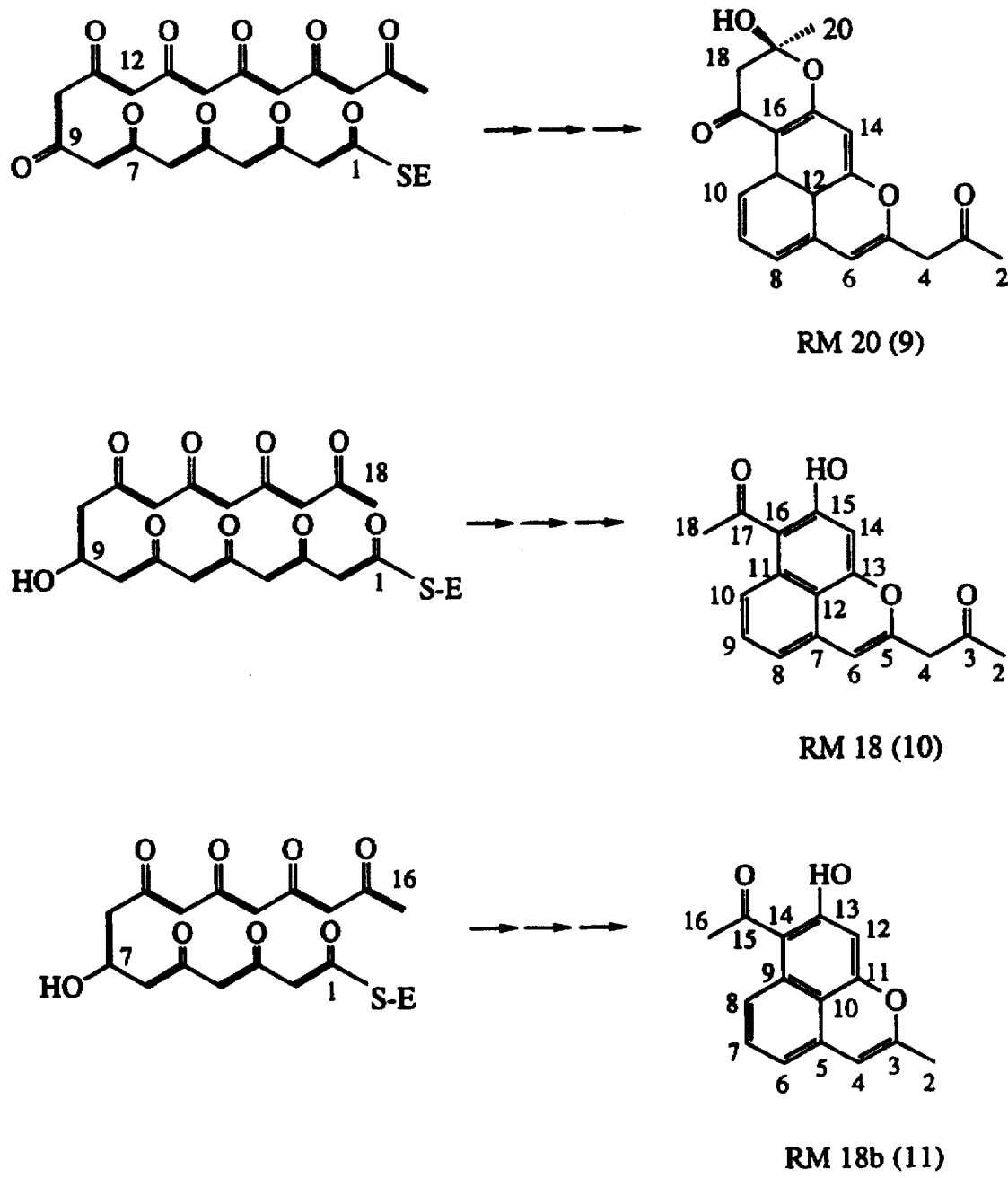
FIG. 8 schematically illustrates the preparation, via cyclization of the polyketide precursors, of novel compounds RM20 (9), RM18 (10), RM18b (11)(a), SEK4 (12), SEK15 (13)(b), RM20b (14), RM20c (15) and SEK15b (16)(c).
Figure 8B:
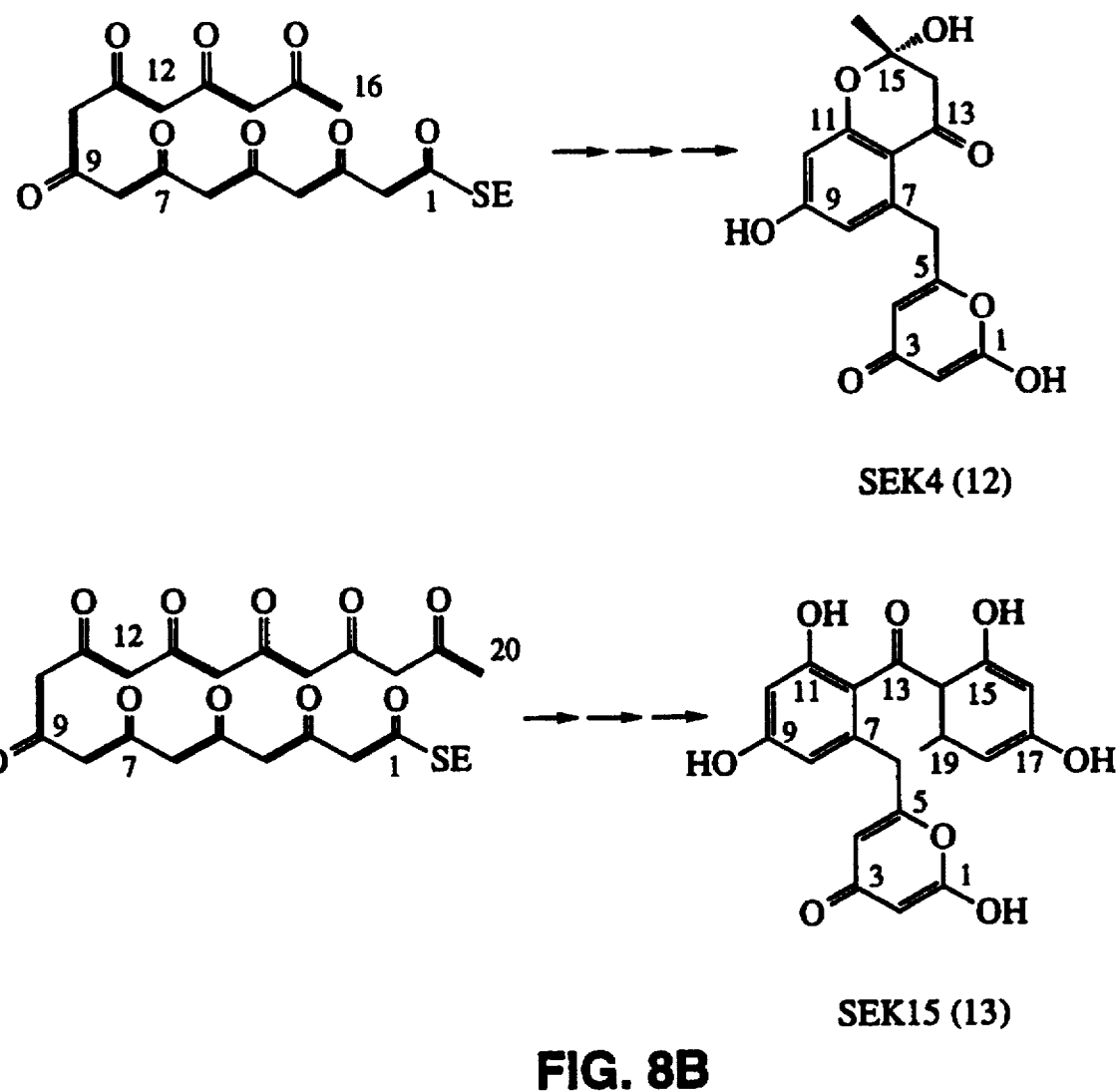

Unexpectedly, the strain containing the minimal tcm PKS alone (CH999/pSEK33) produced two polyketides, SEK15 (13) and SEK15b (16), as depicted in FIG. 8, in approximately equal quantities. Compounds (13) and (16) were also isolated from CH999/pSEK15, however, greater quantities of compound (13) were isolated this construct than of compound (16).

SEK15b is a novel compound, the structure of which was elucidated through a combination of NMR spectroscopy, sodium $[1,2-{}^{13}C_2]$ acetate feeding experiments and mass spectroscopy. Results from 1H and 13C NMR indicated that SEK15b consisted of an unreduced anthraquinone moiety and a pyrone moiety. Sodium $[1,2-{}^{13}C_2]$-acetate feeding experiments confirmed that the carbon chain of SEK15b was derived from 10 acetate units. The coupling constants calculated from the $^{13}C$ NMR spectrum of the enriched SEK15b sample facilitated peak assignment. Fast atom bombardment (FAB) mass spectroscopy gave a molecular weight of 381 (M+H$^+$), consistent with $C_{20}H_{12}O_8$. Deuterium exchange was used to confirm the presence of each hydroxyl in SEK15b.

In order to identify the degrees of freedom available in vivo to a nascent polyketide chain for cyclizing in the absence of an active cyclase, polyketides produced by recombinant *S. coelicolor* CH999/pRM37 (McDaniel et al. (1993), supra) were analyzed. The biosynthetic enzymes encoded by pRM37 are the tcm ketosynthase/acyltransferase (KS/AT), the tcm chain length determining factor (CLF), the tcm acyl carrier protein (ACP), and the act ketoreductase (KR).

Two novel compounds, RM20b (14) and RM20c (15) (FIG. 8) were discovered in the culture medium of CH999/pRM37, which had previously yielded RM20 (9). The relative quantities of the three compounds recovered were 3:7:1 (RM20:RM20b:RM20c). The structures of (14) and (15) were elucidated through a combination of mass spectroscopy, NMR spectroscopy and isotope labeling experiments. $^1H$ and $^{13}C$ NMR spectra suggested that RM20b and RM20c were diastereomers, each containing a pyrone moiety. Optical rotations ($[\alpha]_D^{20}$ were found to by +210.8° for RM20b (EtOH, 0.55%) and +78.0° for RM20c (EtOH 0 33%) Sodium $[12-{}^{13}C_2]$-acetate feeding experiments confirmed that the carbon chain of RM20b (and by inference RM20c) was derived from 10 acetate units. Deuterium exchange studies were carried out in order to identify $^1H$ NMR peaks corresponding to potential hydroxyl groups on both RM20b and RM20c. Proton coupling constants were calculated from the results of $^1H$ NMR and one-dimensional decoupling experiments. In particular, the coupling pattern in the upfield region of the spectrum indicated a 5-proton spin system of two methylene groups surrounding a central carbinol methine proton. High resolution fast atom bombardment (FAB) mass spectroscopy gave molecular weights of (519.0056) (M=Cs$^+$) for RM20b and 387.1070 (M+H$^+$) for RM20c, which is consistent with $C_{20}H_{18}O_8$ (M+Cs$^+$, 519.0056; M+H$^+$, 387.1080). Based on theses data, structures (14) and (15) (FIG. 8) were assigned to RM20b and RM20c, respectively.

Data from $^1H$ and $^{13}C$ NMR indicated that the coupling constants between H-9 and the geminal protons on C-8 were 12.1 or 12.2 and 2.5 or 2.2 Hz for RM20b or RM20c, respectively. The coupling constants between H-9 and the geminal protons on C-10 were 9.6 or 9.7 and 5.7 or 5.8 Hz for Rm20b or RM20c, respectively. These values are typical of a $J_{a,a}$ ($J_{9a,8a}$ or $J_{9a,10a}$) and $J_{a,e}$ ($J_{9a,8e}$ or $J_{9a,10e}$) coupling pattern, and indicate an axial position for H-9 in both RM20b and Rm20c. In contrast, the chemical shifts of the hydroxyl proton of the C-7 hydroxyls on the two molecules were 16.18 and 6.14 ppm for RM20b and RM20c, respectively. These values indicate a hydrogen bond between the C-7 hydroxyl and a suitably positioned acceptor atom in RM20b, but not in RM20c. The most likely candidate acceptor atoms for such hydrogen bonding are the C-13 carbonyl oxygen in the conjugated pyrone ring system, or the bridge oxygen in the isolate pyrone ring. The former appears to be likely as it would be impossible to discriminate between (14) and (15) if the latter were the case. Furthermore, comparison of $^{13}C$ NMR spectra of RM20b and RM20c revealed that the greatest differences between (14) and (15) were in the chemical shifts of the carbons that make up the conjugated pyrone ring (+5.9, −6.1, +8.9,−7.8 and +2.0 ppm for C-11, C-12, C-13, C-14 and C-15, respectively). Such a pattern of alternating upfield and downfield shifts can be explained by the fact that the C-7 hydroxyl is hydrogen-bonded to the C-13 carbonyl, since hydrogen bonding would be expected to reduce the electron density around C-11, C-13 and C-15, but increase the electron density around C-12 and C-14. To confirm the C-7/C-13 hydrogen bond assignment, the exchangeable protons RM20b and RM20c were replaced with deuterium (by incubating in the presence of $D_2O$), and the samples were analyzed by $^{13}C$ NMR. The C-13 peak in RM20b, but not RM20c, underwent an upfield shift (1.7 ppm), which can be explained by a weaker C-7/C-13 non-covalent bond in RM20b when hydrogen is replace with deuterium. In order to form a hydrogen bond with the C-13 carbonyl, the C-7 hydroxyl of RM20b must occupy the equatorial position. Thus, it can be inferred that the C-7 and C-9 hydroxyls are on the same face (syn) of the conjugated ring system in the major isomer (RM20b), whereas they are on opposite sides (anti) in the minor isomer (RM20c).

No polyketide could be detected in CH999/pRM15,/ pRM35, and/pRM36. Thus, only some ORF1-ORF2 combinations are functional. Since each subunit was functional in at least one recombinant synthase, protein expression/ folding problems are unlikely to be the cause. Instead, imperfect or inhibitory association between the different subunits of these enzyme complexes, or biosynthesis of (aborted) short chain products that are rapidly degraded, are plausible explanations.

B. Construction of hybrid PKSs including components from act and fren PKSs

*Streptomyces roseofulvus* produces both frenolicin B (7) (Iwai, Y. et al. *J. Antibiot.* (1978) 31:959) and nanaomycin A (8) (Tsuzuki, K. et al. *J. Antibiot.* (1986) 39:1343). A 10 kb DNA fragment (referred to as the fren locus hereafter) was cloned from a genomic library of *S. roseofulvus* (Bibb, M. J. et al. submitted) using DNA encoding the KS/AT and KR components of the act PKS of *S. coelicolor* A3(2) as a probe (Malpartida, F. et al. *Nature* (1987) 325:818). (See FIG. 7 for structural representations.) DNA sequencing of the fren locus revealed the existence of (among others) genes with a high degree of identity to those encoding the act KS/AT, CLF, ACP, KR, and cyclase.

To produce the novel polyketides, the ORF1, 2 and 3 act genes present in pRM5 were replaced with the corresponding fren genes, as shown in Table 2. *S. coelicolor* CH999, constructed as described above, was transformed with these plasmids. (The genes encoding the act KR, and the act cyclase were also present on each of these genetic constructs.) Based on results from similar experiments with act and tcm PKSs, described above, it was expected that the act KR would be able to reduce the products of all functional recombinant PKSs, whereas the ability of the act cyclase to catalyze the second cyclization would depend upon the chain length of the product of the fren PKS.

The results summarized in Table 2 indicate that most of the transformants expressed functional PKSs, as assayed by their ability to produce aromatic polyketides. Structural analysis of the major products revealed that the producer strains could be grouped into two categories: those that synthesized compound 1 (together with a smaller amount of its decarboxylated side-product (2), and those that synthesized a mixture of compounds 1, 10 and 11 in a roughly 1:2:2 ratio. (Small amounts of 2 were also found in all strains producing 1.) Compounds 1 and 2 had been observed before as natural products, and were the metabolites produced by a PKS consisting entirely of act subunits, as described in Example 3. Compounds 10 and 11 (designated RM18 and RM18b, respectively) are novel structures whose chemical synthesis or isolation as natural products has not been reported previously.

The structures of 10 and 11 were elucidated through a combination of mass spectroscopy, NMR spectroscopy, and isotope labeling experiments. The $^1$H and $^{13}$C spectral assignments are shown in Table 3, along with $^{13}$C-$^{13}$C coupling constants for 10obtained through sodium [1,2-$^{13}$C$_2$] acetate feeding experiments (described below). Unequivocal assignments for compound 10 were established with 1D nuclear Overhauser effect (NOE) and long range heteronuclear correlation (HETCOR) studies. Deuterium exchange confirmed the presence of hydroxyls at C-15 of compound 10 and C-13 of compound 11. Field desorption mass spectrometry (FD-MS) of 2 revealed a molecular weight of 282, consistent with $C_{17}H_{14}O_4$ (282.2952).

Earlier studies showed that the polyketide backbone of 2 (Bartel, P. L. et al. *J. Bacteriol.* (1990) 172:4816) (and by inference, 1) is derived from iterative condensations of 8 acetate residues with a single ketoreduction at C-9. It may also be argued that nanaomycin (8) arises from an identical carbon chain backbone. Therefore, it is very likely that nanaomycin is a product of the fren PKS genes in *S. roseofulvus*. Regiospecificity of the first cyclization leading to the formation of 1 is guided by the position of the ketoreduction, whereas that of the second cyclization is controlled by the act cyclase (Zhang, H. L. et al. *J. Org. Chem.* (1990) 55:1682).

In order to trace the carbon chain backbone of RM18 (10) in vivo feeding experiments using [1, 2-$^{13}$C$_2$] acetate were performed on CH999/pRM18, followed by NMR analysis of labelled RM18 (10). The $^{13}$C coupling data (summarized in Table 3) indicate that the polyketide backbone of RM18 (10) is derived from 9 acetate residues, followed by a terminal decarboxylation (the C-2 $^{13}$C resonance appears as an enhanced singlet), which presumably occurs non-enzymatically. Furthermore, the absence of a hydroxyl group at the C-9 position suggests that a ketoreduction occurs at this carbon. Since these two features would be expected to occur in the putative frenolicin (7) backbone, the results suggest that, in addition to synthesizing nanaomycin, the fren PKS genes are responsible for the biosynthesis of frenolicin in *S. roseofulvus*. This appears to be the first unambiguous case of a PKS with relaxed chain length specificity. However, unlike the putative backbone of frenolicin, the C-17 carbonyl of RM18 (10) is not reduced. This could either reflect the absence from pRM18 of a specific ketoreductase, dehydratase, and an enoylreductase (present in the fren gene cluster in *S. roseofulvus*), or it could reflect a different origin for carbons 15–18 in frenolicin.

Regiospecificity of the first cyclization leading to the formation of RM18 (10) is guided by the position of the ketoreduction; however the second cyclization occurs differently from that in 7 or 1, and is similar to the cyclization pattern observed in RM20 (9), a decaketide produced by the tcm PKS, as described above. Therefore, as in the case of RM20 (9), it could be argued that the act cyclase cannot catalyze the second cyclization of the RM18 precursor, and that its subsequent cyclizations, which presumably occur non-enzymatically, are dictated by temporal differences in release of different portions of the nascent polyketide chain into an aqueous environment. In view of the ability of CH999/pRM18 (and CH999/pRM34) to produce 1, one can rule out the possibility that the cyclase cannot associate with the fren PKS (KS/AT, CLF, and ACP). A more likely explanation is that the act cyclase cannot recognize substrates of altered chain lengths. This would also be consistent with the putative biosynthetic scheme for RM20 (9).

A comparison of the product profiles of the hybrid synthases reported in Table 2 with analogous hybrids between act and tcm PKS components (Table 1) support the hypothesis that the ORF2 product is the chain length determining factor (CLF). Preparation of compounds 9, 10 and 11 via cyclization of enzyme-bound ketides is schematically illustrated in FIG. 8.

EXAMPLE 5

The Role of tcmJ and tcmN in Polyketide Synthesis

To evaluate the specific catalytic roles of the PKS enzymes encoded by tcmJ and tcmN, tcmJ and tcmN were expressed in the presence of additional act and tcm PKS components in the *S. coelicolor* CH999 host-vector system described in Examples 1 through 3. The isolation of three novel polyketides from these genetic constructs has allowed the assignment of two distinct catalytic functions to tcmN.

Figure 14:
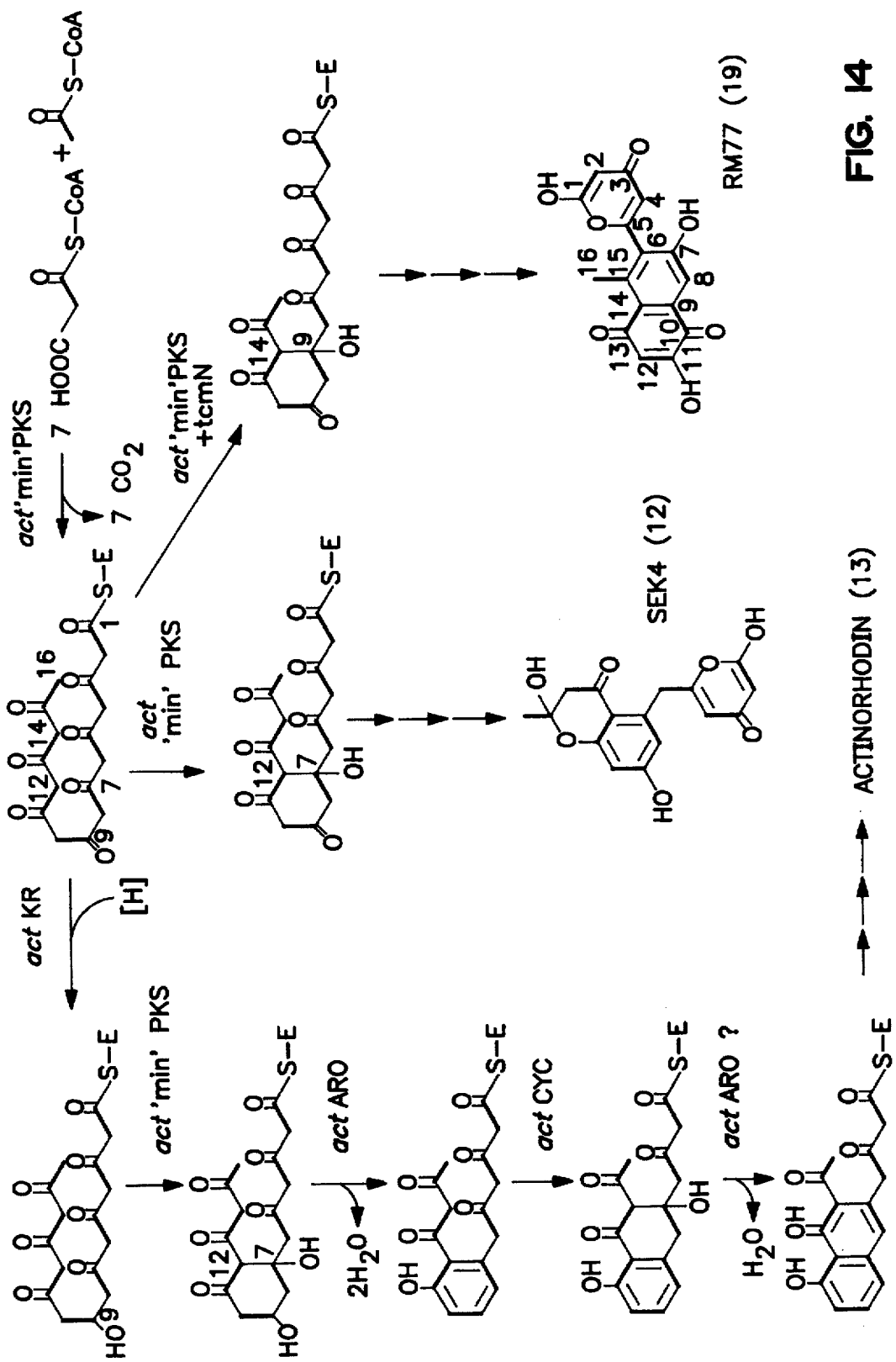
FIG. 14 illustrates the structures and proposed pathways of octaketide-derived polyketides biosynthesis including RM77 (19).
Figure 15:
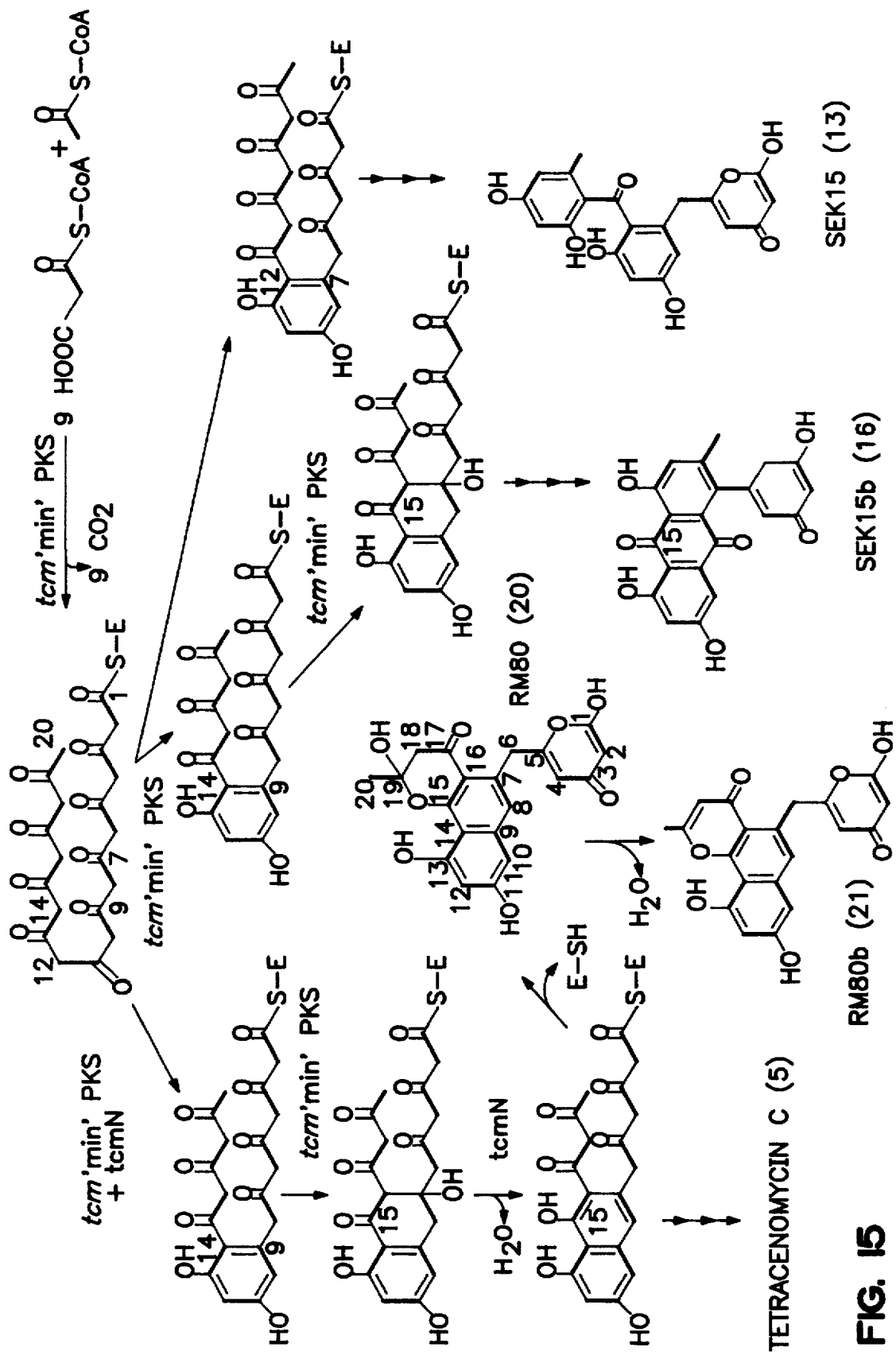
FIG. 15 illustrates the structures and proposed pathways of decaketide-derived polyketides biosynthesis including RM80 (20) and RM80b (21).

The series of recombinant gene clusters shown in Table 5 was constructed. Each plasmid contained either tcmJ, tcmN, or both in addition to the minimal PKS genes responsible for the biosynthesis of 16 (act) or 20 (tcm) carbon backbones. Half of the plasmids also contained the gene encoding the act ketoreductase (KR, actIII), which catalyzes ketoreduction at the C-9 position of the nascent polyketide backbone. The plasmids were introduced by transformation into *S. coelicolor* CH999. The major polyketides produced by the transformed strains were isolated and structurally characterized using a combination of NMR, isotopic labelling and mass spectroscopy experiments. All of the polyketides isolated have been previously structurally characterized with the exception of the novel polyketides RM77 (19) (FIG. 14), RM80 (20), and RM80b (21) (FIG. 15).

A comparative analysis of the cyclization patterns of these molecules, together with those reported earlier, reveals two functions for tcmN. The first can be illustrated by differences in the proposed pathways for RM77 (19; produced by the act minimal PKS+tcmN; pRM77) and SEK4 (12; produced by the act minimal PKS alone; pSEK24). As shown in FIG. 14, tcmN influences the regiospecificity of the cyclization of the first ring. In SEK4 (12), an intramolecular aldol condensation occurs between the C-7 carbonyl and the C-12 methylene. In contrast, a similar reaction occurs between the C-9 carbonyl and the C-14 methylene in RM77 (19); this represents a shift of one acetate unit in the polyketide backbone. Thus, while earlier results indicated that the course of this reaction is primarily controlled by the minimal PKS, RM77 (19) clearly illustrates the effect of tcmN on the act minimal PKS, which otherwise exclusively catalyzes C-7/C-12 cyclizations in the absence of tcmN. The absence of any significant amount of SEK15 (13) or other C-7/C-12 cyclized molecules in CH999/pRM80 and CH999/pRM81 also supports the conclusion that regiospecificity of the first aldol condensation can be controlled by enzymes downstream of the minimal PKS.

An important consequence of the designation the tcmN function is the temporal relationship between the catalytic ketoreduction and cyclization of the first ring. In all naturally occurring and recombinant polyketides undergoing a C-9 ketoreduction studied to date, initial cyclization occurs between carbons 7 and 12. Therefore, the inability of strains expressing tcmN to produce significant quantities of a polyketide with a C-9/C-14 cyclization in the presence of the act KR (pRM71, pRM72, pRM74, pRM75; Table 5) indicates that ketoreduction occurs prior to formation of the first ring (FIG. 14).

The second function of tcmN is apparent from comparison between the proposed cyclization pathways of RM80 (20; produced by the tcm minimal PKS+tcmN; pRM80) and SEK15b (16; produced by the tcm minimal PKS alone; pSEK33). Production of these two molecules is mutually exclusive in these strains. As seen in FIG. 15, the regiospecificities of the first and second intramolecular aldol condensations in both molecules are identical. However, in SEK15b (16) the third ring forms via an aldol condensation between C-6 and C-19, whereas in RM80 (20) it forms via hemiketalization between C-15 and C-19. The difference in these two cyclization pathways can be attributed to enolization of the C-15 carbonyl in RM80 (20), but not in SEK15b (16). This is reminiscent of the related polyketides SEK34 (22) and mutactin (6), shunt products from the early stages of actinorhodin biosynthesis which led to the hypothesis that the act aromatase (ARO) catalyzes the enolization of the C-11 carbonyl. Therefore, it is not surprising that tcmN, a homolog of the act ARO, should catalyze the same reaction; however, the specificities of the two proteins differ. Whereas the act ARO acts on the first ring, tcmN appears to act on the second ring.

TcmN provides an additional tool for the design and biosynthesis of novel polyketides through the genetic manipulation of PKSs. RM77 (19) represents the first example of a 16-carbon polyketide with an engineered first cyclization different from that of the expected "natural" one. Therefore, it is likely that other heterologous PKS complexes containing tcmN (or homologs) along with various minimal PKSs will produce polyketides of different chain length with the alternative first cyclization. This biosynthetic degree of freedom may be limited to unreduced molecules.

EXAMPLE 6

Rationally Designed Aromatic Polyketides

All identified gene clusters for actinomycete aromatic polyketides contain a set of three genes encoding a so-called 'minimal PKS' which consists of a ketosynthase (KS), which also carries a putative acyltransferase (AT) domain, a chain length factor (CLF), and an acyl carrier protein (ACP) (FIG. 1). A 16-carbon molecule, for example SEK4 (12), can be synthesized from the act minimal PKS alone. In order to produce the C-9 reduced analogue of SEK4, SEK34 (22) (FIG. 16), two additional activities are needed: a ketoreductase (KR) and an aromatizing subunit (ARO) (compare the genes present on pSEK24 and pSEK34; Table 6). The following experiments were designed to determine whether analogous pairs of molecules could be generated from backbones of alternative chain length, for example, 20 carbons using a suitable combination of a minimal PKS, a KR, and an ARO.

The tcm minimal PKS (on pSEK33; Table 6) is both necessary and sufficient for synthesis of an unreduced 20 carbon backbone (McDaniel, R. et al. *Proc. Natl. Acad. Sci. USA* (1994) 91:11542–11546), which forms SEK15 (13). In addition, the act KR can reduce the C-9 carbonyl on such a backbone to a hydroxyl, which is subsequently lost upon spontaneous aromatization of the first carbocyclic ring (Fu, H. et al. *J. Am. Chem. Soc.* (1994) 116:4166–4170). Aromatization of the reduced ring, in contrast, requires an ARO (McDaniel, R. et al. *J. Am. Chem. Soc.* (1994) 116:10855–10859). However, the act ARO cannot aromatize 20-carbon chains (McDaniel, R., et al. *Science* (1994) 262:1546–1550; McDaniel et al. *Proc. Natl. Acad. Sci. USA* (1994), supra). Furthermore, the tcm PKS cluster (which lacks a KR gene) does not appear to encode a first ring ARO which would be a suitable candidate. Accordingly, an ARO gene homologous to the one in the act cluster was chosen from the gene cluster that encodes the PKS for the 20-carbon polyketide griseusin (gris) (Yu, T.-W. et al. *J. Bacteriol.* (1994) 176:2627–2534).

The plasmid pSEK43 (Table 6), containing the tcm minimal PKS, the act KR, and the gris ARO, was constructed and introduced into the CH999 host. Analysis of the transformed strain revealed the anticipated polyketide SEK43 (23), whose structure was determined by NMR, mass spectroscopy, and isotopic labelling studies.

Figure 17:
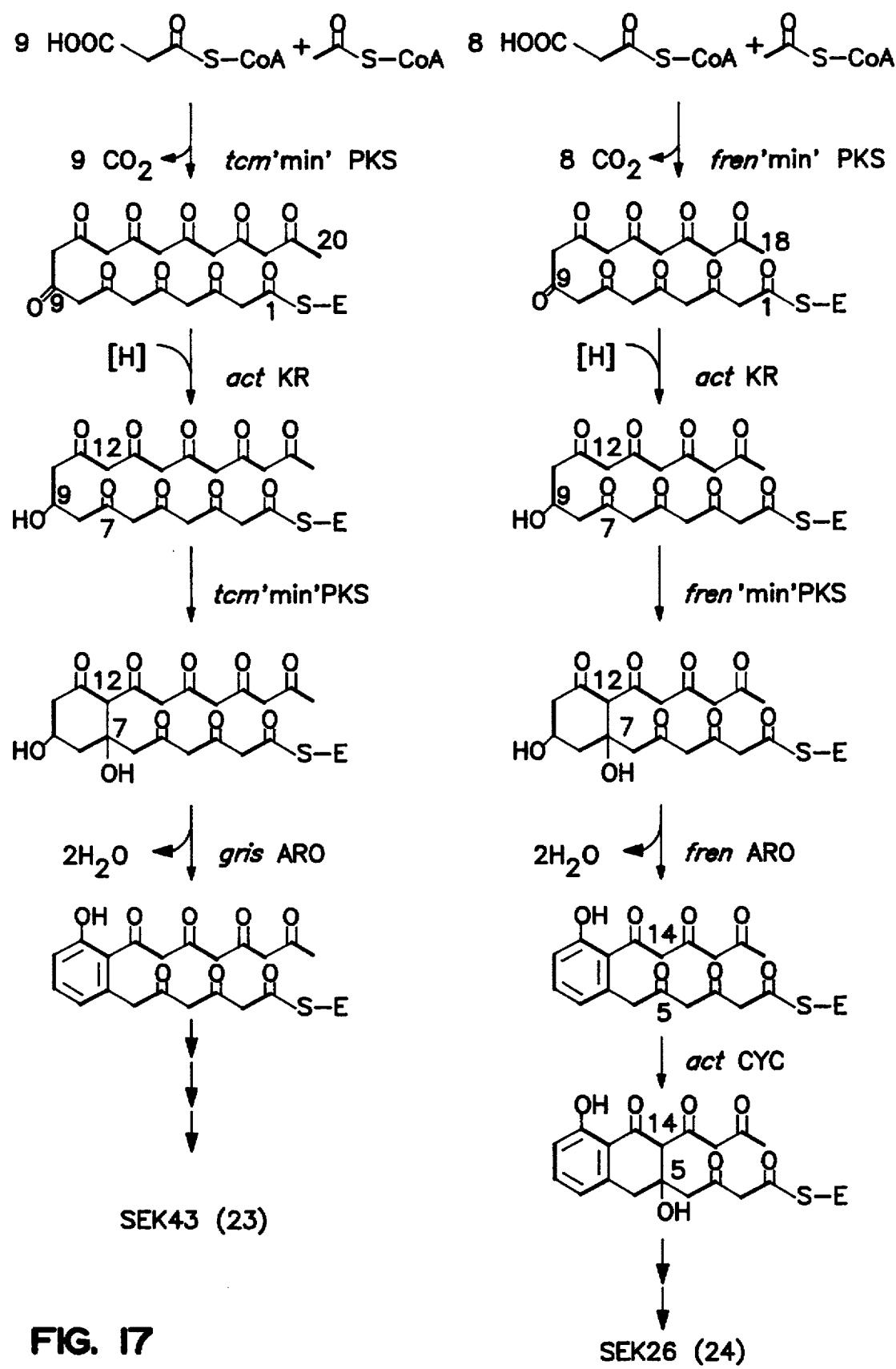
FIG. 17 is a diagram of the proposed biosynthetic pathways for the rationally designed polyketides SEK43 (23) and SEK26 (24).

The biosynthesis of SEK43 (23) (FIG. 17) reaffirms the conclusion that the act ARO and its homologues aromatize the first ring (McDaniel et al. *J. Am. Chem. Soc.* (1994), supra). Without a functional ARO, the tcm minimal PKS and act KR (pSEK23; Table 6) produce RM20b (14) (FIG. 16), which contains a non-aromatized first ring. Replacement of the tcm minimal PKS in pSEK43 with either the act or fren minimal PKSs (pSEK41 and pSEK42; Table 6) resulted in production of the 16-carbon aromatized compound SEK34 (22), demonstrating that the gris ARO can also recognize shorter carbon chains. It was unexpected, however, that a corresponding 18-carbon polyketide was not detected in the construct containing the fren minimal PKS, which has been shown to synthesize both 18- and 16-carbon chains (McDaniel et al. *J. Am. Chem. Soc.* (1993), supra). This is probably due to decomposition of the molecule, since CH999/pSEK42 produced small quantities of an uncharacterized molecule not present in CH999/pSEK34. More significantly, evidence for an aromatized 18-carbon intermediate is described below.

A second test of the concept of rational design arose from the previous isolation of the 16-carbon polyketide DMAC (28) (FIG. 16). The PKS subunits required for DMAC (28) biosynthesis are a "16-carbon" minimal PKS, a KR, and suitable ARO and CYC components (pRM5; Table 6). CYC catalyzes cyclization of the second ring between carbons 4 and 15, leading eventually to the formation of an anthraquinone (McDaniel et al. *J. Am. Chem. Soc.* (1994), supra). These observations suggested that an analogous anthraquinone, with 18 carbons, could be generated. To achieve this, the plasmid pSEK26 (Table 6) containing the fren minimal PKS with the act KR, the fren ARO, and the act CYC was constructed. The fren minimal PKS and act KR were selected for their ability to produce an 18-carbon, C-9 reduced backbone (McDaniel et al. *J. Am. Chem. Soc.* (1993), supra; McDaniel et al. *Proc. Natl. Acad. Sci. USA* (1994), supra). The fren ARO was chosen since the act ARO cannot aromatize 18-carbon chains (McDaniel et al. *J. Am. Chem. Soc.* (1993), supra; McDaniel et al. *Proc. Natl. Acad. Sci. USA* (1994), supra).

Introduction of the plasmid into CH999 resulted in the production of both DMAC (28) and SEK26 (24). The latter is a novel 18-carbon anthraquinone whose structure was confirmed by NMR, mass spectroscopy, and isotopic labelling studies. Formation of SEK26 (24) (FIG. 17) occurs through a second ring cyclization at C5/C14 presumably catalyzed by the act CYC. The production also of DMAC (28) is consistent with the relaxed chain length specificity of the fren minimal PKS (McDaniel et al. *J. Am. Chem. Soc.* (1993), supra).

In order to evaluate further the specificity of ARO and CYC subunits towards carbon chains of various lengths, several other PKS combinations were constructed (Table 6). For example, pSEK25 and pSEK26 demonstrate that the fren ARO can aromatize both 16- and 18-carbon chains. However, the fren ARO cannot handle 20-carbon chains; instead the combination of the fren ARO with the tcm minimal PKS, act KR, and act CYC (pSEK27) resulted in biosynthesis of RM20b (14), the non-aromatized 20-carbon polyketide (FIG. 16). As expected, replacing the fren ARO with the gris ARO (pRM51) in pSEK26 yielded DMAC (28) and SEK26 (24). However, attempts to generate a 20-carbon reduced polyketide with a C-5/C-14 second ring cyclization were unsuccessful; replacing the fren minimal PKS in pRM51 with the tcm minimal PKS (pRM52) resulted in production of SEK43 (23), indicating that the act CYC cannot cyclize 20-carbon chains. Finally, the plasmids pSEK44–47, pRM51, and pRM52 (Table 6), all lacking KRs, failed to cause production of polyketides different from those produced by the minimal PKS alone (McDaniel et al. *Proc. Natl. Acad. Sci. USA* (1994), supra), despite the presence of ARO and CYC components. This is consistent with previous observations that ARO and CYC subunits do not alter the biosynthetic pathways of unreduced polyketides (McDaniel et al. *Proc. Natl. Acad. Sci. USA* (1994), supra; Fu, H., McDaniel, R., Hopwood, D. A. & Khosla, C. *Biochemistry* 33:9321–9326 (1994)).

EXAMPLE 7

Construction and Analysis of Modular Polyketide Synthases

Figure 18:
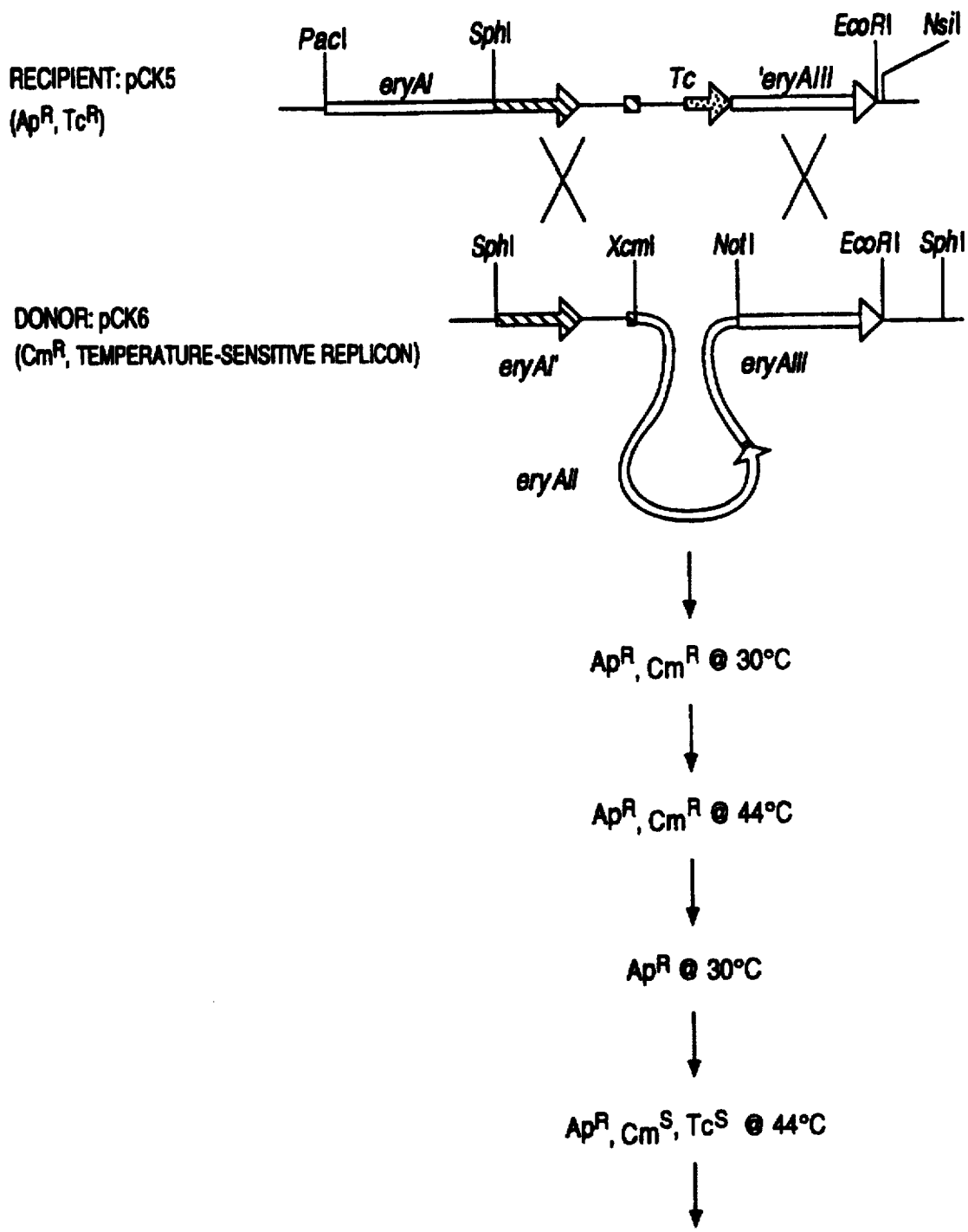
FIG. 18 shows the strategy for the construction of recombinant modular PKSs.
Figure 19:
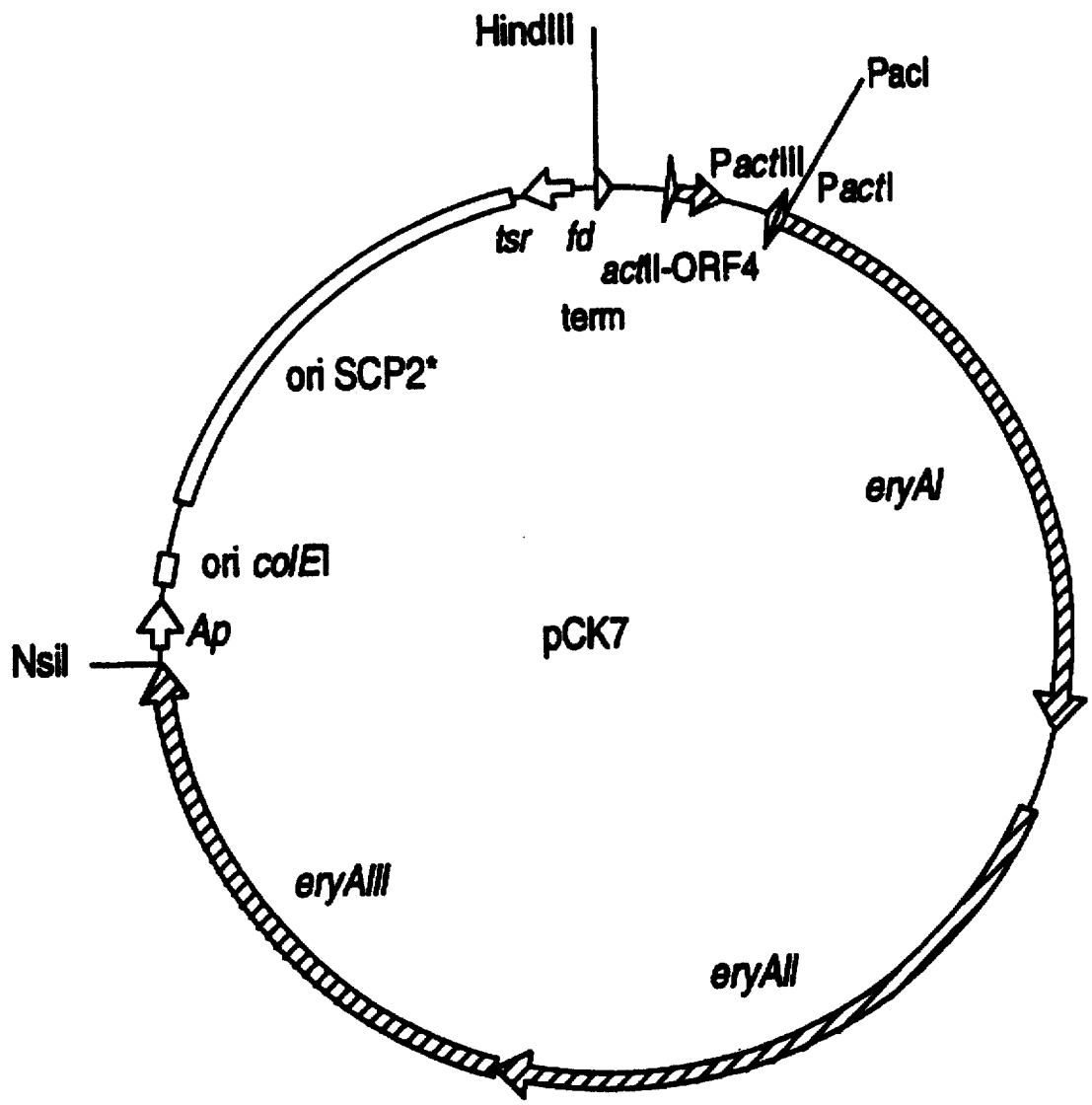
FIG. 19 is a diagram of plasmid pCK7.

Expression plasmids containing recombinant modular DEBS PKS genes were constructed by transferring DNA incrementally from a temperature-sensitive "donor" plasmid, i.e., a plasmid capable of replication at a first, permissive temperature and incapable of replication at a second, non-permissive temperature, to a "recipient" shuttle vector via a double recombination event, as depicted in FIG. 18. pCK7 (FIG. 19), a shuttle plasmid containing the complete eryA genes, which were originally cloned from pS1 (Tuan et al. (1990) *Gene* 90:21), was constructed as follows. A 25.6 kb SphI fragment from pS1 was inserted into the SphI site of pMAK705 (Hamilton et al. (1989) *J. Bacteriol.* 171:4617) to give pCK6 (Cm$^R$), a donor plasmid containing eryAII, eryAIII, and the 3' end of eryAI. Replication of this temperature-sensitive pSC101 derivative occurs at 30° C. but is arrested at 44° C. The recipient plasmid, pCK5 (Ap$^R$, Tc$^R$), includes a 12.2 kb eryA fragment from the eryAI start codon (Caffrey et al. (1992) *FEBS Lett.* 504:225) to the XcmI site near the beginning of eryAII, a 1.4 kb EcoRI-BsmI pBR322 fragment encoding the tetracycline resistance gene (Tc), and a 4.0 kb NotI-EcoRI fragment from the end of eryAIII. PacI, NdeI, and ribosome binding sites were engineered at the eryAI start codon in pCK5. pCK5 is a derivative of pRM5 (McDaniel et al. (1993), supra). The 5' and 3' regions of homology (FIG. 18, striped and unshaded areas) are 4.1 kb and 4.0 kb, respectively. MC1061 *E. coli* was transformed (see, Sambrook et al., supra) with pCK5 and pCK6 and subjected to carbenicillin and chloramphenicol selection at 30° C. Colonies harboring both plasmids (Ap$^R$, Cm$^R$) were then restreaked at 44° C. on carbenicillin and chloramphenicol plates. Only cointegrates formed by a single recombination event between the two plasmids were viable. Surviving colonies were propagated at 30° C. under carbenicillin selection, forcing the resolution of the cointegrates via a second recombination event. To enrich for pCK7 recombinants, colonies were restreaked again on carbenicillin plates at 44° C. Approximately 20% of the resulting colonies displayed the desired phenotype (Ap$^R$, Tc$^S$,Cm$^S$). The final pCK7 candidates were thoroughly checked via restriction mapping. A control plasmid, pCK7f, which contains a frameshift error in eryAI, was constructed in a similar manner. pCK7 and pCK7f were transformed into *E. coli* ET12567 (MacNeil (1988) *J. Bacteriol.* 330:5607) to generate unmethylated plasmid DNA and subsequently moved into *Streptomyces coelicolor* CH999 using standard protocols (Hopwood et al. (1985) *Genetic manipulation of Streptomyces. A laboratory manual.* The John Innes Foundation: Norwich).

Upon growth of CH999/pCK7 on R2YE medium, the organism produced abundant quantities of two polyketides (FIG. 20). The addition of propionate (300 mg/L) to the growth medium resulted in approximately a two-fold increase in yield of polyketide product. Proton and $^{13}$C NMR spectroscopy, in conjunction with propionic-1-$^{13}$C acid feeding experiments, confirmed the major product as 6dEB (17) (>40 mg/L). The minor product was identified as 8,8a-deoxyoleandolide (18) (>10 mg/L), which apparently originates from an acetate starter unit instead of propionate in the 6dEB biosynthetic pathway. $^{13}$C$_2$ sodium acetate feeding experiments confirmed the incorporation of acetate into (18). Three high molecular weight proteins (>200 kDa), presumably DEBS1, DEBS2, and DEBS3 (Caffrey et al. (1992) *FEBS Lett.* 304:225), were also observed in crude extracts of CH999/pCK7 via SDS-polyacrylamide gel electrophoresis. No polyketide products were observed from CH999/pCK7f. The inventors hereby acknowledge support provided by the American Cancer Society (IRG-32–34).

EXAMPLE 8

Manipulation of Macrolide Ring Size by Directed Mutagenesis of DEBS

In order to investigate the relationship between structure and function in modular PKSs and to apply this knowledge towards the rational and stochastic design of novel polyketides, a host-vector expression system was designed to study DEBS (Kao, C. M. et al. *Science* (1994) 265:509–512). Using this expression system, the expression of DEBS1 alone, in the absence of DEBS2 and DEBS3, resulted in the production of (2R,3S,4S,5R)-2,4-dimethyl-3,5-dihydroxy-n-heptanoic acid δ-lactone ("the heptanoic acid δ-lactone" (25)) (1–3 mg/L), the expected triketide product of the first two modules (FIG. 21A) (Kao, C. M. et al. *J. Am. Chem. Soc.* (1994) 116:11612–11613). The synthesis of the heptanoic acid δ-lactone (25) provided further biochemical evidence for the modular PKS model of Katz and coworkers (Donadio, S. et al. *Science* (1991), supra) and showed that a thioesterase is not essential for release of a triketide from the enzyme complex.

In this Example the role of the thioesterase (TE) domain in DEBS was analyzed by constructing two additional deletion mutant PKSs that consist of different subsets of the DEBS modules and the TE. The first PKS contained DEBS1 fused to the TE, whereas the second PKS included the first five DEBS modules with the TE; plasmids pCK12 and pCK15 contained the genes encoding the bimodular ("1+2+TE") and pentamodular ("1+2+3+4+5+TE") PKSs.

The 1+2+TE PKS contained a fusion of the carboxy-terminal end of the acyl carrier protein of module 2 (ACP-2) to the carboxy-terminal end of the acyl carrier protein of module 6 (ACP-6). Thus ACP-2 is essentially intact in this PKS and is followed by the amino acid sequence naturally found between ACP-6 and the TE (FIG. 21B). Plasmid pCK12 contained eryA DNA originating from pS1 (Tuan, J. S. et al. *Gene* (1990) 90:21). pCK12 is identical to pCK7 (Kao et al. *Science* (1994), supra) with the exception of a deletion between the carboxy-terminal ends of ACP-2 and ACP-6. The fusion occurs between residues L3455 of DEBS1 and Q2891 of DEBS3. An SpeI site is present between these two residues so that the DNA sequence at the fusion is CTCACTAGTCAG.

Figure 22:
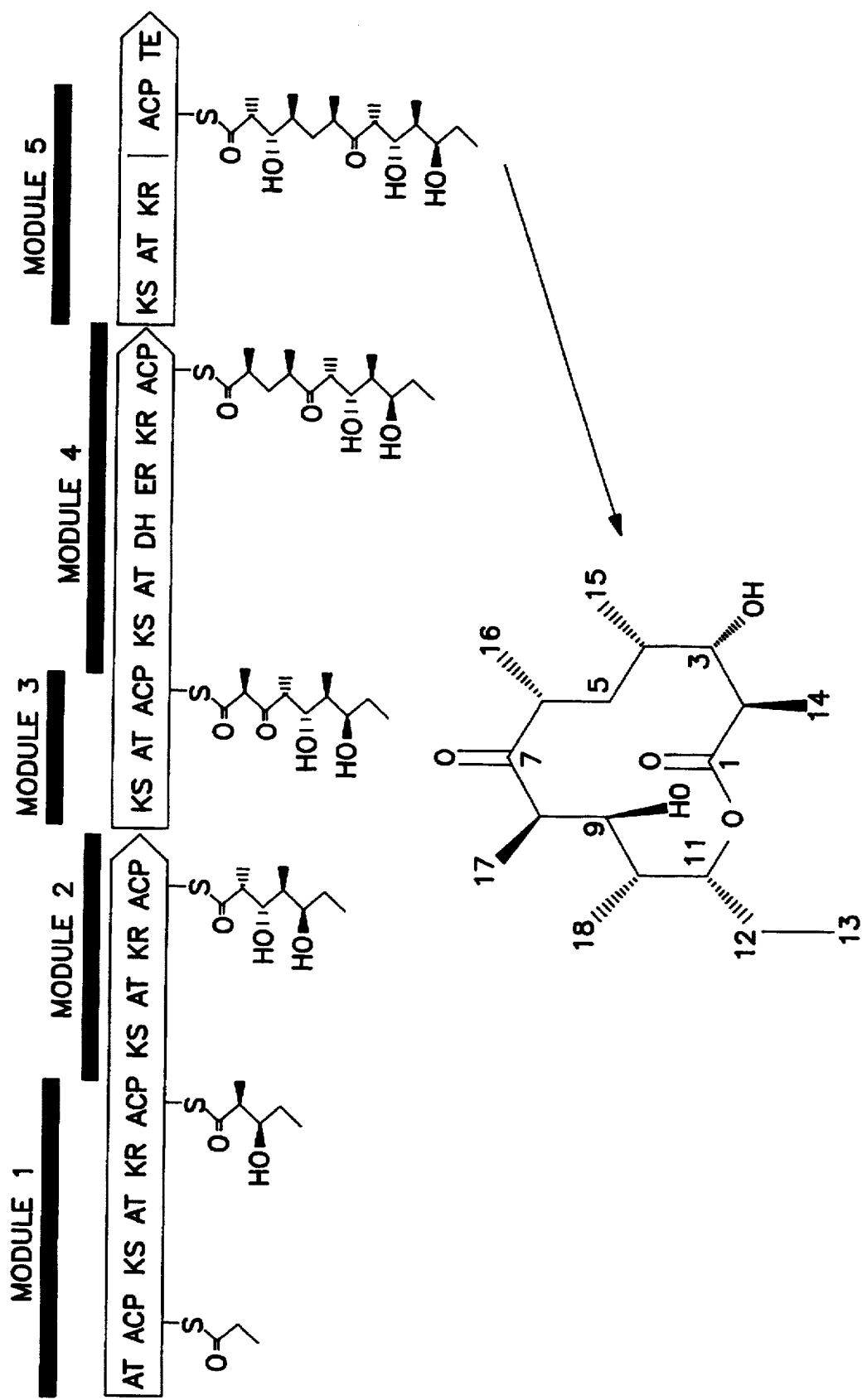
FIG. 22 shows the biosynthesis of (8R,9S)-8,9-dihydro-8-methyl-9-hydroxy-10-deoxymethonolide (27) by the "1+2+3+4+5+TE" PKS in S. coelicolor CH999. The vertical line between KR-5 and ACP-6 represents the fusion junction in this deletion mutant.

The 1+2+3+4+5+TE PKS contained a fusion 76 amino acids downstream of the β-ketoreductase of module 5 (KR-5) and five amino acids upstream of ACP-6. Thus, the fusion occurs towards the carboxy-terminal end of the non-conserved region between KR-5 and ACP-5, and the recombinant module 5 was essentially a hybrid between the wild type modules 5 and 6 (FIG. 22). Plasmid pCK15 contained eryA DNA originating from pS1 (Tuan et al. *Gene* (1990), supra). pCK15 is a derivative of pCK7 (Kao et al. *Science* (1994), supra) and was constructed using an in vivo recombination strategy described earlier (Kao et al. *Science* (1994), supra). pCK15 is identical to pCK7 with the exceptions of a deletion between KR-5 and ACP-6, which occurs between residues G1372 and A2802 of DEBS3, and the insertion of a blunted SalI fragment containing a kanamycin resistance gene (Oka A. et al. *J. Mol. Biol.* (1981) 147:217) into the blunted HindIII site of pCK7. An arginine residue is present between G1372 and A2802 so that the DNA sequence at the fusion is GGCCGCGCC.

Plasmids pCK12 and pCK15 were introduced into *S. coelicolor* CH999 and polyketide products purified from the transformed strains according to methods previously described (Kao et al. *Science* (1994), supra).

CH999/pCK12 produced the heptanoic acid δ-lactone (25) (20 mg/L) as determined by $^1$H and $^{13}$C NMR spectroscopy. This triketide product is identical to that produced by CH999/pCK9, which expresses the unmodified DEBS1 protein alone (Kao *J. Am. Chem. Soc.* (1994), supra. However, CH999/pCK12 produced the heptanoic acid δ-lactone (25) in significantly greater quantities than CH999/pCK9 (>10 mg/L vs. ~1 mg/L), indicating the ability of the TE to catalyze thiolysis of a triketide chain attached to the ACP domain of module 2. CH999/pCK12 also produced significant quantities of a novel analog of (2R,3S,4S,5R)-2,4-dimethyl-3,5-dihydroxy-n-hexanoic acid δ-lactone ("the hexanoic acid δ-lactone (26)) (10 mg/L), that resulted from the incorporation of an acetate start unit instead of propionate. This is reminiscent of the ability of CH999/pCK7, which expresses intact DEBS, to produce 8,8a-deoxyoleandolide (18) in addition to 6dEB (17) (Kao et al. *Science* (1994), supra).

Since the hexanoic acid δ-lactone (26) was not detected in CH999/pCK9, its facile isolation from CH999/pCK12 provides additional evidence for the increased turnover rate of DEBS1 due to the presence of the TE. In other words, the TE can effectively recognize an intermediate bound to a "foreign" module that is four acyl units shorter than its natural substrate, 6dEB (17). However, since the triketide products can probably cyclize spontaneously into the heptanoic acid δ-lactone (25) and the hexanoic acid δ-lactone (26) under typical fermentation conditions (pH 7), it is not possible to discriminate between a biosynthetic model involving enzyme-catalyzed lactonization and one involving enzyme-catalyzed hydrolysis followed by spontaneous lactonization. Thus, the ability of the 1+2+TE PKS to recognize the C-5 hydroxyl of a triketide as an incoming nucleophile is unclear.

The second recombinant strain, CH999/pCK15, produced abundant quantities of (8R,9S)-8,9-dihydro-8-methyl-9-hydroxy-10-deoxymethonolide ("the 10-deoxymethonolide (27); FIG. 22) (10 mg/L), demonstrating that the pentamodular PKS is active. The 10-deoxymethonolide (27) was characterized using $^1$H and $^{13}$C NMR spectroscopy of natural abundance and $^{13}$C-enriched material, homonuclear correlation spectroscopy (COSY), heteronuclear correlation spectroscopy (HETCOR), mass spectrometry, and molecular modeling. The 10-deoxymethonolide (27) is an analog of 10-deoxymethonolide (Lambalot, R. H. et al. *J. Antibiotics* (1992) 45:1981–1982), the aglycone of the macrolide antibiotic methymycin. The production of the 10-deoxymethonolide (27) by a pentamodular enzyme demonstrates that active site domains in modules 5 and 6 in DEBS can be joined without loss of activity. If this proves to be a general feature of the multimodular proteins that constitute modular PKSs, then any structural model for module assembly must account for the fact that individual modules as well as active sites are independent entities which do not depend on association with neighboring modules to be functional. Most remarkably, the 12-membered lactone ring, formed by esterification of the terminal carboxyl with the C-11 hydroxyl of the hexaketide product, indicated the ability of the 1+2+3+4+5+TE PKS, and possibly the TE itself, to catalyze lactonization of a polyketide chain one acyl unit shorter than the natural product of DEBS, 6dEB (17). Indeed, the formation of the 10-deoxymethonolide (27) may mimic the biosynthesis of the closely related 12-membered hexaketide macrolide, methymycin, which frequently occurs with the homologous 14-membered heptaketide macrolides, picromycin and/or narbomycin (Cane, D. E. et al. *J. Am. Chem. Soc.* (1993) 115:522–566). A modular PKS such as DEBS could thus be used to generate a wide range of macrolactones with shorter as well as longer chain lengths. The latter products would require the introduction of additional heterologous modules into DEBS.

The construction of the 1+2+3+4+5+TE PKS resulted in the biosynthesis of a previously uncharacterized 12-membered macrolactone that closely resembles, but is distinct from, the aglycone of a biologically active macrolide. The apparent structural and functional independence of active site domains and modules as well as relaxed lactonization specificity suggest the existence of many degrees of freedom for manipulating these enzymes to produce new modular PKSs. Libraries of new macrolides can be generated by altering the association of active site domains and entire modules, the subset of reductive domains within each module, the activity of the TE, and possibly even downstream modification reactions such as hydroxylation and glycosylation. Such libraries could prove to be rich sources of new leads for drug discovery Thus, novel polyketides, as well as methods for recombinantly producing the polyketides, are disclosed. Although preferred embodiments of the subject invention have been described in some detail, it is understood that obvious variations can be made without departing from the spirit and the scope of the invention as defined by the appended claims.

TABLE 1

| Plasmid | ORF1 (KS/AT) | ORF2 (CLDF) | ORF3 (ACP) | Major Product(s) | Backbone Carbon Length |
|---|---|---|---|---|---|
| pRM5 | act | act | act | 1,2 | 16 |
| pRM7 | gra | act | act | 1,2 | 16 |
| pRM12 | act | gra | act | 1,2 | 16 |
| pRM22 | act | act | gra | 1,2 | 16 |
| pRM10 | tcm | act | act | 1,2 | 16 |
| pRM15 | act | tcm | act | NP | — |
| pRM20 | tcm | tcm | act | 9 | 20 |
| pRM25 | act | act | tcm | 1,2 | 16 |
| pRM35 | tcm | act | tcm | NP | — |
| pRM36 | act | tcm | tcm | NP | — |
| pRM37 | tcm | tcm | tcm | 9,14,15 | 20 |
| pSEK15 | tcm | tcm | tcm | 13,16 | 20 |
| pSEK33 | tcm | tcm | act | 13,16 | 20 |

TABLE 2

| Plasmid | ORF1 (KS/AT) | ORF2 (CLDF) | ORF3 (ACP) | Major Product(s) |
|---|---|---|---|---|
| pRM5 | act | act | act | 1,2 |
| pRM8 | fren | act | act | 1,2 |
| pRM13 | act | fren | act | NP |
| pRM23 | act | act | fren | 1,2 |
| pRM18 | fren | fren | act | 1,2,10,11 |
| pRM32 | fren | act | fren | NP |
| pRM33 | act | fren | fren | NP |
| pRM34 | fren | fren | fren | 1,2,10,11 |

TABLE 3

$^1$H(400 MHz) and $^{13}$C(100 MHz) NMR data from RM18(10) and RM18b(11)

| carbon$^\alpha$ | $^{13}$Cδ(ppm) | (J$_{CC}$(Hz)) | $^1$Hδ(ppm) (m,J$_{HH}$(Hz),area)) |
|---|---|---|---|
| | RM18 | | |
| 2 | 29.6 | NC$^b$ | 2.2(s, 3H) |
| 3 | 203.7 | 37.7 | |
| 4 | 47.0 | 36.9 | 3.6(s, 2H) |
| 5 | 149.6 | 77.2 | |
| 6 | 106.7 | 77.4 | 6.2(s, 1H) |
| 7 | 129.1 | 61.9 | |
| 8 | 114.4 | 62.1 | 6.7(d, 7.2, 1H) |
| 9 | 130.1 | 58.9 | 7.3(dd, 8.4, 7.4, 1H) |
| 10 | 120.6 | 59.2 | 7.6(d, 8.9, 1H) |
| 11 | 132.7 | 56.0 | |
| 12 | 116.7 | 55.7 | |
| 13 | 155.6 | 74.7 | |
| 14 | 98.4 | 74.9 | |
| 15 | 158.8 | 69.6 | 6.4(s, 1H) |
| 16 | 113.6 | 69.3 | 11.2(s, 1OH) |
| 17 | 201.7 | 41.9 | |
| 18 | 32.4 | 41.7 | 2.5(s, 3H) |

TABLE 3-continued $^1$H(400 MHz) and $^{13}$C(100 MHz) NMR data from RM18(10) and RM18b(11)

| carbon$^\alpha$ | $^{13}$Cδ(ppm) | (J$_{CC}$(Hz)) | $^1$Hδ(ppm) (m,J$_{HH}$(Hz),area)) |
|---|---|---|---|
| | RM18b | | |
| 2 | 18.8 | | 2.1(s, 3H) |
| 3 | 152.3 | | |
| 4 | 104.0 | | 6.1(s, 1H) |
| 5 | 130.0 | | |
| 6 | 113.5 | | 6.7(d, 7.0) |
| 7 | 130.1 | | 7.3(dd, 7.1, 8.7, 1H) |
| 8 | 120.1 | | 7.6(d, 8.6, 1H) |
| 9 | 132.8 | | |
| 10 | 116.6 | | |
| 11 | 155.9 | | |
| 12 | 98.2 | | |
| 13 | 159.1 | | 6.4(s, 1H) |
| 14 | 113.8 | | 11.2(s, 1OH) |
| 15 | 201.7 | | |
| 16 | 32.4 | | 2.5(s, 3H) |

$^\alpha$carbons are labelled according to their number in the polyketide backbone
$^b$NC, not coupled

TABLE 4

$^1$H and $^{13}$C NMR data for SEK4 (12) and SEK15 (13)$^a$

| carbon$^b$ | $^{13}$Cδ(ppm) | J$_{CC}$(Hz) | $^1$Hδ(ppm) |
|---|---|---|---|
| | SEK4 (12) | | |
| 1 | 165.4 | 78.8 | 11.60(s, 1OH) |
| 2 | 88.2 | 79.8 | 6.26(d, J=2.28Hz, 1H) |
| 3 | 170.5 | 55.3 | |
| 4 | 111.3 | 61.3 | 6.33(d, J=2.24Hz, 1H) |
| 5 | 163.8 | 51.0 | |
| 6 | 37.6 | 50.8 | 4.07(d, J=15.7Hz, 1H) |
| | | | 4.16(d, J=16.0Hz, 1H) |
| 7 | 138.6 | 60.7 | |
| 8 | 102.9 | 60.9 | 5.66(d, J=1.6Hz, 1H) |
| 9 | 161.9 | 71.9 | 10.50(s, 1OH) |
| 10 | 100.6 | 70.9 | 5.19(d, J=1.96Hz, 1H) |
| 11 | 162.9 | 60.8 | |
| 12 | 112.9 | 61.6 | |
| 13 | 191.1 | 39.1 | |
| 14 | 49.3 | 39.9 | 2.54(d, J=15.9Hz, 1H) |
| | | | 4.92(d, J=16.0Hz, 1H) |
| 15 | 99.6 | 46.6 | 6.90(s, 1OH) |
| 16 | 27.5 | 46.8 | 1.56(s, 3H) |
| | SEK15 (13) | | |
| 1 | 164.0 | 79.1 | 12.20(s, 1OH) |
| 2 | 88.2 | 79.4 | 6.20(d, J=1.88Hz, 1H) |
| 3 | 172.8 | 57.9 | |
| 4 | 101.8 | 53.9 | 6.20(d, J=1.88Hz, 1H) |
| 5 | 163.1 | 50.4 | |
| 6 | 36.7 | 50.8 | 1.90(s, 2H) |
| 7 | 135.4 | 60.7 | |
| 8 | 109.1 | 61.7 | 5.66 (s, 1H) |
| 9 | 159.8 | 66.2 | |
| 10 | 101.6 | 66.5 | 5.08 (s, 1H) |
| 11 | 157.4 | 67.3 | |
| 12 | 121.1 | 67.6 | |
| 13 | 200.3 | 58.1 | |
| 14 | 117.2 | 58.6 | |
| 15 | 163.6 | 68.5 | |
| 16 | 100.6 | 68.0 | 6.08 (s, 1H) |
| 17 | 162.2 | 62.6 | |
| 18 | 111.0 | 62.0 | 6.12(s, 1H) |

TABLE 4-continued $^1$H and $^{13}$C NMR data for SEK4 (12) and SEK15 (13)[a]

| carbon[b] | $^{13}$Cδ(ppm) | $J_{CC}$(Hz) | $^1$Hδ(ppm) |
|---|---|---|---|
| 19 | 141.9 | 43.3 | |
| 20 | 21.1 | 42.7 | 1.86(s, 3H) |

[a]$^1$H and $^{13}$C NMR's were recorded in DMSO-$d_6$ (400 MHz for $^1$H and 100 MHz for $^{13}$C)
[b]carbons are labelled according to their number in the polyketide backbone

TABLE 5

| Plasmid | Minimal PKS* | KR | tcmJ,N | Major Product(s) |
|---|---|---|---|---|
| pSEK21 | act | act | — | 6 |
| pRM70 | act | act | J | 6 |
| pRM71 | act | act | N | 6 |
| pRM72 | act | act | J,N | 6 |
| pSEK23 | tcm | act | — | 10 |
| pRM73 | tcm | act | J | 10 |
| pRM74 | tcm | act | N | 10 |
| pRM75 | tcm | act | J,N | 10 |
| pSEK24 | act | — | — | 12 |
| pRM76 | act | — | J | 12 |
| pRM77 | act | — | N | 19 |
| pRM78 | act | — | J,N | 19 |
| pSEK33 | tcm | — | — | 13,16 |
| pRM79 | tcm | — | J | 13,16 |
| pRM80 | tcm | — | N | 20,21 |
| pRM81 | tcm | — | J,N | 20,21 |

*The minimal PKS contains the ketosynthase/putative acyl transferase, chain length factor, and act acyl carrier protein.

TABLE 6

| Plasmid | Minimal PKS* | KR | ARO | CYC | Major Product |
|---|---|---|---|---|---|
| pSEK24 | act | — | — | — | 12 |
| pSEK34 | act | act | act | — | 22 |
| pRM5 | act | act | act | act | 28 |
| pSEK33 | tcm | — | — | — | 13 |
| pSEK23 | tcm | act | — | — | 14 |
| pSEK41 | act | act | gris | — | 22 |
| pSEK42 | fren | act | gris | — | 22 |
| pSEK43 | tcm | act | gris | — | 23 |
| pSEK25 | act | act | fren | act | 28 |
| pSEK26 | fren | act | fren | act | 28/24 |
| pSEK27 | tcm | act | fren | act | 14 |
| pRM51 | fren | act | gris | act | 28/24 |
| pRM52 | tcm | act | gris | act | 23 |
| pSEK44 | act | — | gris | — | 12 |
| PSEK45 | tcm | — | gris | — | 13 |
| pSEK46 | act | — | fren | act | 12 |
| pSEK47 | tcm | — | fren | act | 13 |
| pRM53 | act | — | gris | act | 12 |
| PRM54 | tcm | — | gris | act | 13 |

*The minimal PKS contains the ketosynthase/putative acyl transferase, chain length factor, and act acyl carrier protein.

---

We claim:

1. A library for synthesis of a multiplicity of polyketides which library comprises a multiplicity of individual cell lines wherein each cell line produces a functional polyketide synthase (PKS) such that each said cell line produces a different polyketide;

wherein each functional PKS comprises the products of: a first open reading frame (ORF) encoding a ketosynthase/acyltransferase (KS/AT); a second ORF encoding an acyl carrier protein (ACP); and a third ORF encoding a chain length determining factor (CLDF);

wherein the ORFs in said library are derived from at least three different aromatic PKS.

2. The library of claim 1 wherein at least some of said multiplicity of cell lines further include an ORF encoding a polyketide cyclase (CYC); and/or an ORF encoding polyketide aromatase (ARO); and/or an ORF encoding a polyketide ketoreductase (KR).

3. The library of claim 1 which includes colonies wherein the functional PKS comprises the product of at least one of:

| ORF1 (KS/AT) | ORF2 (CLDF) | ORF3 (ACP) |
|---|---|---|
| act | act | act |
| gra | act | act |
| act | gra | act |
| act | act | gra |
| tcm | act | act |
| tcm | tcm | act |
| act | act | tcm |
| fren | act | act |
| act | act | fren |
| tcm | tcm | tcm |
| fren | fren | act |
| fren | fren | fren |

4. The library of claim 1 wherein said cell line further comprises an enzyme that is active on a PKS and is selected from the group consisting of an O-methyl transferase and glycosyl transferase.

5. The library of claim 1 wherein in at least one member of said library each said open reading frame is contained in a separate expression cassette.

* * * * *

UNITED STATES PATENT AND TRADEMARK OFFICE
CERTIFICATE OF CORRECTION

PATENT NO. : 5,712,146
DATED : Jan. 27, 1998
INVENTOR(S) : Chaitan Khosla, et al It is certified that error appears in the above-identified patent and that said Letters Patent is hereby corrected as shown below:

On title page,

Under "[75] Inventors," please replace "Suzanne Ebert-Khosla" with --Susanne Ebert-Khosla--.

Signed and Sealed this

Sixth Day of October, 1998

Attest:

BRUCE LEHMAN

Attesting Officer

Commissioner of Patents and Trademarks

UNITED STATES PATENT AND TRADEMARK OFFICE

CERTIFICATE OF CORRECTION

PATENT NO. : 5,712,146

DATED : January 27, 1998

INVENTOR(S) : Chaitan Khosla, David A. Hopwood, Susanne Ebert-Khosla, Robert McDaniel, Hong Fu, and Camilla Kao.

It is certified that error appears in the above-identified patent and that said Letters Patent is hereby corrected as shown below:

ON THE TITLE PAGE:

Add "The John Innes Centre, England." as assignee.

Signed and Sealed this

Twenty-second Day of August, 2000

Attest:

Q. TODD DICKINSON

*Attesting Officer*          *Director of Patents and Trademarks*